(12) United States Patent
Campbell et al.

(10) Patent No.: US 9,943,518 B2
(45) Date of Patent: Apr. 17, 2018

(54) INHIBITORS OF PHOSPHODIESTERASE TYPE 5A FOR REDUCING SKELETAL MUSCLE FATIGUE, EDEMA, AND DAMAGE IN A PATIENT HAVING MUSCLE FATIGUE DUE TO INCREASED AGE OR EXERCISE

(71) Applicant: University of Iowa Research Foundation, Iowa City, IA (US)

(72) Inventors: Kevin P. Campbell, Iowa City, IA (US); Yvonne M. Kobayashi, Indianapolis, IN (US); Robert W. Crawford, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/163,937

(22) Filed: May 25, 2016

(65) Prior Publication Data
US 2016/0263118 A1 Sep. 15, 2016

Related U.S. Application Data

(63) Continuation of application No. 14/020,401, filed on Sep. 6, 2013, now Pat. No. 9,387,210, which is a continuation of application No. 13/034,938, filed on Feb. 25, 2011, now abandoned, which is a continuation-in-part of application No. PCT/US2009/055215, filed on Aug. 27, 2009.

(60) Provisional application No. 61/092,209, filed on Aug. 27, 2008.

(51) Int. Cl.
| | | |
|---|---|---|
| A61K 31/519 | (2006.01) | |
| A61K 31/66 | (2006.01) | |
| A61K 31/4985 | (2006.01) | |
| A61K 31/53 | (2006.01) | |

(52) U.S. Cl.
CPC ........ *A61K 31/519* (2013.01); *A61K 31/4985* (2013.01); *A61K 31/66* (2013.01); *A61K 31/53* (2013.01)

(58) Field of Classification Search
CPC .. A61K 31/4985; A61K 31/519; A61K 31/53; A61K 31/66
See application file for complete search history.

(56) References Cited

FOREIGN PATENT DOCUMENTS

WO   WO 2005077925 A1 * 8/2005 ........... C07D 207/48

OTHER PUBLICATIONS

Eston et. al., Journal of Exercise Science and Fitness, 2003, vol. 1(2), pp. 85-96.*
Kotera et. al., European Journal of Biochemistry, 1999, FEBS, vol. 262, pp. 866-872.*
Waters et. al., Mechanisms of Ageing and Development, 2003, Elsevier, vol. 124, pp. 301-309.*
Marqueste et al., "Comparative MRI analysis of T2 changes associated with single and repeated bouts of downhill running leading to eccentric-induced muscle damage", J Appl Physiol, 2008, 105:299-307.
McDonald et al., "Use of step activity monitoring for continuous physical activity assessment in boys with Duchenne muscular dystrophy", Arch Phys Med Rehabil, Apr. 2005, 86:802.
McDonald et al., "The 6-minute walk test as a new outcome measure in Duchenne muscular dystrophy", Muscle & Nerve, Apr. 2010, 500.
Miki et al., "Mouse model of prinzmetal angina by disruption of the inward rectifier Kir6.1", Nature Medicine, May 2002, 8(5):466.
Narkar et al., "AMPK and PPAR agonists are exercise mimetics", Cell, Aug. 8, 2008, 134(3):405-415.
Ozawa et al., "Molecular and cell biology of the sarcoglycan complex", Muscle & Nerve, Nov. 2005, 563.
Padma-Nathan, Oral Drug Therapy of Sexual Dysfunction: A Guide to Clinical Management, ed. Gregory Broderick, Chapter 4, pp. 65-83.
Perretti et al., "The microcirculation and inflammation: Site of action for glucocorticoids", Microcirculation, 2000, 7:147-161.
Persson et al., "Endogenous nitric oxide reduces microvascular permeability and tissue oedema during exercise in cat skeletal muscle", J Vasc Res, 2003, 40:538-546.
Phillips et al., "Exercise therapy in patients with myopathy", Current Opinion in Neurology, 2000, 13:547-552.
Pomplun et al., "Elevation of blood glucose following anaesthetic treatment in C57Bl/6 Mice", Horm Metab res, 2004, 36:67-69.
Prior et al., "Reduced skeletal muscle capillarization and glucose intolerance", Microcirculation, Apr. 2009, 16(3):203-212.
Punkt et al., "Nitric oxide synthase is up-regulated in muscle fibers in muscular dystrophy", Biochemical and Biophysical Research Communications, 2006, 348:259-264.
Radley et al., "Duchenne muscular dystrophy: Focus on pharmaceutical and nutritional interventions", The International Journal of Biochemistry & Cell Biology, 2007, 39:469-477.
Restrepo, Neurology, 2004, AAN Enterprises, vol. 62, pp. E10-E11.
Roberds et al., "Primary structure and muscle-specific expression of the 5-0-kDa dystrophin-associated Glycoprotein (Adhalin)", Journal of Biological Chemistry, Nov. 15, 1993, 268(32):23739-23742.
Schillings et al., "Experienced and physiological fatigue in neuromuscular disorders", Clinical Neurophysiology, 2007, 118:292-300.
Scime et al., "Molecular-targeted therapy for Duchenne muscular dystrophy", Mol Diag Ther, 2008, 12(2):99-108.
Seddon et al., "Neuronal nitric oxide synthase regulates basal microvascular tone in humans in vivo", Circulation, 2008, 117:1991-1996.
Sigmund et al., "Regulated tissue- and cell-specific expression of the human renin gene in transgenic mice", Circulation Research, 1992, 70:1070-1079.

(Continued)

*Primary Examiner* — Sarah Pihonak
(74) *Attorney, Agent, or Firm* — Andrus Intellectual Property Law, LLP

(57) ABSTRACT

Disclosed are pharmaceutical compositions and methods for treating or preventing muscle diseases or the symptoms thereof. The compositions typically include and the methods typically utilize phosphodiesterase type 5A inhibitors.

6 Claims, 23 Drawing Sheets

(56) References Cited

OTHER PUBLICATIONS

Soltanzadeh et al., "Clinical and genetic characterization of manifesting carriers of DMD mutations", Neuromuscular Disorders, 2010, 20:499-504.
Spurney et al., "Preclinical drug trials in the mdx mouse: Assessment of reliable and sensitive outcome measures", Muscle & Nerve, 2009, 39:591-602.
Stamler et al., "Physiology of nitric oxide in skeletal muscle", Physiological Reviews, Jan. 2001, 81(1):209.
St-Pierre et al., "Glucocorticoid treatment alleviates dystrophic myofiber pathology by activation of the calcineurin/NF-AT pathway", The FASEB Journal, 2004.
Straub et al,. "Animal models for muscular dystrophy show different patterns of sarcolemmal disruption", Journal of Cell Biology, Oct. 20, 1997, 139(2):375-385.
Straub et al., "ε-Sarcoglycan replaces α-Sarcoglycan in smooth muscle to form a unique dystrophin-glycoprotein complex", The Journal of Biological Chemistry, Sep. 24, 1999, 274(39):27989-27996.
Suzuki et al., "NO production results in suspension-induced muscle atrophy through dislocation of neuronal NOS", Journal of Clinical Investigation, Sep. 2007, 117(9):2468.
Takimoto et al., "Chronic inhibition of cyclic GMP phosphodiesterase 5A prevents and reverses cardiac hyptertrophy", Nature Medicine, Feb. 2005, 11(2):214.
Tanda et al., "Abnormal social behavior, hyperactivity, impaired remote spatial memory, and increased DI-mediated dopaminergic signaling in neuronal nitric oxide sythase knockout mice" Molecular Brain, 2009, 2:19.
Terzis et al., "Fiber type composition and capillary density in relation to submaximal number of repetitions in resistance exercise", Journal of Strength and Conditioning Research, May 2008, 22(3):845-850.
Thomas et al., "Impaired metabolic modulation of alpha-adrenergic vasoconstriction in dystrophin-deficient skeletal muscle", PNAS, Dec. 1998, 95:15090-15095.
Thomas et al., "Vasomodulation by skeletal muscle-derived nitric oxide requires a-syntrophin-mediated sarcolemmal localization of neuronal nitric oxide sythase", Circulation Research, 2003, 92:554-560.
Thompson et al., "The effects of rod and cone loss on the photic regulation of locomotor activity and heart rate", European Journal of Neuroscience, 2008, 28:724-729.
Torelli et al., "Absence of neuronal nitric oxide synthase (nNOS) as a pathological marker for the diagnosis of Becker muscular dystrophy with rod domain deletions", Neuropathology and Applied Neurobiology, 2004, 30:540-545.
Tsunoda et al., "Determination of catecholamines and their 3-O-methyl metabolites in mouse plasma", Biomedical Chromatography, 2001, 15:41-44.
Villalta et al., "Shifts in macrophage phenotypes and macrophage competition for arginine metabolism affect the severity of muscle pathology in muscular dystrophy", Human Molecular Genetics, 2009, 18(3):482-496.
Voikar et al., "Long-term individual housing in C57BL/6J and DBA/2 mice: assessment of behavioural consequences", Genes, Brain and Behavior, 2005, 4:240-252.
Wang et al., "Nitric oxide in skeletal muscle: Inhibition of nitric oxide synthase inhibits walking speeds in rats", Nitric Oxide: Biology and Chemistry, 2001, 5(3):219-232.
Wang et al., "Adenosine A3 receptor stimulation induces protection of skeletal muscle from eccentric exercise-mediated injury", Am J Physiol Regul Integr Comp Physiol, 2010, 299:R259-R267.
Wehling et al., "A nitric oxide synthase transgene ameliorates muscular dystrophy in mdx mice", Journal of Cell Bioloby, Oct. 1, 2001, 155(1):123-131.
Weiss et al., "Exercise-induced left ventrical systolic dysfunction in women heterozygous for dystrophinopathy", J Am Soc Echocardiogr, Aug. 2010, 23(8):848-53.
Williamson et al., "Dystroglycan is esential for early embryonic development: disruption of Reichert's membrane in Dag1-null mice", Human Molecular Genetics, 1997, 6(6):831-841.
Wooddell et al., "Use of evans blue dye to compare limb muscles in exercised young and old mdx mice", Muscle & Nerve, Apr. 2010, 487.
Yokoyama et al., "Muscle fatigue increases the probability of developing hyperalgesia in mice", J Pain, Sep. 2007, 8(9):692-699.
Zwarts et al., "Clinical neurophysiology of fatigue", Clinical Neurophysiology, 2007.
Gomez-Moreno et al., Transplantation Proceedings, 37, 1550-1551 (2005).
Acharyya et al., "Interplay of IKK/NF-KB signaling in macrophages and myofibers promotes muscle degeneration in Duchenne muscular dystrophy", Journal of Clinical Investigation, Apr. 2007, 117(4):889-901.
Anderson et al., "Correlated NOS-Iμ and myf5 expression by satellite cells in mdx mouse muscle regeneration during NOS manipulation and deflazacort treatment", Neuromuscular Disorders, 2003, 13:388-396.
Archer et al., "Persistent and improved functional gain in mdx dystrophic mice after treatment with L-arginine and deflazacort", FASEB Journal, Feb. 7, 2006.
Asai et al., "Primary role of functional ischemia, quantitative evidence for the two-hit mechanism, and phosphodiesterase-5 inhibitor therapy in mouse muscular dystrophy", PLoS One, Aug. 2007, 8:e806.
Barbato, "Nicorandil: the drug that keeps on giving", Hypertension, 2005, 46:647-648.
Bellinger et al., "Hypernitrosylated ryanodine receptor/calcium release channels are leaky in dystrophic muscle", Nat Med, Mar. 2009, 15(3):325-330.
Black et al., "Muscle injury after repeated bouts of voluntary and electrically stimulated exercise", Med Sci Sports Exerc, Sep. 2008, 40(9):1605-1615.
Blake et al., "Function and genetics of dystrophin and dystrophin-related proteins in muscle", Phsiol Rev, 2002, 82:291-329.
Bloom, "Cyclic nucleotide phosphodiesterase isozymes expressed in mouse skeletal muscle", Can. j. Physiol. Pharmacol., 2002, 80:1132-1135.
Bloom, "Age-related alterations in cyclic nucleotide phosphodiesterase activity in dystrophic mouse leg muscle", Can. J. Physiol. Pharmacol., 2005, 83:1055-1060.
Brooks et al., "Contractile properties of skeletal muscles from young, adult and aged mice", Journal of Physiology, 1988, 404:71-82.
Chao et al., "Muscular dystrophy in mdx mice despite lack of neuronal nitric oxide synthase", Journal of Neurochemistry, 1998, 784.
Cohn et al., "Prevention of cardiomyopathy in mouse models lacking the smooth muscle sarcoglycan-sarcospan complex", Journal of Clinical Investigation, 2001, 107:R1-R7.
Collins, "On the Inheritance of Handedness", J. Hered., 1968, 59(1):9-12.
Consolino et al., "Muscles of mice deficient in alpha-sarcoglycan maintain large masses and near control force values throughout the life span", Physiol. Genomics, 2005, 22:244-256.
Corbin et. al., The Journal of Biological Chemistry, 1999, The American Society for Biochemistry and Molecular Biology, vol. 274, No. 20, pp. 13729-13732.
Crosbie et al., "mdx muscle pathology is independent of nNOS perturbation", Human Molecular Genetics, 1998, 7(5):823-829.
Crosbie et al., "Membrane targeting and stabilization of sarcospan is mediated by the sarcoglycan subcomplex", Journal of Cell Biology, Apr. 5, 1999, 145(1):153-165.
Dalakas, The Lancet, 2003, Little, Brown, & Co., vol. 362, pp. 971-982.
Duclos et al., "Progressive muscular dystrophy in alpha-sarcoglycan-deficient mice", Journal of Cell Biology, Sep. 21, 1998, 142(6):1461-1471.
Durbeej et al., "Disruption of the beta-sarcoglycan gene reveals pathogenetic complexity of limb-girdle muscular dystrophy type 2E", Molecular Cell, Jan. 2000, 5:141-151.

(56) References Cited

OTHER PUBLICATIONS

Ervasti et al., "Membrane organization of the dystrophin-glycoprotein complex", Cell, Sep. 21, 1991, 66:1121-1131.
Eu et al., "Concerted regulation of skeletal muscle contractility by oxygen tension and endogenous nitric oxide", PNAS, Dec. 9, 2003, 100(25):15229-15234.
Fadel et al., "Impaired vasomodulation is associated with reduced neuronal nitric oxide synthase in skeletal muscle of ovariectomized rats", J Physiol, 2003, 549(1):243-253.
Francis et. al., Current Urology Reports, 2003, Current Science, vol. 4, pp. 457-465.
Garry et al., "Mice without myoglobin", Nature, Oct. 29, 1998, 395:905.
Gaudreault et al., "Gait patterns comparison of children with Duchenne muscular dystrophy to those of control subjects considering the effect of gait velocity", Gait & Posture, 2010, 32:342-347.
Glowka, "Stereoselective pharmacokinetics of ibuprofen and its lysinate from suppositories in rabbits", International Journal of Pharmaceutics, 2000, 199:159-166.
Grady et al., "Skeletal and cardiac myopathies in mice lacking utrophin and dystrophin: a model for duchenne muscular dystrophy", Cell, Aug. 22, 1997, 90:729-738.
Grady et al., "Role for alpha-dystrobrevin in the pathogenesis of dystrophin-dependent muscular dystrophies", Nature Cell Biology, Aug. 1999, 1:215.
Grady et al., "Subtle neuromuscular defects in utrophin-deficient mice", Journal of Cell Biology, Feb. 24, 1997, 136(4):871-882.
Gupta et al., "The Clinical Pharmacokinetics of Phosphodiesterase-5 Inhibitors for Erectile Dysfunction", J Clin Pharmacol, 2005, 45:987.
Harper et al., "Modular flexibility of dystrophin: Implications for gene therapy of Duchenne muscular dystrophy", Nature Medicine, Mar. 2002, 8(3):253.
Hougee et al., "Oral administration of the NADPH-oxidase inhibitor apocynin partially restores diminished cartilage proteoglycan synthesis and reduces inflammation in mice", European Journal of Pharmacology, 2006, 531:264-269.
Huang et al., "Hyptertension in mice lacking the gene for endothelial nitric oxide synthase", Letters to Nature, Sep. 21, 1995, 377:239.
Hyatt et al., "Creatine kinase release and clearance using MM variants following repeated bouts of eccentric exercise", Med Sci Sports Exerc, 1998, 30(7)1059-1065.
Imamura et al., "Epsilon-sarcoglycan compensates for lack of alpha-sarcoglycan in a mouse model of limb-girdle muscular dystrophy", Human Molecular Genetics, 2005, 14(6):775-783.
Jiang et. al., Bioorganic and Medicinal Chemistry, 2004, Elsevier, vol. 12, pp. 1505-1515.
Johnson et al., "Muscle creatine kinase sequence elements regulating skeletal and cardiac muscle expression in transgenic mice", Molecular and Cellular Biology, Aug. 1989, 9(8):3393-3399.
Judge et al., "Dissecting the signaling and mechanical functions of the dystrophin-glycoprotein complex", Journal of Cell Science, 2005, 119:1537-1546.
Juel et. al., Current Treatment Options in Neurology, 2005, Current Science, vol. 7, pp. 3-14.
Kalkman et al., "The development of a model of fatigue in neuromuscular disorders: A longitudinal study", Journal of Psychosomatic Research, 2007, 62:571-579.
Kameya et al., "alpha1-syntrophin gene disruption results in the absence of neuronal-type nitric-oxide synthase at the sarcolemma but does not induce muscle degeneration", Journal of Biological Chemistry, Jan. 22, 1999, 274(4):2193-2200.
Kass et al., "Phosphodiesterase Type 5: expanding roles in cardiovascular regulation", Circulation Research, 2007, 101:1084-1095.
Kinugawa et al., "Limited exercise capacity in heterozygous manganese superoxide dismutase gene-knockout mice: roles of superoxide anion and nitric oxide", Circulation, 2005, 111:1480-1486.
Kobayashi et al., "Sarcolemma-localized nNOS is required to maintain activity after mild exercise", Nature, Nov. 27, 2008, 456:511-515.
Kunkel et. al., Journal of Human Genetics, 2006, National Institutes of Health, vol. 51, issue 5, pp. 397-406.
Lebakken et al., "Sarcospan-deficient mice maintain normal muscle function", Molecular and Cellular Biology, Mar. 2000, 20(5):1669-1677.
Lynch et al., "Contractile properties of diaphragm muscle segments from old mdx and old transgenic mdx mice", Cell Physiol, 41:1997, C2063.
Marden et al., "Compositional analysis of muscle in boys with Duchenne muscular dystrophy using MR imaging", Skeletal Radiol, 2005, 34:140-148.

\* cited by examiner

```
SEQUENCE LISTING

<160> NUMBER OF SEQ ID NOS: 1

<210> SEQ ID NO 1
<211> LENGTH: 16
<212> TYPE: PRT
<213> ORGANISM: Mus musculus

<400> SEQUENCE: 1

Cys Gln Thr Gln Ile Pro Gln Pro Gln Thr Thr Gly Lys Trp Tyr Pro
1               5                   10                  15
```

INHIBITORS OF PHOSPHODIESTERASE TYPE 5A FOR REDUCING SKELETAL MUSCLE FATIGUE, EDEMA, AND DAMAGE IN A PATIENT HAVING MUSCLE FATIGUE DUE TO INCREASED AGE OR EXERCISE

CROSS-REFERENCE TO RELATED APPLICATIONS

The present application is a continuation application of U.S. application Ser. No. 14/020,401, filed on Sep. 6, 2013, which application was published on Jan. 2, 2014, as U.S. Publication No. US20140005202, which application is a continuation application of U.S. application Ser. No. 13/034,938, filed on Feb. 25, 2011 and now abandoned, which application was published as U.S. Publication No. US20110160219 on Jun. 30, 2011, and further which application is a continuation-in-part application of International Application No. PCT/US2009/055215, filed on Aug. 27, 2009, which application was published as International Published Application No. WO 2010/025266, on Mar. 4, 3010 in the English language, which claims the benefit of U.S. Provisional Application No. 61/092,209, filed on Aug. 27, 2008, the contents of which are incorporated herein by reference in their entireties.

STATEMENT REGARDING U.S. GOVERNMENT SPONSORED RESEARCH OR DEVELOPMENT

This invention was made with government support under 5RO1AR051199-04 awarded by the National Institutes of Health. The government has certain rights in the invention.

BACKGROUND

The present invention relates generally to the field of muscle disease (i.e., myopathy) and pharmaceutical compositions for the treatment or prevention of muscle disease or the symptoms thereof. In particular, the present invention relates to the field of neuromuscular diseases such as muscular dystrophies and pharmaceutical compositions for the treatment or prevention of symptoms thereof.

Many neuromuscular conditions are characterized by an exaggerated exercise-induced fatigue response that is disproportionate to activity level. This fatigue does not necessarily correlate with elevated central or peripheral fatigue in patients (Schillings et al. 2007), and some patients experience severe fatigue without any demonstrable somatic disease (Zwarts et al. 2007). Except in myopathies that are due to specific metabolic defects, the mechanism underlying this type of fatigue remains unknown (Zwarts et al. 2007). With no treatment available, this form of inactivity is a major determinant of disability (Kalkman et al. 2007). Here, using mouse models, it is shown that this exaggerated fatigue response is distinct from a loss in specific force production by muscle, and that sarcolemma-localized nNOS signaling in skeletal muscle is required to maintain activity after mild exercise. Of significance, nNOS-null mice have no muscle pathology and no loss of muscle specific-force after exercise, but do display this exaggerated fatigue response to mild exercise. In mouse models of nNOS mislocalization from the sarcolemma, prolonged inactivity was only relieved by pharmacologically enhancing the cGMP signal that results from muscle nNOS activation during the nitric oxide signaling response to mild exercise. These findings suggest that the mechanism underlying the exaggerated fatigue response to mild exercise is a lack of contraction-induced signaling from sarcolemma-localized nNOS, which reduces cGMP-mediated vasomodulation in the vessels that supply active muscle after mild exercise. Notably, sarcolemmal nNOS was reduced in patient biopsies from a large number of distinct myopathies, suggesting a common mechanism of fatigue. These results suggest that patients with an exaggerated fatigue response to mild exercise would show clinical improvement in response to treatment strategies aimed at improving exercise-induced signaling such as strategies that improve cGMP signaling.

SUMMARY

Disclosed are composition and methods for treating muscle diseases or preventing the symptoms thereof in a patient. The methods typically include administering an effective amount of a cGMP specific phosphodiesterase type 5A (PDE5A) inhibitor to a patient in order to treat or prevent symptoms of muscles diseases such as fatigue or edema (e.g., activity-induced fatigue or edema experienced by the patient after mild exercise).

The disclosed methods may include treating muscular dystrophy in a patient in need thereof by administering an effective amount of a cGMP specific phosphodiesterase type 5A (PDE5A) inhibitor such as sildenafil to the patient. In some embodiments, the patient may have a muscular dystrophy disease such as Duchenne muscular dystrophy or Becker muscular dystrophy (e.g., the patient may be a human patient having Duchenne muscular dystrophy or Becker muscular dystrophy). The effective amount may be effective for treating or preventing activity-induced fatigue in the patient (e.g., the effective amount may reduce fatigue in the patient after exercise, including mild exercise). In other embodiments, the effective amount may be effective for treating or preventing muscle damage in the patient (e.g., the effective amount may reduce muscle damage in the patient after exercise, including mild exercise, as assessed by creatine kinase (CK) levels in the patient's serum).

Suitable PDE5A inhibitors may include, but are not limited to: sildenafil, sildenafil analogs, sildenafil derivatives, or pharmaceutical salts thereof; tadalafil, tadalafil analogs, tadalafil derivatives, or pharmaceutical salts thereof; and vardenafil, vardenafil analogs, vardenafil derivatives, or pharmaceutical salts thereof. Suitable effective dosages may include, but are not limited to about 10-30 mg/kg body mass, e.g., administered daily or on an as needed basis.

The disclosed methods also may include methods for reducing fatigue after exercise in a patient having muscular dystrophy (e.g., a human having Duchenne or Becker muscular dystrophy), where the method includes administering an effective amount of a specific PDE5A inhibitor (e.g., 10-30 mg/kg of sildenafil per body mass) to the patient before, during, or after exercise. In some embodiments, the specific PDE5A inhibitor is administered no later than about 24, 18, 12, 6, 3, or 1 hour(s) before exercise.

BRIEF DESCRIPTION OF THE DRAWINGS

As shown in FIG. 1e, microdystrophin/mdx mice have excessive inactivity after mild exercise, despite contractility being normal.

DETAILED DESCRIPTION

Figure 1:
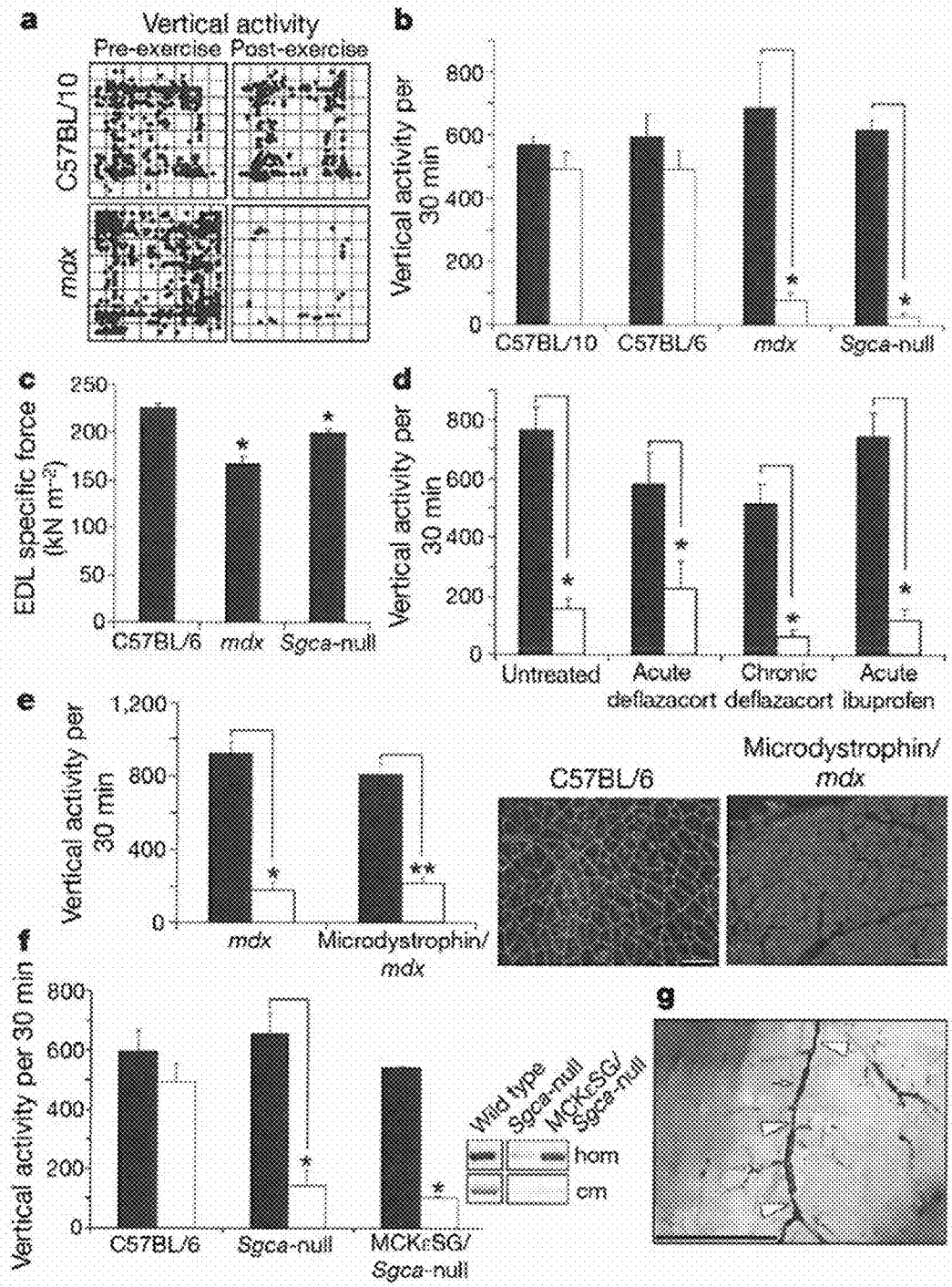
FIG. 1. illustrates that loss of sarcolemma-localized nNOS leads to skeletal muscle vascular narrowings, reduced capillary perfusion, and an exaggerated fatigue response after mild exercise in dystrophic and non-dystrophic mouse models.

Disclosed are pharmaceutical compositions and methods for treating or preventing muscle diseases and the symptoms thereof. The present invention is described herein using definitions, as set forth below and throughout the application.

Definitions

Unless otherwise specified or indicated by context, the terms "a", "an", and "the" mean "one or more."

As used herein. "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

The terms "patient" and "subject" may be used interchangeably herein. A patient may be a human patient. A patient may refer to a human patient having or at risk for acquiring a muscle disease. Patients who are treated with the pharmaceutical compositions disclosed herein may be at risk for acquiring muscular dystrophy or may have already acquired muscular dystrophy.

A "patient in need thereof" may include a patient having a muscle disease (e.g., muscular dystrophy) or at risk for developing a muscle disease (e.g., muscular dystrophy). For example, a patient in need thereof may include a patient having Duchenne muscular dystrophy or Becker muscular dystrophy. A "patient in need thereof" further may include a patient having a myopathy (e.g., muscle weakness that accompanies aging, HIV disease, or cancer). A "patient in need thereof" may include a patient exhibiting one or more symptoms of a muscle disease (e.g., muscle fatigue or edema after exercise).

As contemplated herein, muscle diseases may include muscular dystrophy (MD). As used herein, muscular dystrophy refers to a group of genetic, hereditary muscle diseases that cause progressive muscle weakness and which may be characterized by progressive skeletal muscle weakness, defects in muscle proteins, and the death of muscle cells and tissue. Muscular dystrophy includes, but is not limited to the following diseases: Duchenne (DMD), Becker (BMD), limb girdle muscular dystrophy (LGMD), congenital (CMD), facioscapulohumeral (FSHD), myotonic, oculopharyngeal, distal, and Emery-Dreifuss.

The methods disclosed and contemplated herein include methods for treating or preventing fatigue in patients having or at risk for developing muscle diseases. As used herein, muscle diseases include, but are not limited to DMD; BMD; CMD/LGMD (e.g., muscle diseases associated with mutations in the protein O-mannosyltransferase 1 gene (POMT1), the protein O-mannosyltransferase 2 gene (POMT2), the protein O-mannose beta-1,2-N-acetylglucosaminyltransferase gene (POMGnT1), or the fukutin gene (FKTN)); LGMD-2A; LGMD-2B; LGMD-2D; LGMD-2E; LGMD-2I; muscle diseases associated with mutations in the δ-sarcoglycan gene (SG, including three 2C cases); Ullrich congential muscular dystrophy (UCMD); congenital merosin-deficient, 1A (MDC1A) muscular dystrophy; myositis; autophagic vacuolar myopathy; myopathies not associated with a specific protein deficiency; myotonic dystrophy type 1(DM1); spinal muscular atrophy (SMA); critical care myopathy cases; Pompe disease; and sarcoidosis; wherein the methods include administering an effective amount of a phosphodiesterase type 5A inhibitor or a pharmaceutical salt thereof to the patient (e.g., sildenafil, tadalafil, or vardenafil).

As used herein, the phrase "therapeutically effective amount" shall mean that dosage of an active agent that provides the specific pharmacological response for which the active agent is administered in a significant number of subjects in need of such treatment. A therapeutically effective amount of an active agent that is administered to a particular subject in a particular instance will not always be effective in treating the conditions/diseases described herein, even though such dosage is deemed to be a therapeutically effective amount by those of skill in the art.

The pharmaceutical compositions disclosed herein may be formulated for administration to a subject in need thereof. Such compositions can be formulated and/or administered in dosages and by techniques well known to those skilled in the medical arts taking into consideration such factors as the age, sex, weight, and condition of the particular patient, and the route of administration.

The pharmaceutical compositions may be administered prophylactically or therapeutically. In prophylactic administration, the pharmaceutical compositions may be administered in an amount sufficient to prevent symptoms of a disease (e.g., in an amount sufficient to prevent muscle fatigue after exercise in a patient having a muscle disease and/or in an amount sufficient to prevent muscle damage after exercise in a patient having a muscle disease and/or in an amount sufficient to prevent edema after exercise in a patient having a muscle disease). In therapeutic applications, the pharmaceutical compositions are administered to a patient in an amount sufficient to elicit a therapeutic effect (e.g., in an amount sufficient to treat muscle fatigue after exercise in a patient having a muscle disease and/or in an amount sufficient to treat muscle damage after exercise in a patient having a muscle disease and/or in an amount sufficient to treat edema after exercise in a patient having a muscle disease).

The pharmaceutical compositions disclosed herein typically include a cGMP specific phosphodiesterase type 5A inhibitor (i.e., a PDE5A inhibitor). PDE5A catalyzes the degradation of cGMP. The PDE5A inhibitors contemplated herein will inhibit PDE5A-mediated degradation of cGMP and may help to increase cGMP levels or at least may help to maintain cGMP levels after administration. Specific PDE5A inhibitors may include but are not limited to sildenafil (sold under the tradename Viagra®), tadalafil (sold under the tradename Cialis®), vardenafil (sold under the tradename Levitra®), and pharmaceutical salts thereof. PDE5A inhibition assays are known in the art. (See Terrett, N. K. et al., "Sildenafil (Viagra), a potent and selective inhibitor of Type 5 cGMP phosphodiesterase with utility for the treatment of male erectile dysfunction." *Bioorg. Med. Chem. Lett.* 1996, 6, 1819-1824, incorporated herein by reference in its entirety).

Sildenafil has the IUPUC name 5-[2-ethoxy-5-(4-methylpiperazin-1-yl)sulfonylphenyl]-1-methyl-3-propyl-4H-pyrazolo[5,4-e]pyrimidin-7-one and has the formula:

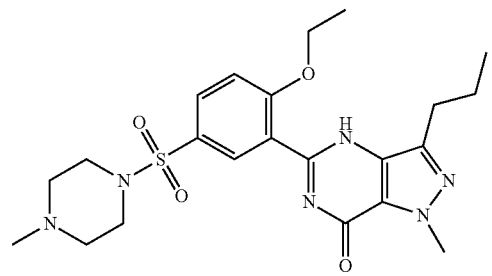 [SMILES: CCCc1nn(C)c2c(=O)nc(-c3cc(S(=O)(=O)N4CCN(C)CC4)ccc3OCC)[nH]c12]

The pharmaceutical compositions disclosed herein may include sildenafil, a sildenafil analog, a sildenafil derivative, or a pharmaceutical salt thereof having PDE5A-inhibitory activity. For example, sildenafil analogs or derivatives having a formula:

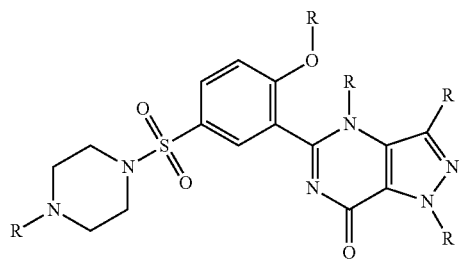

where R is hydrogen or a $C_1$-$C_6$ branched or straight chain alkyl group and where the sildenafil analogs or derivatives have PDE5A-inhibitory activity are contemplated.

In some embodiments, sildenafil, a sildenafil analog, a sildenafil derivative, or a pharmaceutical salt thereof may include, but is not limited to any of the following compounds: PF-581253; 5-[2-ethoxy-5-(4-methylpiperazin-1-yl)sulfonylphenyl]-1-methyl-3-propyl-4H-pyrazolo[4,3-d]pyrimidin-7-one; 5-[2-ethoxy-5-(4-methylpiperazin-1-yl)sulfonylphenyl]-1-methyl-3-propyl-4H-pyrazolo[4,3-d]pyrimidin-7-one; 2-hydroxypropane-1,2,3-tricarboxylic acid; 5-[2-ethoxy-5-(4-methylpiperazin-1-yl)sulfonylphenyl]-3-(3-hydroxypropyl)-1-methyl-4H-pyrazolo[4,3-d]pyrimidin-7-one; 3-ethyl-5-[5-(4-ethylpiperazin-1-yl)sulfonyl-2-(2-methoxyethoxy)pyridin-3-yl]-2-(pyridin-2-ylmethyl)-4H-pyrazolo[4,3-d]pyrimidin-7-one; 5-(5-acetyl-2-butoxypyridin-3-yl)-3-ethyl-2-(pyridin-2-ylmethyl)-4H-pyrazolo[4,3-d]pyrimidin-7-one; 5-(5-acetyl-2-butoxypyridin-3-yl)-3-ethyl-2-(1-ethylazetidin-3-yl)-4H-pyrazolo[4,3-d]pyrimidin-7-one; 5-(5-acetyl-2-ethoxyphenyl)-1-methyl-3-propyl-4H-pyrazolo[4,3-d]pyrimidin-7-one; 5-(5-acetyl-2-propoxypyridin-3-yl)-3-ethyl-2-(1-ethylazetidin-3-yl)-4H-pyrazolo[4,3-d]pyrimidin-7-one; 5-(5-acetyl-2-propoxypyridin-3-yl)-3-ethyl-2-(1-methylpiperidin-4-yl)-4H-pyrazolo[4,3-d]pyrimidin-7-one; 5-(5-acetyl-2-propoxypyridin-3-yl)-3-ethyl-2-piperidin-4-yl-4H-pyrazolo[4,3-d]pyrimidin-7-one; 5-(5-acetyl-2-butoxypyridin-3-yl)-3-ethyl-2-[(1-methylimidazol-2-yl)methyl]-4H-pyrazolo[4,3-d]pyrimidin-7-one; 5-(5-acetyl-2-propoxypyridin-3-yl)-3-ethyl-2-[(1-methylimidazol-2-yl)methyl]-4H-pyrazolo[4,3-d]pyrimidin-7-one; 5-(5-acetyl-2-propoxypyridin-3-yl)-2-(1-methylazetidin-3-yl)-3-propyl-4H-pyrazolo[4,3-d]pyrimidin-7-one; 5-(5-acetyl-2-butoxypyridin-3-yl)-3-ethyl-2-piperidin-4-yl-4H-pyrazolo[4,3-d]pyrimidin-7-one; 5-(5-acetyl-2-butoxypyridin-3-yl)-2-(azetidin-3-yl)-3-ethyl-4H-pyrazolo[4,3-d]pyrimidin-7-one; 5-(5-acetyl-2-propoxypyridin-3-yl)-3-ethyl-2-(1-methylazetidin-3-yl)-4H-pyrazolo[4,3-d]pyrimidin-7-one; 5-(5-acetyl-2-propoxypyridin-3-yl)-3-ethyl-2-(1-ethylpiperidin-4-yl)-4H-pyrazolo[4,3-d]pyrimidin-7-one; 5-(5-acetyl-2-butoxypyridin-3-yl)-3-ethyl-2-(1-methylazetidin-3-yl)-4H-pyrazolo[4,3-d]pyrimidin-7-one; 5-(5-acetyl-2-propoxypyridin-3-yl)-2-(azetidin-3-yl)-3-ethyl-4H-pyrazolo[4,3-d]pyrimidin-7-one; 5-[5-acetyl-2-(2-methylpropoxy)pyridin-3-yl]-3-ethyl-2-(1-methylazetidin-3-yl)-4H-pyrazolo[4,3-d]pyrimidin-7-one; 5-(5-acetyl-2-propoxypyridin-3-yl)-2-(azetidin-3-yl)-3-propyl-4H-pyrazolo[4,3-d]pyrimidin-7-one; 5-(5-acetyl-2-butoxypyridin-3-yl)-3-ethyl-2-(1-ethylpiperidin-4-yl)-4H-pyrazolo[4,3-d]pyrimidin-7-one; 5-[5-acetyl-2-(2-methoxyethoxy)pyridin-3-yl]-3-ethyl-2-(2-morpholin-4-ylethyl)-4H-pyrazolo[4,3-d]pyrimidin-7-one; 5-(5-acetyl-2-butoxypyridin-3-yl)-3-ethyl-2-(1-methylpiperidin-4-yl)-4H-pyrazolo[4,3-d]pyrimidin-7-one; 5-(5-acetyl-2-propoxypyridin-3-yl)-3-ethyl-2-(1-propan-2-ylazetidin-3-yl)-4H-pyrazolo[4,3-d]pyrimidin-7-one; 5-(5-acetyl-2-butoxypyridin-3-yl)-3-ethyl-2-(2-morpholin-4-ylethyl)-4H-pyrazolo[4,3-d]pyrimidin-7-one; 5-[2-ethoxy-5-(2-morpholin-4-ylacetyl)phenyl]-1-methyl-3-propyl-4H-pyrazolo[4,3-d]pyrimidin-7-one; and 5-[2-butoxy-5-(1-hydroxyethyl)pyridin-3-yl]-3-ethyl-2-(1-ethylazetidin-3-yl)-4H-pyrazolo[4,3-d]pyrimidin-7-one.

Tadalafil has the formula:

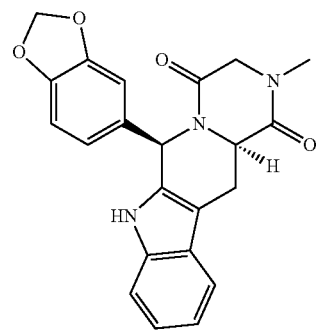 [SMILES: CN1CC(=O)N2[C@H](c3ccc4c(c3)OCO4)c3[nH]c4ccccc4c3C[C@@H]2C1=O]

The pharmaceutical compositions disclosed herein may include tadalafil, a tadalafil analog, a tadalafil derivative, a tadalafil isomer (including stereoisomers), or a pharmaceutical salt thereof having PDE5A-inhibitory activity. For example, tadalafil analogs, derivatives, or isomers having a formula:

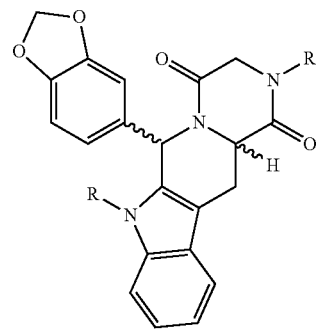

where R is hydrogen or a $C_1$-$C_6$ branched or straight chain alkyl group and where the tadalafil analogs, derivatives, or isomers have PDE5A-inhibitory activity are contemplated.

Vardenafil has the IUPUC name 2-[2-ethoxy-5-(4-ethylpiperazin-1-yl)sulfonylphenyl]-5-methyl-7-propyl-1H-imidazo[5,1-f][1,2,4]triazin-4-one and has the formula:

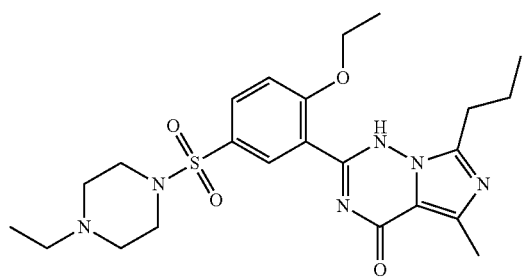 [SMILES: CCCc1nc(C)c2c(=O)nc(-c3cc(S(=O)(=O)N4CCN(CC)CC4)ccc3OCC)[nH]n12]

The pharmaceutical compositions disclosed herein may include vardenafil, a vardenafil analog, a vardenafil derivative, or a pharmaceutical salt thereof having PDE5A-inhibitory activity. For example, vardenafil analogs or derivatives having a formula:

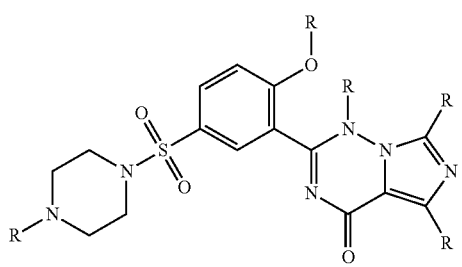

where R is hydrogen or a $C_1$-$C_6$ branched or straight chain alkyl group and where the vardenafil analogs or derivatives have PDE5A-inhibitory activity are contemplated.

The pharmaceutical composition disclosed herein may be delivered via a variety of routes. Typical delivery routes include oral administration, transdermal (e.g., via a dosed patch), intranasal, intravaginal, and intrarectal routes. Other routes include parenteral administration (e.g., intradermal, intramuscular or subcutaneous delivery). The pharmaceutical composition also may be formulated for intranasal or pulmonary delivery. Formulations of the pharmaceutical compositions may include liquid formulations (e.g., for oral, nasal, anal, vaginal, etc. administration, including suspensions, syrups or elixirs) and preparations for parenteral, subcutaneous, intradermal, intramuscular or intravenous administration (e.g., injectable administration) such as sterile suspensions or emulsions.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

Compositions can be formulated in a unit dosage form, for example, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions may be conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

As one skilled in the art will also appreciate, the formulation can be prepared with materials (e.g., actives excipients, carriers, diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Illustrative Embodiments

The following list of embodiments is illustrative and is not intended to limit the scope of the claimed subject matter.

Embodiment 1. A method for treating muscular dystrophy in a patient, the method comprising administering an effective amount of sildenafil, a sildenafil analog, a sildenafil derivative, or a pharmaceutical salt thereof having phosphodiesterase type 5A inhibitory activity to the patient.

Embodiment 2. The method of embodiment 1, comprising administering sildenafil citrate to the patient.

Embodiment 3. The method of embodiment 1 or 2 for treating DMD; BMD; CMD/LGMD (e.g., muscle diseases associated with mutations in the protein O-mannosyltransferase 1 gene (POMT1), the protein O-mannosyltransferase 2 gene (POMT2), the protein O-mannose beta-1,2-N-acetylglucosaminyltransferase gene (POMGnT1), or the fukutin gene (FKTN)); LGMD-2A; LGMD-2B; LGMD-2D; LGMD-2E; LGMD-2I; muscle diseases associated with mutations in the δ-sarcoglycan gene (SG, including three 2C cases); Ullrich congenital muscular dystrophy (UCMD); congenital merosin-deficient, 1A (MDC1A) muscular dystrophy; myositis; autophagic vacuolar myopathy; myopathies not associated with a specific protein deficiency; myotonic dystrophy type 1(DM1); spinal muscular atrophy (SMA); critical care myopathy cases; Pompe disease; or sarcoidosis.

Embodiment 4. The method of embodiment 1 or 2 for treating DMD.

Embodiment 5. The method of embodiment 1 or 2 for treating BMD.

Embodiment 6. The method of any of embodiments 1-5, wherein the effective amount is effective for reducing fatigue in the patient.

Embodiment 7. The method of any of embodiments 1-6, wherein the effective amount is effective for reducing activity-induced fatigue in the patient.

Embodiment 8. The method of any of embodiments 1-7, wherein the effective amount is effective for reducing fatigue in the patient after exercise and the effective amount is administered to the patient prior to exercise.

Embodiment 9. The method of embodiment 8, wherein the exercise is mild exercise.

Embodiment 10. The method of any of embodiments 1-9 for reducing muscle fatigue.

Embodiment 11. The method of any of embodiments 1-10, wherein the effective amount is effective for reducing muscle damage in the patient (e.g., as assessed by measuring creatine kinase levels in the patient's serum after exercise, and optionally mild exercise).

Embodiment 12. The method of any of embodiments 1-11, wherein the sildenafil, the sildenafil analog, the sildenafil derivative, or the pharmaceutical salt thereof is administered daily at a dose of about 10-30 mg/kg body mass.

Embodiment 13. The method of any of embodiments 1-12, wherein the patient is a post-menopausal female.

Embodiment 14. The method of any of embodiments 1-13, wherein the patient has HIV disease.

Embodiment 15. The method of any of embodiments 1-14, wherein the patient has cancer.

Embodiment 16. The method of any of embodiments 1-15, wherein the patient has muscle weakness associated with aging.

Embodiment 17. A method for reducing fatigue in a patient having a muscle disease, the method comprising administering an effective amount of a phosphodiesterase type 5A inhibitor or a pharmaceutical salt thereof to the patient.

Embodiment 18. The method of embodiment 17 for reducing activity-induced fatigue in the patient.

Embodiment 19. The method of embodiment 17 for reducing fatigue in the patient after exercise, wherein the phosphodiesterase type 5A inhibitor or the pharmaceutical salt thereof is administered to the patient prior to exercise.

Embodiment 20. The method of embodiment 19, wherein the exercise is mild exercise.

Embodiment 21. The method of any of embodiments 17-20 for reducing muscle fatigue.

Embodiment 22. The method of any of embodiments 17-21, wherein the patient has or is at risk for acquiring DMD; BMD; CMD/LGMD (e.g., muscle diseases associated with mutations in the protein O-mannosyltransferase 1 gene (POMT1), the protein O-mannosyltransferase 2 gene (POMT2), the protein O-mannose beta-1,2-N-acetylglucosaminyltransferase gene (POMGnT1), or the fukutin gene (FKTN)); LGMD-2A; LGMD-2B; LGMD-2D; LGMD-2E; LGMD-2I; muscle diseases associated with mutations in the δ-sarcoglycan gene (SG, including three 2C cases); Ullrich congenital muscular dystrophy (UCMD); congenital merosin-deficient, 1A (MDC1A) muscular dystrophy; myositis; autophagic vacuolar myopathy; myopathies not associated with a specific protein deficiency; myotonic dystrophy type 1(DM1); spinal muscular atrophy (SMA); critical care myopathy cases; Pompe disease; or sarcoidosis.

Embodiment 23. The method of embodiment 17, wherein the muscle disease is muscular dystrophy.

Embodiment 24. The method of embodiment 23, wherein the patient has Duchenne muscular dystrophy.

Embodiment 25. The method of embodiment 23, wherein the patient has Becker muscular dystrophy.

Embodiment 26. The method of any of embodiments 17-25, wherein the patient is a post-menopausal female.

Embodiment 27. The method of any of embodiments 17-26, wherein the patient has HIV disease.

Embodiment 28. The method of any of embodiments 17-27, wherein the patient has cancer.

Embodiment 29. The method of any of embodiments 17-28, wherein the patient has muscle weakness associated with aging.

Embodiment 30. The method of any of embodiments 17-29, wherein the phosphodiesterase type 5A inhibitor is sildenafil, a sildenafil analog, a sildenafil derivative, or a pharmaceutical salt thereof.

Embodiment 31. The method of any of embodiments 17-30, wherein the phosphodiesterase type 5A inhibitor is sildenafil citrate.

Embodiment 32. The method of any of embodiments 17-29, wherein the phosphodiesterase type 5A inhibitor is tadalafil, a tadalafil analog, a tadalafil derivative, a tadalafil isomer, or a pharmaceutical salt thereof.

Embodiment 33. The method of any of embodiments 17-32, wherein the phosphodiesterase type 5A inhibitor is administered at a dosage of about 10-30 mg/kg body mass.

Embodiment 34. The method of any of embodiments 17-33, wherein the phosphodiesterase type 5A inhibitor is administered no later than about 24 hours before exercise.

Embodiment 35. The method of any of embodiments 17-33, wherein the phosphodiesterase type 5A inhibitor is administered no later than about 6 hours before exercise.

Embodiment 36. A method for treating, preventing, or reducing the likelihood of edema occurring after exercise in a patient having a muscle disease, the method comprising administering to the patient an effective amount of sildenafil, a sildenafil analog, a sildenafil derivative, or a pharmaceutical salt thereof having phosphodiesterase type 5A inhibitory activity.

Embodiment 37. The method of embodiment 36, wherein the sildenafil, the sildenafil analog, the sildenafil derivative, or the pharmaceutical salt thereof is administered to the patient prior to exercise.

Embodiment 38. The method of embodiment 36 or 37, wherein the exercise is mild exercise.

Embodiment 39. The method of any of embodiments 36-38, wherein the patient has or is at risk for acquiring a muscle disease selected from a group consisting of DMD, BMD, CMD/LGMD, LGMD-2A, LGMD-2B, LGMD-2D, LGMD-2E, LGMD-2I, muscle diseases associated with mutations in the δ-sarcoglycan gene, Ullrich congenital muscular dystrophy (UCMD), congenital merosin-deficient 1A (MDC1A) muscular dystrophy, myositis, autophagic vacuolar myopathy, myopathies not associated with a specific protein deficiency, myotonic dystrophy type 1(DM1), spinal muscular atrophy (SMA), critical care myopathy cases, Pompe disease, or sarcoidosis.

Embodiment 40. The method of embodiment 39, wherein the patient has muscular dystrophy.

Embodiment 41. The method of embodiment 40, wherein the patient has Duchenne muscular dystrophy.

Embodiment 42. The method of embodiment 40, wherein the patient has Becker muscular dystrophy.

Embodiment 43. The method of any of embodiments 36-42 comprising administering an effective amount of sildenafil citrate.

EXAMPLES

The following Examples are illustrative and are not intended to limit the scope of the claimed subject matter.

Example 1

Sildenafil to Treat Muscle Disease

Summary

Using an exercise/activity assay for screening for drugs that would enhance activity and prevent creatine kinase increases following exercise, sildenafil citrate (Viagra®, Pfizer) and related PDE5A inhibitors have been identified as therapeutic agents for the treatment of various muscle diseases. Nitric oxide (NO) drugs and in particular, sildenafil, an FDA-approved drug, was found to be very effective at preventing the loss of activity following exercise.

Description

Using a novel exercise/activity assay that can be used to screen drugs for treating muscle disease, sildenafil was identified as a therapeutic agent for preventing muscle fatigue and damage following exercise in neuromuscular diseases. In the assay, mice are initially placed in an activity cage for thirty minutes, and different activity measurements are measured and monitored during this time frame. The mice are then bled to measure serum creatine kinase (CK) levels and then the mice are injected with Evans Blue Dye. Several. Twenty-four hours later, the mice are then subject to a ten minute exercise protocol on a treadmill with a fifteen degree downhill incline at fifteen meters per minute. Following the exercise protocol, the mice are placed back in the activity cage, and post-exercise activity is measured for thirty minutes. Two hours after the exercise protocol ends, the mice are bled for serum CK, and additional analysis can be done later for muscle histology and Evans Blue uptake.

Normal mice have low serum CK values before and after exercise and have normal activity before and after exercise. In some cases there is a slight increase of serum CK and a slight decrease in activity. Mice with neuromuscular disease, in particular the Dystrophin glycoprotein complex (DGC) models tested (dystrophin deficient mice, α-, β-, δ-sarcoglycan deficient mice), have moderate serum CK values before exercise and extremely high serum CK values after exercise. In addition, before exercise these mice seem to have normal activity; however, after exercise there is a dramatic reduction in all measures of activity.

Administration of sildenafil prior to exercise dramatically increased post-exercise activity in nNOS-null mice as well as DGC models of muscular dystrophy. Interestingly, although the mice were subjected to eccentric contractions, sildenafil was able to prevent an increase in serum CK and Evans Blue Dye uptake in muscle following exercise.

Because mice have a 100-fold higher rate of metabolism of sildenafil than in humans, for acute sildenafil citrate (Viagra®, Pfizer) treatment, sildenafil was given orally by mixing the drug into water softened rodent gruel (2019 Teklad global 19% protein rodent chow; 4-6 g/day) at a concentration of 100-300 mg/kg/d. Mice were also supplemented with normal chow (7013 NIH-31 modified sterilizable diet) to ensure the mice were fed ad libitum. Treated mice were given treated food the day before and the morning of the exercise study.

Example 2

Pharmacological Screen to Identify Compounds that Facilitate NO-signaling in Muscle with Deficient nNOS Localization and/or Activity Summary A pharmacological screen has been developed in the form of an exercise-activity assay to identify compounds that facilitate nitric oxide (NO) signaling in muscle with mislocalized neuronal nitric oxide synthase (nNOS) to prevent the exaggerated exercised-induced fatigue that results from this mislocalization. Examples of a class of pharmaceuticals identified with this assay are sildenafil citrate (Viagra®, Pfizer) and tadalafil (Clalis®, Eli Lilly). Related phosphodiesterase 5A (PDE5A) inhibitor compounds also may be utilized.

Description

In the assay, mdx mice (which are a mouse model for Duchenne muscular dystrophy) were treated with various drug classes. Subsequently, exercise-activity was measured using this assay to screen for drugs that enhanced post-exercise activity to near normal levels and prevented serum creatine kinase (CK) increases following exercise (an index of muscle damage). PDE5A inhibitors like sildenafil and tadalafil are approved drugs that are very effective at preventing the exercise-induced fatigue.

The exercise-activity assay will be useful for any physiological condition in which there is a mislocalization of nNOS from the sarcolemma or in which NO bioavailability or signaling is affected such as in muscular dystrophies and myopathies, also for muscle weakness with aging. In addition, this assay will be useful in studying exercise-induced fatigue involved with post-menopausal females, HIV disease or cancer.

The use of this invention will quickly identify compounds, in whole animal models, for treating the exaggerated fatigue response to mild exercise. For example, sildenafil and tadalafil are approved drugs and thus can be used without delay in patients with muscular dystrophy, in post-menopausal females, or in cancer patients.

Although a large number of muscle disease genes have been discovered, there is still no efficient treatment for muscle diseases such as muscle dystrophy. More importantly, activity-induced fatigue is a distinct neuromuscular disease symptom that is a major determinant of quality of life in these patients, and only recently has the molecular basis of this form of fatigue been identified.

Most mouse muscle fatigue measurements are done in vitro (ex vivo) and measure the fatigability of muscle (strength or contractility) or the innate ability of a muscle fiber to withstand fatigue in the absence of its blood supply. The present assay was designed as an in vivo assessment of exercise-induced fatigue in live, non-anaesthetized mice.

The pharmacological screen utilizes an exercise-activity assay to identify compounds that facilitate NO signaling in muscle having mislocalized nNOS. In the assay, mice are initially placed in an activity cage for thirty minutes to measure pre-exercise activity, and different activity measurements are measured and monitored during this time frame. The mice are then bled to measure pre-exercise serum creatine kinase (CK) levels and then the mice are injected with Evans Blue Dye. The next day, mice are subjected to an exercise protocol on a treadmill with a fifteen degree downhill incline which entails: a warm up treadmill walk of 3 minutes at 3 mpm, then a treadmill run for 10 minutes at 15 mpm. Following the exercise protocol, the mice are placed back in the activity cage, and post-exercise activity is measured for thirty minutes. Two hours post-exercise, the mice are bled for serum CK, and additional analysis may be performed later to assess muscle histology, Evans Blue uptake, and biochemistry.

Normal mice have relatively low serum CK values and normal activity before and after exercise. In some cases there is a slight increase of serum CK and a slight decrease in activity. Mice with neuromuscular disease, in particular, a deficiency in one of the components of the dystrophin glycoprotein complex (DGC) (models tested so far are dystrophin deficient mice, and α-, β-, or δ-sarcoglycan deficient mice), have moderately high serum CK values before exercise and extremely high serum CK values after exercise. In addition, before exercise they seem to have normal activity and are indistinguishable from their wild-type counterparts; however, after exercise there is a dramatic reduction in all measures of activity.

Example of drug class identified with this assay included different pharmaceutical vasodilators which were administered to mice either by intraperitoneal injection, intravenous injection, or orally by gavage or mixed with food. Of these pharmaceutical classes of drugs, only PDE5A inhibitors were able to dramatically increase post-exercise activity in DGC models of muscular dystrophy. Interestingly, although the mice were subjected to eccentric contractions, specific PDE5A inhibitor were able to prevent an increase in serum CK and Evans Blue Dye uptake in muscle following exercise.

Initial data have identified several NO drugs that appear to be effective in preventing a decrease in activity following exercise and preventing an increase in serum CK. Additional research is being done on the testing of various NO drugs in several models of muscular dystrophy.

Example 3

Sarcolemma-localized nNOS is Required to Maintain Activity After Mild Exercise

Reference is made to Kobayashi et al., "Sarcolemma-localized nNOS is Required to Maintain Activity After Mild Exercise," Nature Letter, published on-line October 26, 2008; published in final edited form as Nature. 2008 November 27; 456(7221):511-515; the content of which is incorporated herein by reference in its entirety.

Results and Discussion

To understand the molecular basis of the exercise-induced fatigue response, genetically-defined mouse models were studied. An integrative in vivo assay was designed to test conscious mice, subjecting the mice to brief low-speed treadmill exercise followed by testing in an open-field activity chamber (see methods). Two dystrophic mouse lines were first assessed: mdx (model for Duchenne Muscular Dystrophy (DMD)) (Radley et al. 2007) and Sgca-null (model for limb-girdle muscular dystrophy type 2D that is deficient for α-sarcoglycan (Sgca)) (Duclos et al. 1998). Activity in the mice was videorecorded either before or after mild exercise. (Video provided as supplementary material in Kobayashi et al. (2008)). In the absence of previous exercise, activity in these mice was observed to be indistinguishable from that of wild-type mice. After a single trial of mild exercise, significant differences were observed. The mdx and Sgca-null mice showed significant reduction in vertical activity.

The drop in the vertical activity among mdx and Sgca-null mice did not correlate with differences in EDL-specific force measurements relative to those taken in C57BL/6 mice before exercise (FIG. 1c). Moreover, Sgca-null mice do not develop brain, heart nor vascular pathology (Ozawa et al. 2005) and have muscle-force values similar to those of control mice (Consolino et al. 2005). Therefore, neither cardiac deficiency nor an inability to produce force was the cause of the post-exercise inactivity in the Sgca-null mice. Since inflammation is a feature of dystrophinopathy (Radley et al. 2007), chronic fatigue is associated with muscle pain, and chronic pain is associated with fatigue (Yokoyama et al. 2007), mdx mice were treated with either deflazacort or ibuprofen. However, neither treatment resulted in improved post-exercise activity (FIG. 1d) suggesting that the inactivity that occurs immediately after mild exercise in mdx mice was not due to inflammation or pain. Overall, the results of the exercise-activity assay implied that the exaggerated fatigue response in these mice was not attributable to cardiac deficiency, lack of muscle force, inflammation, or pain.

Figure 5:
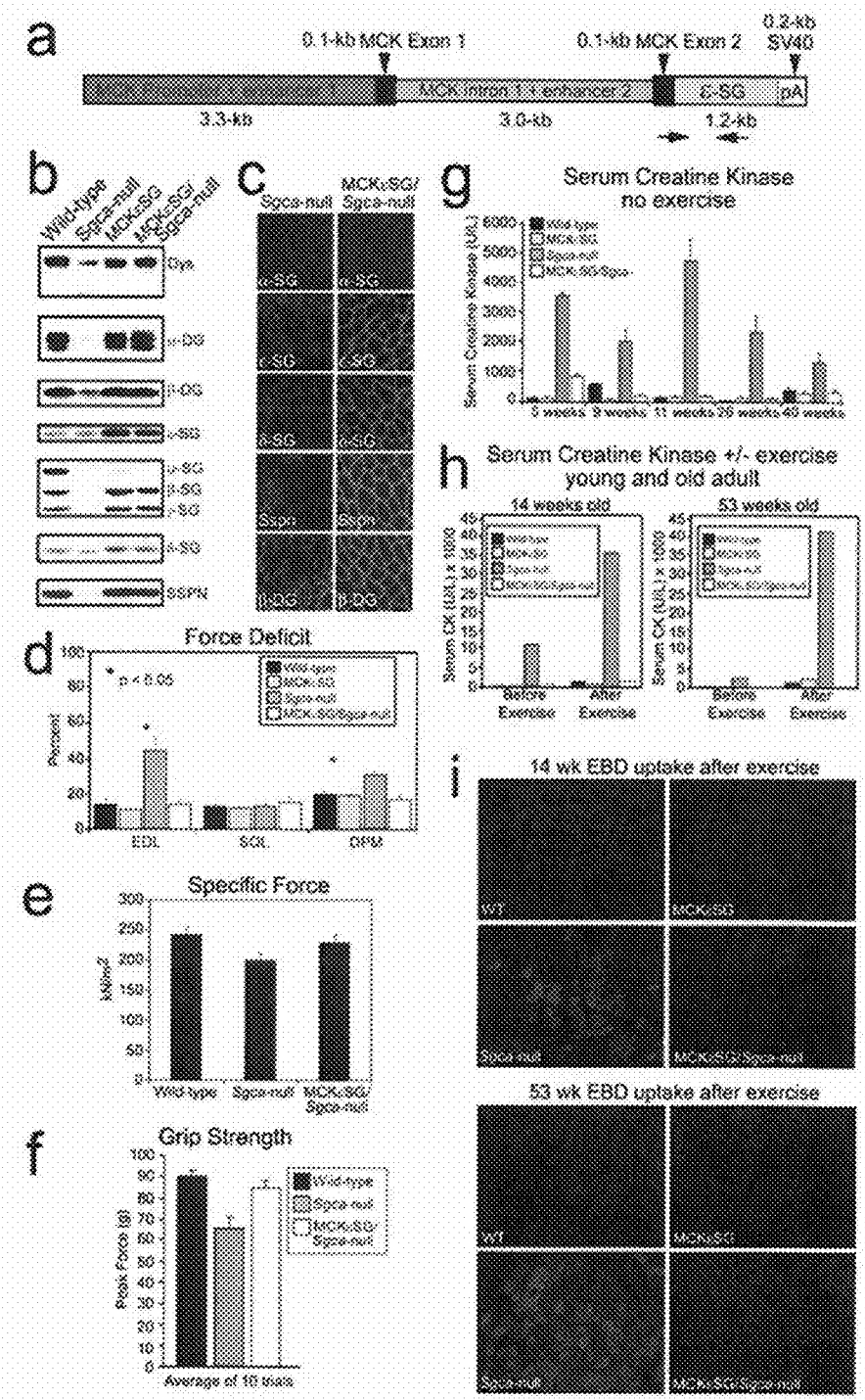
FIG. 5. illustrates that overexpression of ε-sarcoglycan in striated muscle of Sgca-null mice restores the DGC and normal muscle function: a, The mouse muscle creatine kinase promoter was used to drive transgenic expression of a human ε-sarcoglycan transgene in mice. Arrows indicate positions of primers used for genotyping. b, Immunoblotting for structural DGC components showed a complete recovery of the DGC in crude muscle membrane preparations from Sgca-null mice in which the ε-sarcoglycan transgene was expressed. Littermate wild-type, Sgca-null, and MCKεSG mice were used for a comparison of expression levels. c, Immunofluorescence detection of α-, ε-, δ-sarcoglycan, sarcospan, and β-dystroglycan in littermate 5-week old Sgca-null and MCKεSG/Sgca-null mouse quadriceps showing restoration of the sarcoglycans and sarcospan to the sarcolemma, due to the expression of the ε-sarcoglycan transgene. Detection of β-dystroglycan was used as a control for membrane staining. d, Force deficit measurements of extensor digitorum longus (EDL), soleus, and diaphragm (DPM) muscles. All tests were performed on each of the 4 mouse strains with n=4 for each muscle of each strain. e, In vitro specific force measurements comparing wild-type, Sgca-null and MCKεSG/Sgca-null EDL muscles. f, Whole-mouse-grip strength force measurement comparing wild-type, Sgca-null and MCKεSG/Sgca-null forearm strength. g, Serum CK levels in unexercised mice, measured at different time points up to 40 weeks of age, showed MCKεSG/Sgca-null mice to have low CK levels that were similar to those of their littermate wild-type and MCKεSG controls, and much lower than those of Sgca-null littermate controls. h, Comparison of serum CK levels in 14- and 53-week old littermate wild-type, MCKεSG, Sgca-null, and MCKεSG/Sgca-null mice before and after exercise. i, Images of quadriceps muscle from each genotype, examined for Evans blue dye uptake, which indicates muscle fiber damage. (Error bars are S.E.M.)
Figure 6:
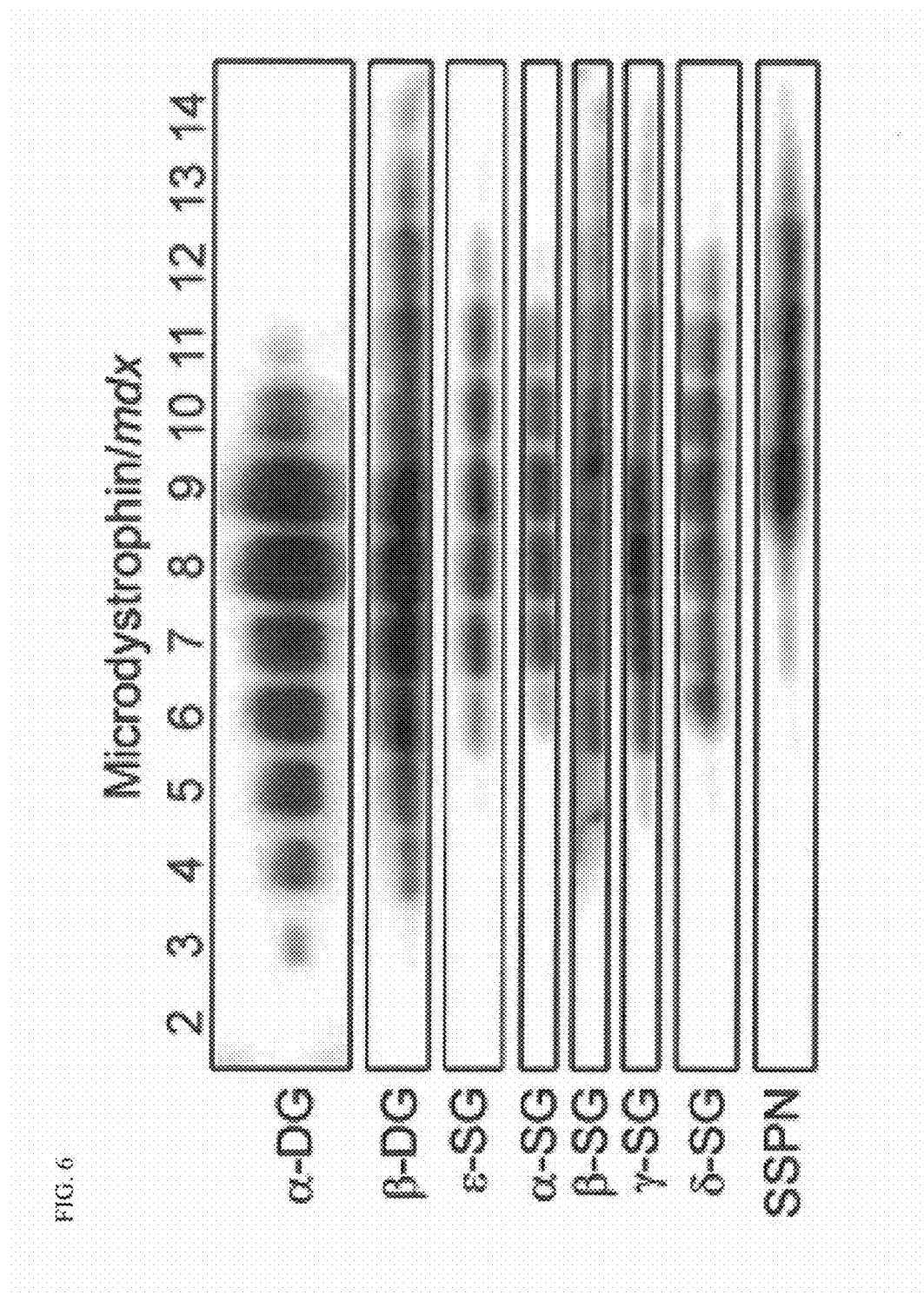
FIG. 6. illustrates that microdystrophin(udys)/mdx skeletal muscle DGC is intact. A sucrose density gradient of skeletal muscle DGC from microdystrophin/mdx mice, showing a structurally intact DGC-, α-, and β-dystroglycan (α-DG and (β-DG), α/ε-sarcoglycan (α/ε-, γ-, and δ-SG), and sarcospan (SSPN). In mdx mice, the DGC structural components are dispersed through the sucrose gradient (Crosbie et al. 1999). Microdystrophin/mdx mice show restoration of the structural DGC proteins to the sarcolemma, with contractility returning to the levels seen in wild-type mice (Harper et al. 2002) but, as shown in FIG. 1 e, without restoration of nNOS to the sarcolemma.

To test if the exercise-induced inactivity in the mdx and Sgca-null mice was due to the genetically determined structural defect in muscle, two mouse models were assayed in which the muscle pathology related to the specific dystrophin glycoprotein complex (DGC) defect is rescued—Microdystrophin/mdx and MCKεSG/Sgca-null. In microdystrophin/mdx mice (model for mild Becker M D (Harper et al. 2002)—the DGC has a mutated but functional dystrophin), microdystrophin is expressed in mdx mouse muscle. In the MCKεSG/Sgca-null mice, ε-sarcoglycan is expressed in mouse muscle that is deficient for Sgca (FIG. 5). Neither rescue strain showed pathological signs of muscular dystrophy, and the skeletal muscle DGC of both was recovered at the biochemical, structural, and functional levels (Harper et al. 2002; and Imamura et al. 2005) and FIGS. 5 and 6).

Despite having a structurally intact skeletal muscle DGC, microdystrophin/mdx mice experience a substantial drop in activity after mild exercise, like their mdx littermates (FIG. 1e). Since Becker MD patients show profound fatigue after light exertion (Phillips et al. 2000), and loss of sarcolemma-localized nNOS serves as a diagnostic indicator of some forms of Becker M D (Torelli et al. 2004), a possible reason for the post-exercise inactivity is a loss of sarcolemma-localized nNOS. To test this possibility, nNOS localization was probed in microdystrophin/mdx skeletal muscle, and found that the DGC generated in this rescue strain failed to recruit nNOS to the sarcolemma (FIG. 1e, inset).

These data are in agreement with recent reports on microdystrophin expression in dystrophin-deficient mouse models (Judge et al. 2006). Moreover, the data suggest that exercise-induce inactivity in the microdystrophin/mdx mice is not directly caused by a structurally defective muscle DGC, and that loss of sarcolemmal nNOS does not negatively affect muscle contractility. Thus, sarcolemmal nNOS appears to act at the level of post-exercise activity.

In contrast to the microdystrophin/mdx mice, MCKεSG/Sgca-null mice have structurally intact DGC in the brain and the vasculature, but express ε-sarcoglycan instead of Sgca in the DGC of muscle. The exercise-activity assay showed that post-exercise activity in the MCKεSG/Sgca-null mice was substantially decreased relative to that in C57BL/6 mice, but similar to that in Sgca-null and mdx mice (FIG. 1b, 1f). Since the microdystrophin-containing DGC failed to recruit nNOS, suggesting that the MCKεSG/Sgca-null mice would also fail to localize nNOS to the sarcolemma. Indeed, although total nNOS levels in muscle homogenates from MCKεSG/Sgca-null mice were similar to wild-type levels, nNOS from the rescue model failed to co-purify with the ε-sarcoglycan-containing DGC in the membrane preparation (FIG. 1f, inset).

Together, these results are compatible with the exaggerated fatigue response not being directly related to a structurally defective muscle DGC or to muscle weakness, but rather to a failure in the sarcolemmal localization of nNOS.

Figure 7:
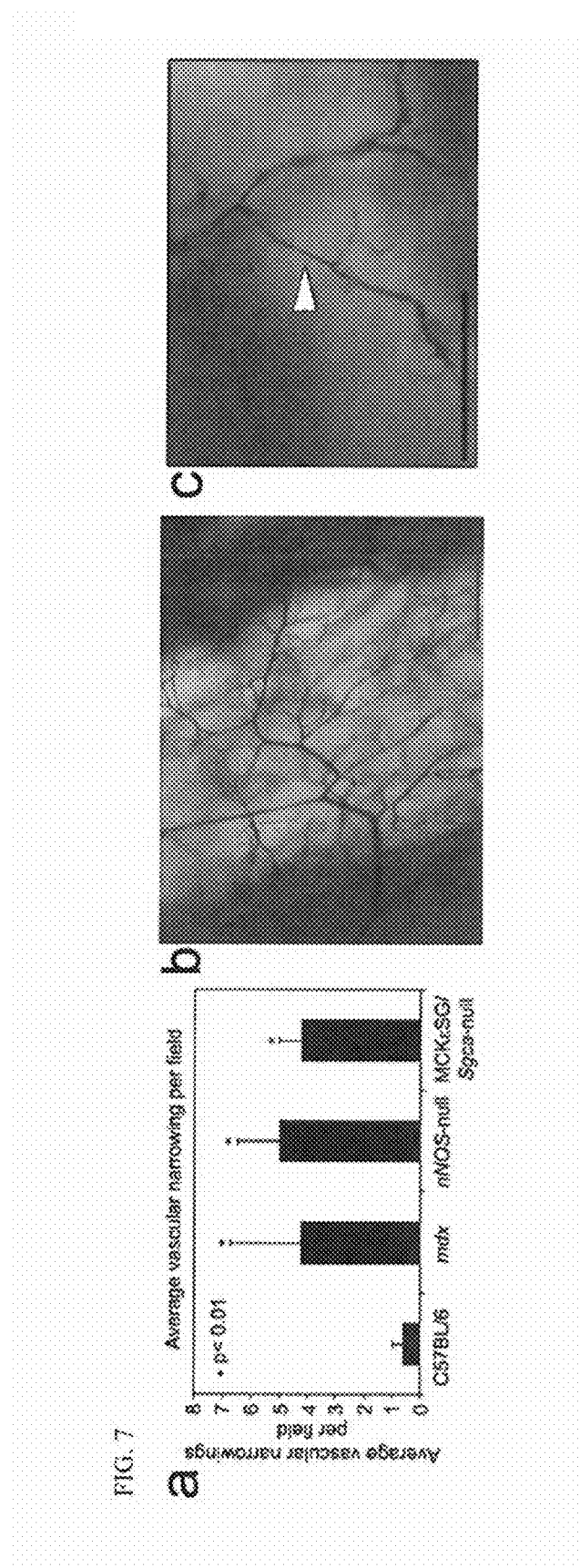
FIG. 7. illustrates vascular narrowings after exercise. a, Skeletal muscle vascular narrowings were averaged per field after exercise and compared to wild-type mice. After exercise, C57BL/6 mice have increased capillary perfusion and little to no vascular narrowings (b) whereas mdx (c), MCKεSG/Sgca-null, and nNOS-null mice do not (see FIGS. 1g and 2c). Each Microfil® image is a representative view of skeletal muscle vessels post-exercise. Arrowhead indicates narrowing. (Error bars=SEM, scale bar=100 μm)

Since sarcolemma localized nNOS is crucial for maintaining vasomodulation to contracting muscles (Thomas et al. 2003), whether communication from skeletal muscle to the local blood supply is deficient after mild exercise was tested by perfusing MCKεSG/Sgca-null mouse arteries pre- or post-exercise with Microfil® and examined the skeletal muscle vasculature (FIG. 1g). Vascular narrowings of varying lengths were identified along the arteries that feed the skeletal muscles only in the post-exercise samples and also noted the lack of perfusion of capillaries. The mdx and microdystrophin/mdx mice likewise showed skeletal muscle vascular narrowings only post-exercise and a lack of perfusion of capillaries (FIG. 7 and data not shown). This phenotype is consistent with inefficient contraction-induced muscle nNOS signaling to local blood vessels. Overall, these data imply that loss of sarcolemma-localized nNOS causes deficient exercise-induced vasomodulation in skeletal muscle, and that these lead to prolonged inactivity post-exercise.

Figure 2:
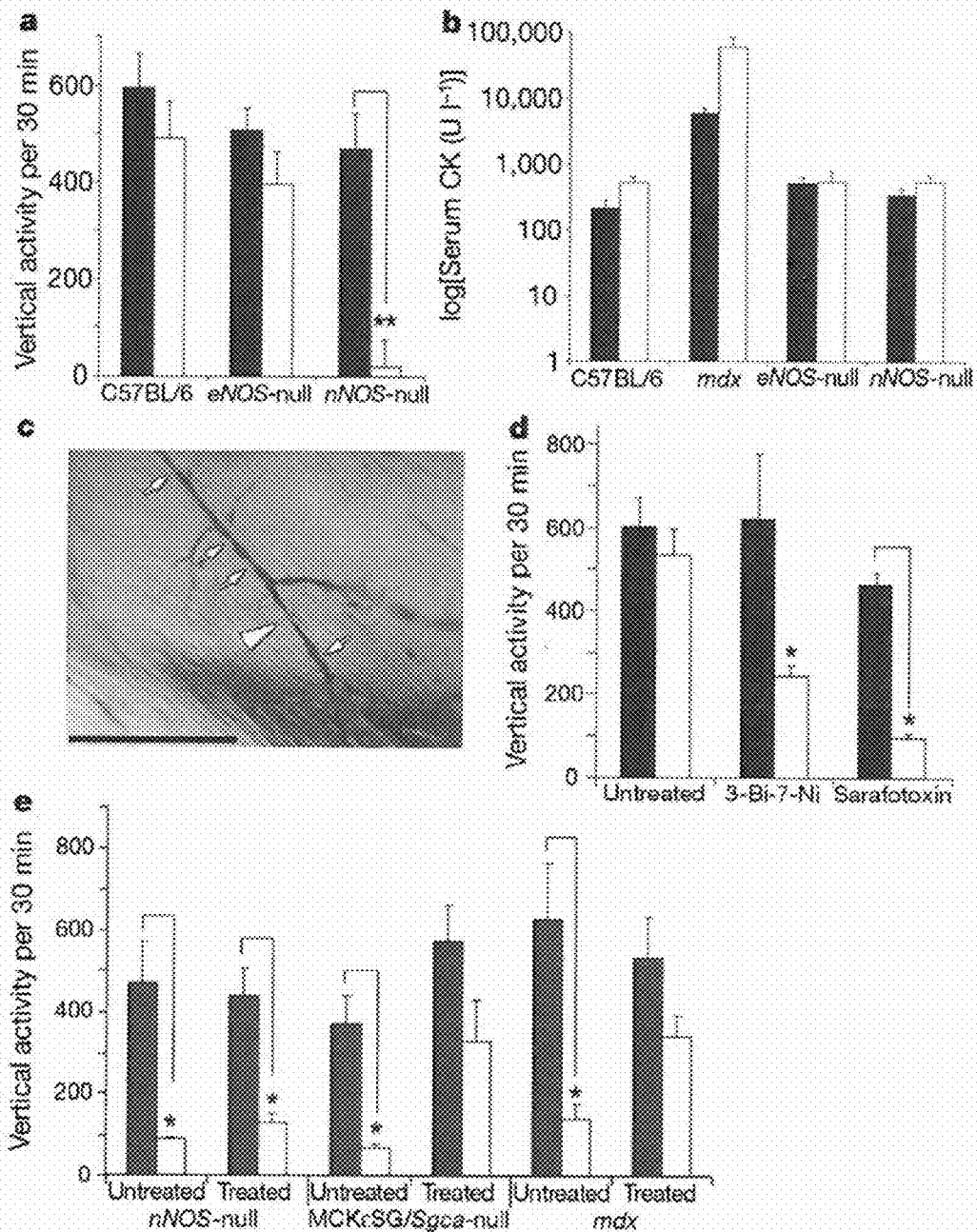
FIG. 2. illustrates that enhancing the cGMP signal resulting from muscle nNOS activation decreases the exaggerated fatigue response to mild exercise.
Figure 8:
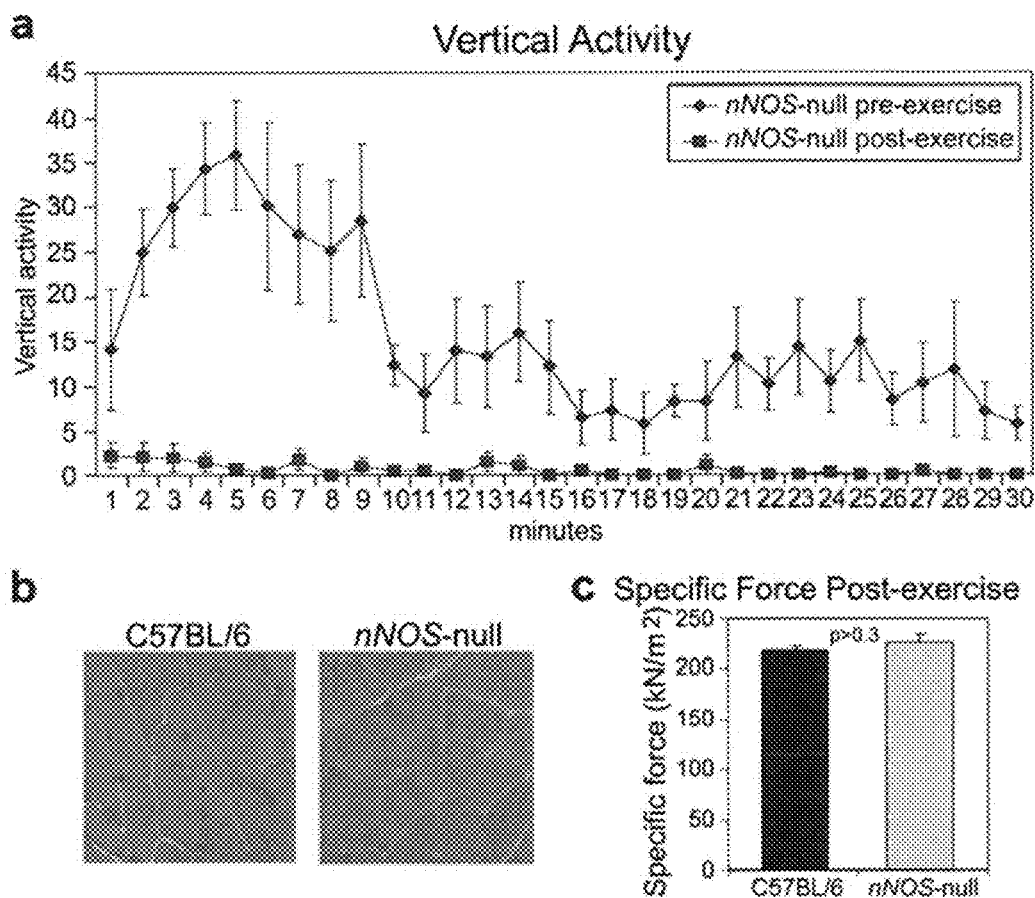
FIG. 8. illustrates the characterization of nNOS-null mice after mild exercise. a, Charting of vertical activity for 30 minutes pre- and post-exercise showing that following a light bout of activity, the vertical activity in nNOS-null mice is extremely low throughout the entire 30 minute analysis. (n=4 for each). (Error bars are S.E.M.). b, Comparison of hematoxylin and eosin staining of quadriceps muscle sections from C57BL/6 and nNOS-null mice (n=6 for each) showing no signs of muscle pathology. c, Contractility comparison measuring specific force after mild exercise in C57BL/6 and nNOS-null EDL muscles (n=5 for each).
Figure 9:
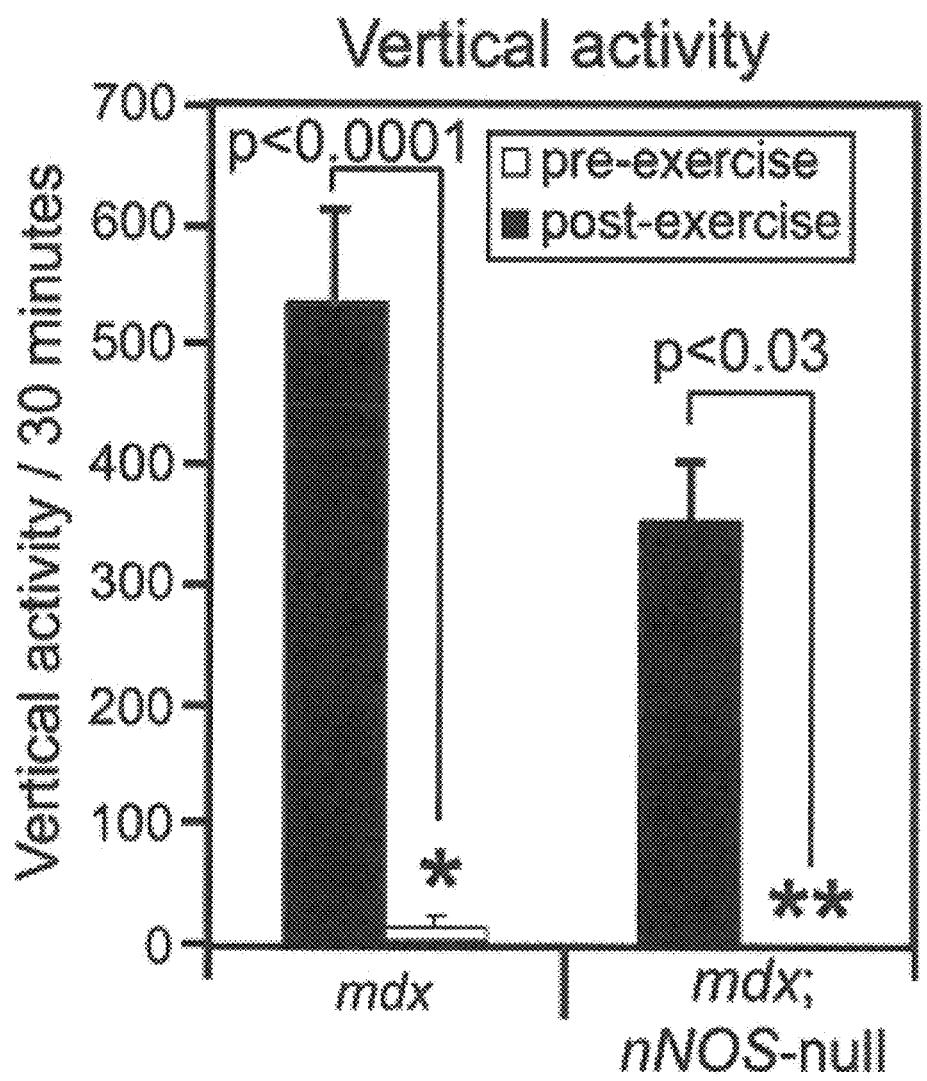
FIG. 9. illustrates the characterization of mdx; nNOS-null mice and vertical activity. The exercise-induced vascular effect suggests that if nNOS were genetically deleted in a muscular dystrophy mouse model, the exercise-induced fatigue would be more significant. This hypothesis was tested by breeding the mdx and nNOS-null mice and analyzing the resulting mdx; nNOS-null mice in the exercise-activity assay. The mdx; nNOS-null mice (n=4) were observed to have even less vertical activity pre- and post-exercise than their mdx littermates (mdx; nNOS$^{+/-}$ or mdx; nNOS$^{+/+}$) (n=7).

To directly examine the contribution of NO generated by eNOS or nNOS to the exaggerated fatigue response, both nNOS- and eNOS-null mice were tested in the exercise-activity assay. Mice deficient for nNOS express normal levels of the DGC components at the sarcolemma and have histologically normal muscle (Chao et al. 1998; Crosbie et al. 1998; and Suzuki et al. 2007). Reports suggest that both mouse strains have defective vasoregulation (Alai et al. 2007; and Huang et al. 1995); however, mdx and nNOS-null mice have a normal α-adrenergic vasoconstrictive response to exercise (Thomas et al. 1998). Vertical pre-exercise activities were similar in eNOS-null, nNOS-null, and C57BL/6 mice, suggesting that the loss of either NOS does not affect mouse activity (FIG. 2a.) Post-exercise, however, nNOS-null vertical activity dropped significantly (FIG. 2a). Serum CK levels pre- and post-exercise for each of the NOS-null mice were similar to those in C57BL/6 mice and low compared to mdx mice (FIG. 2b), and there were no signs of muscle pathology in nNOS-null quadriceps muscle sections (FIG. 8b), suggesting that muscle damage and necrosis were not the causes of the post-exercise inactivity. Whether post-exercise muscle contractility affected the ability of C57BL/6 and nNOS-null skeletal muscle to produce force after mild exercise also was tested. It was found that the specific force of EDL muscles after exercise was not significantly affected in nNOS-null muscle compared to C57BL/6 muscle (FIG. 8c). Since lack of muscle contractility was not causing the inactivity in the nNOS-null mice post-exercise, whether NOS-null mice had post-exercise skeletal muscle vascular narrowings and lack of capillary perfusion similar to those in the dystrophic and rescue mice was assessed. Microfil® perfusion of arteries of NOS-null mouse arteries pre- and post-exercise revealed the lack of capillary perfusion and also the presence of vascular narrowings only in post-exercise nNOS-null skeletal muscle (FIG. 2c). It also was found that treating wild-type mice with either the nNOS-specific inhibitor 3-bromo-7-nitroindazole or the vasoconstrictor sarafotoxin 6c caused post-exercise inactivity (FIG. 2d). These findings suggest that a deficiency of sarcolemma-localized nNOS causes exercise-induced narrowing of the vasculature that feeds active muscles after exercise, thereby promoting prolonged inactivity after mild exercise.

Figure 10:
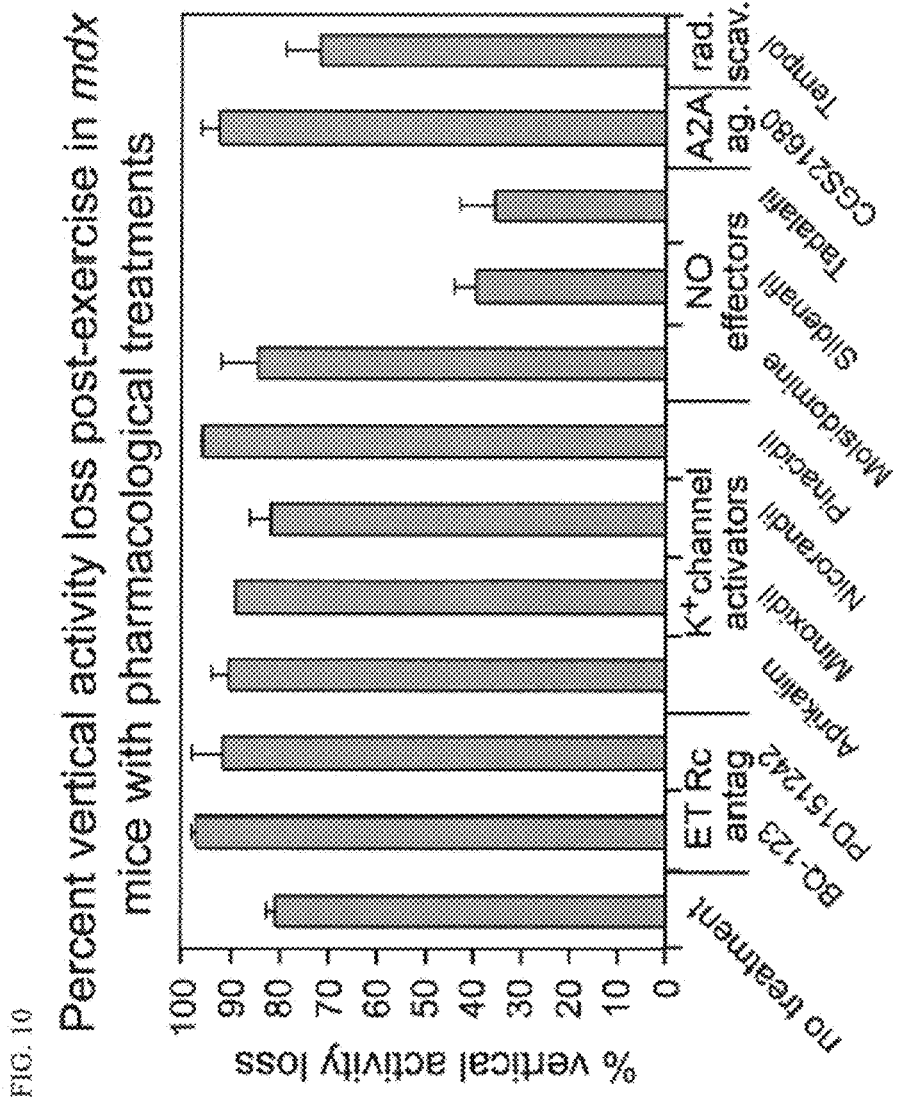
FIG. 10. illustrates percent vertical activity loss post-exercise in mdx mice treated with different classes of pharmacological vasodilators. The loss of post-exercise vertical activity in mdx mice was quantified with and without treatment with various classes of vasodilators. The drugs tested were: $ET_a$ receptor antagonists BQ-123 (0.1 mg/kg, n=3), and PD 151242 (25 ug/mouse, n=4); the potassium channel activators Aprikalim (400uM/mouse, n=4), Minoxidil (0.8 mg/kg, n=2), Nicorandil (0.1 mg/kg, n=2), and Pinacidil (0.8 mg/kg, n=2); the NO level activators Molsidomine (125 ug/mouse, n=4), Sildenafil (300 mg/kg, n=4), and Tadalafil (300 mg/kg, n=6) (note sildenafil and tadalafil affect cGMP levels, downstream of NO); the adenosine 2A receptor antagonist CGS21680 (1 ug/kg, n=2); and the superoxide scavenger Tempol (260 mg/kg, n=4). Untreated control mice for each drug class were pooled, resulting in n=34. Error bars are S.E.M.
Figure 11:
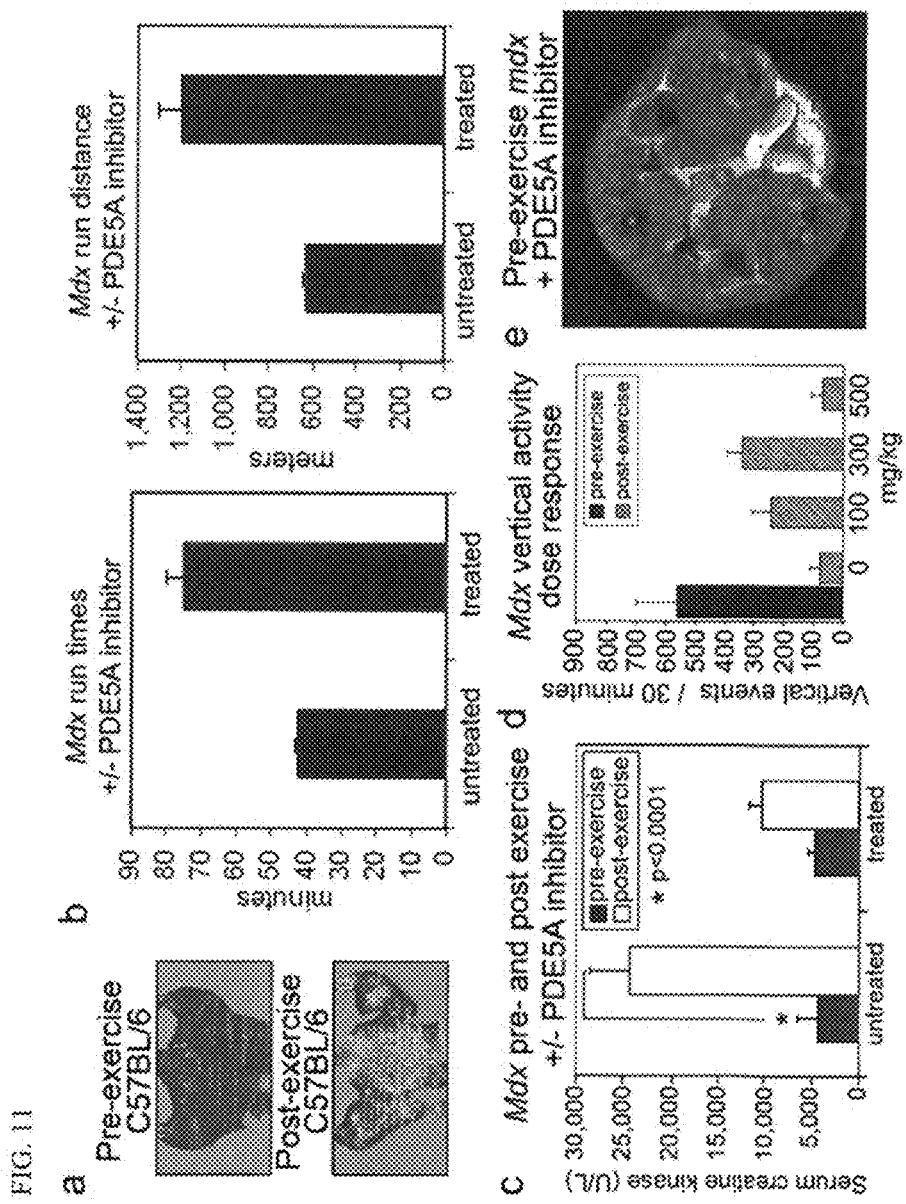
FIG. 11. illustrates the effects of PDE5A inhibitor treatment. a, Representative images of coronal Laser Doppler analysis of blood flow from C57BL/6 mice pre- and post-exercise (compare with FIG. 3a-b), b, Mdx mouse run times and run distances+/−PDE5A inhibitor treatment. c, Mdx pre- and post-exercise serum creatine kinase levels+/−PDE5A inhibitor treatment. (n=6 and error bars are S.E.M.) d, Mdx dose-vertical activity response curve to PDE5A inhibitor. (untreated n=6, 100 mg/kg n=3, 300 mg/kg n=6, 500 mg/kg n=3, error bars are S.E.M.), e, representative axial MRI view of pre-exercised mdx+PDE5A inhibitor.

To test if the vascular effect on post-exercise activity was from NO or downstream of the NO signal, sarcolemmal nNOS signaling for reducing vasoconstriction was bypassed by treating mdx mice with a panel of pharmacological agents that promote vasodilation; it was found that the exaggerated fatigue response was alleviated only by phosphodiesterase (PDE) 5A inhibitor treatment (FIG. 10), suggesting that the fatigue observed depends on cGMP, which acts downstream of NO production. Interestingly, PDE activity in mdx mice is 2-6× higher than in C57BL/10 mice (Bloom et al. 2005), consistent with the elevated PDE activity in human muscular disorders (Asai et al. 2007; Bloom et al. 2005; and Bloom et al. 2002). nNOS-null, MCKεSG/Sgca-null, and mdx mice were treated with PDE5A inhibitors and tested in the exercise-activity assay. It was found that the treated MCKεSG/Sgca-null and mdx mice showed an increase in post-exercise activity (FIG. 2e) and (FIG. 11a-d). Since PDE5A inhibition had no effect on activity before exercise, the results suggest that PDE5A inhibition is alleviating the exaggerated fatigue response by enhancing the cGMP signal produced by contraction-induced nNOS stimulation. Although downstream effectors of cGMP are numerous and divergent (Kass et al. 2007), the half-life of cGMP can be affected by the activity of PDE5A. The data suggest that the elevated PDE activity in mdx mouse extracts could be PDE5A activity and that PDE activity could also be elevated in the rescue mouse models tested.

Figure 3:
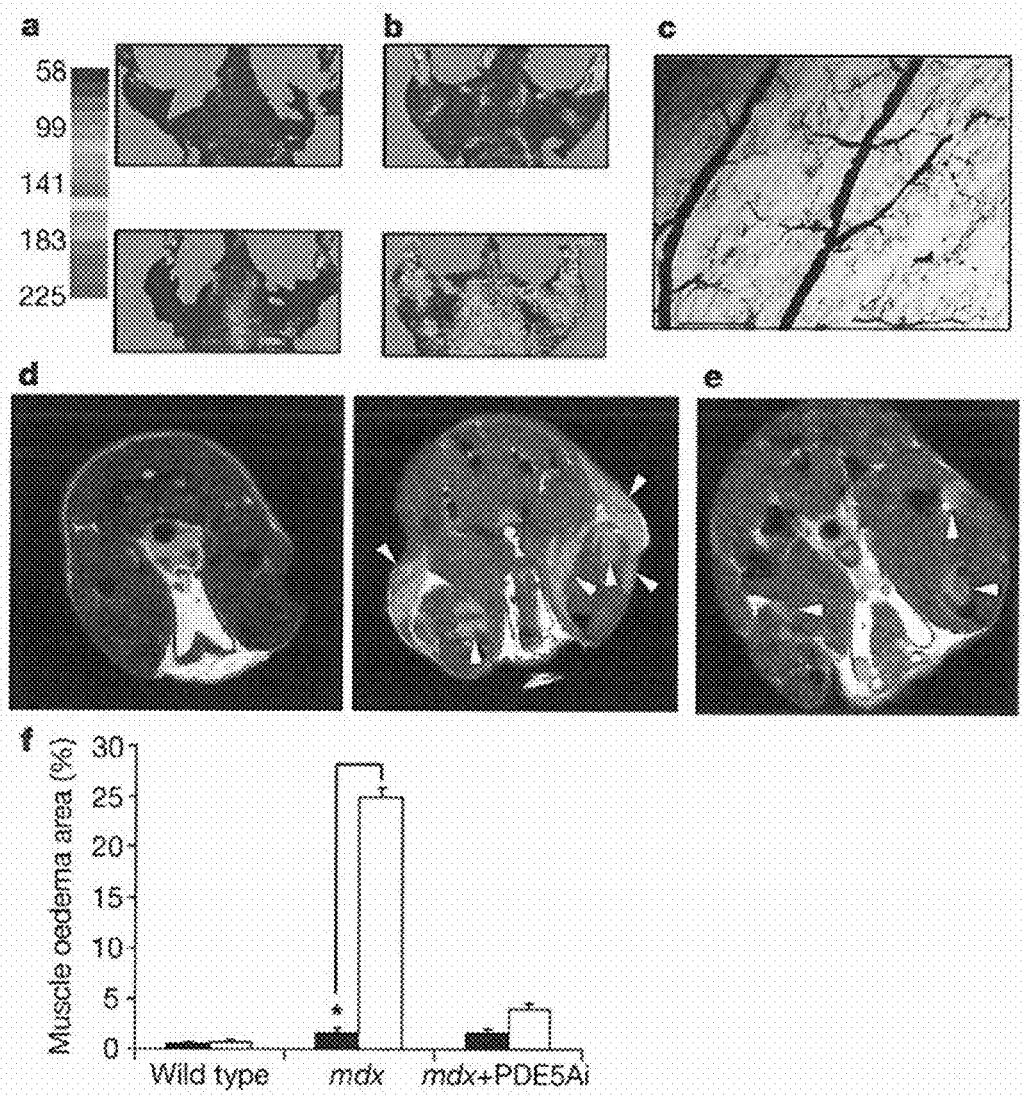
FIG. 3. illustrates that PDE5A inhibitor treatment improves exercised-induced vasomodulation and reduces exercise-induced edema in mdx mice.
Figure 4:
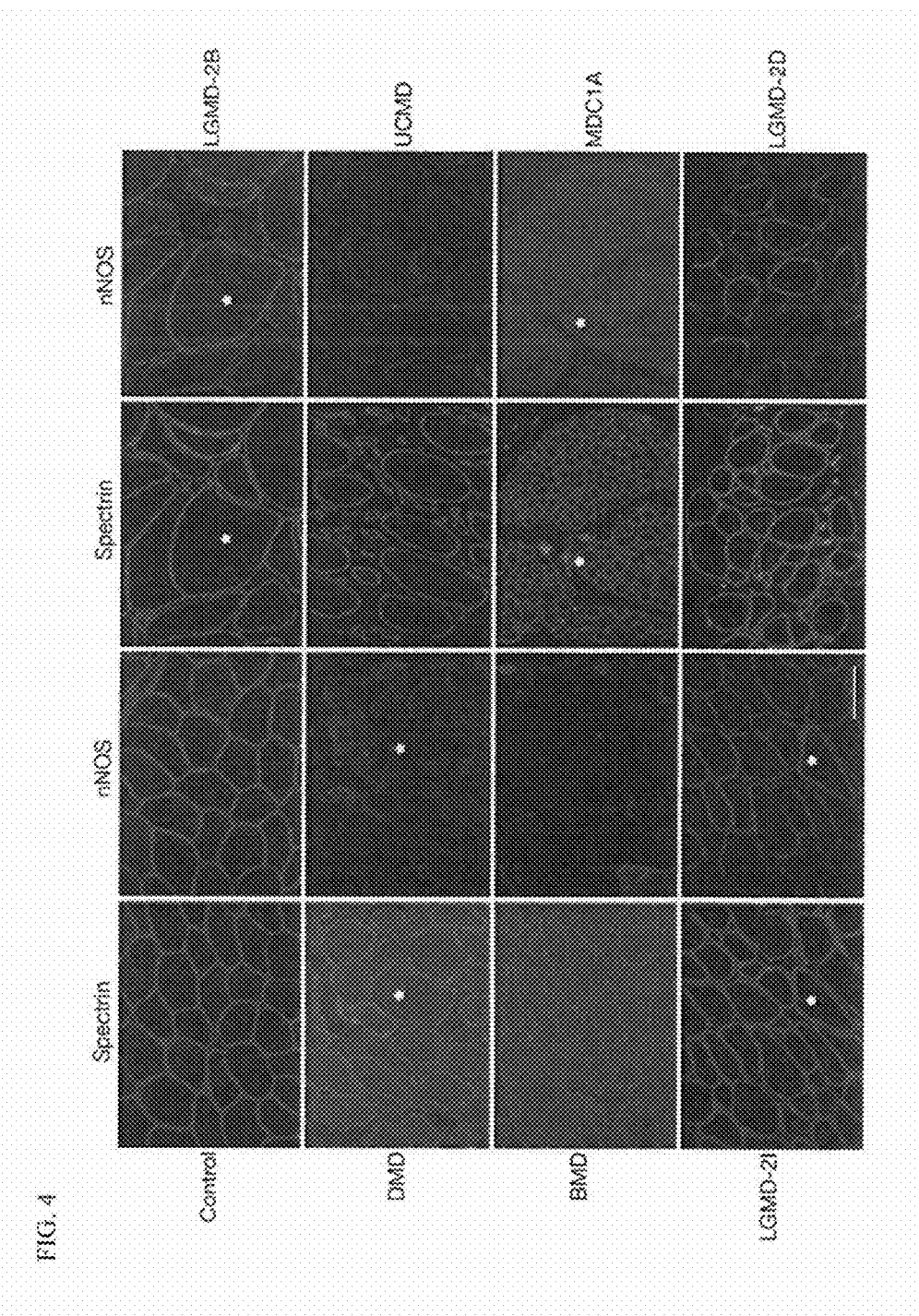
FIG. 4. illustrates that nNOS is reduced in human muscle diseases.
Figure 12:
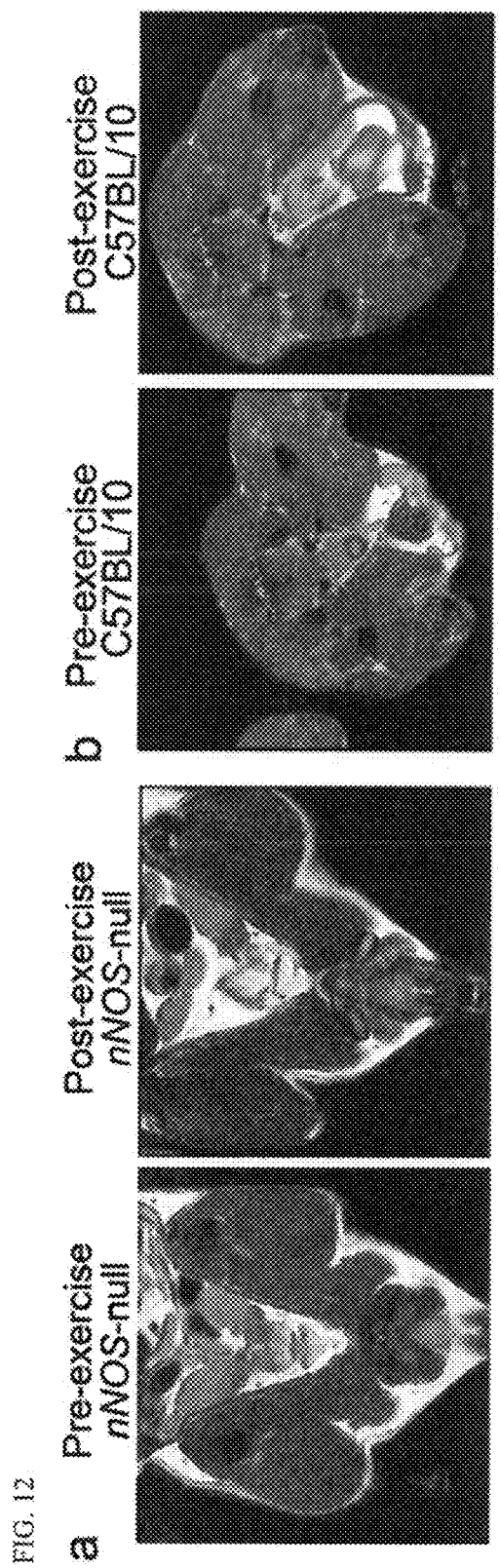
FIG. 12. illustrates the lack of edema pre- and post-exercise in representative MRI views. a, Coronal views of nNOS-null hind-legs pre- and post-exercise (n=3), b, Axial views of C57BL/10 hind-legs (n=3) (0.70%+/−0.50) (Compare to FIG. 3d-e).
Figure 13:
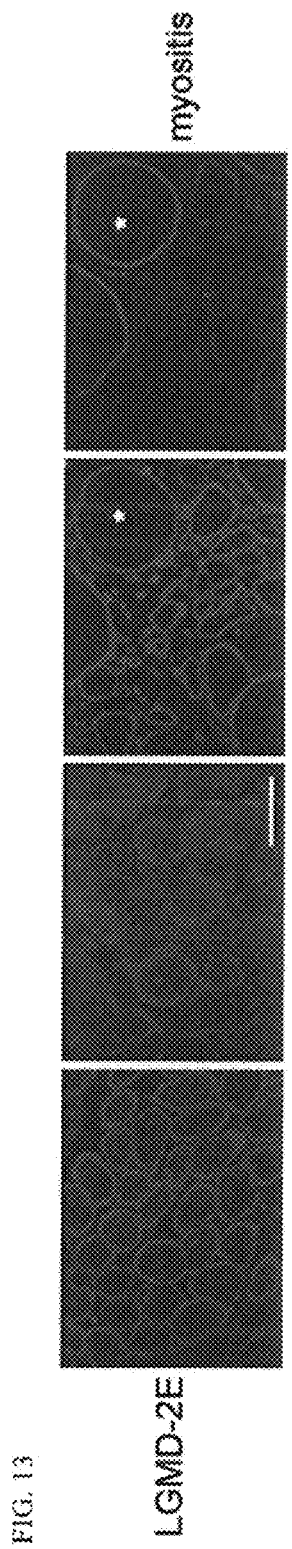
FIG. 13. illustrates that nNOS is reduced in human muscle diseases. Additional example of a limb-girdle muscular dystrophy (LGMD-2E) and a non-dystrophic myopathy like polymyositis (myositis). Asterisks mark the same muscle fiber in some of the adjacent panels. (Compare to FIG. 4) (Scale bar=100 um).

The data suggest that the local resistance of arterioles that perfuse sarcolemmal nNOS-deficient muscles increases during exercise and that the lack of activity after mild exercise will lead to muscle edema. Blood flow pre- and post-exercise was examined with Laser Doppler imaging. It was found that blood flow in mdx mice failed to increase as it did in C57BL/6 mice (FIG. 3a) and (FIG. 11a), but that treatment of mdx mice with a PDE5A inhibitor alleviated this defect (FIG. 3b) and increased muscle capillary perfusion (FIG. 3c). Given that insufficient relief of local vasoconstriction in active muscles can lead to muscle edema (Persson et al. 2003), and that boys afflicted with DMD show muscle edema (Marden et al. 2005), changes in water compartmentalization and dynamics in the hind-leg muscles of nNOS-nullm, C57BL/10 and mdx mice were assessed before and after exercise using spin-spin relaxation time (T2)-magnetic resonance imaging (MRI). The nNOS-null mice did not have muscle damage or loss of contractility after exercise (FIG. 2b and FIG. 8a-c), nor did they have muscle edema (FIG. 12), suggesting that their lack of muscle damage prevents water accumulation in the tissue. Similarly, C57BL/10 mice showed little to no hind-leg muscle edema post-exercise (0.70%+/−0.50) (FIG. 3f and FIG. 12b). However, hind-leg muscles of mdx mice consistently showed significant changes in tissue hydration post-exercise (25.0%+/−2.45) (FIG. 3d, f) that were indicative of exercise-induced muscle edema. The water accumulation observed in the mdx muscles is likely due to a combination of the increased local resistance in the arterioles that feed the active leg muscles and of muscle fiber fragility and damage. It was also consistently found that PDE5A inhibitor treatment significantly reduced exercise-induced muscle edema in mdx mice (3.99%+/−0.82) (FIG. 3e, f). Overall, the data imply that PDE5A inhibitor treatment can relieve the post-exercise inactivity by normalizing PDE activity, thereby allowing the available NO derived from muscle nNOS to signal for cGMP-dependent vasodilation in active muscle; PDE5A inhibitor treatment reduces muscle damage in mdx mice by improving modulation of vascular activity in active muscle, thus preventing muscle edema from exacerbating the muscle damage that occurs during the contraction of dystrophic muscle. Since more than 60% of all patients with neuromuscular disease suffer from severe fatigue (Zwarts et al. 2007), nNOS localization to the sarcolemma was assessed in patient biopsies representing different myopathic disorders (FIG. 4, Supplementary FIG. 13 and Table 1). In most myopathic biopsies assessed, sarcolemma-localized nNOS was either reduced or not detected, implying that many myopathic disorders may share a mechanism that results in severe exercise-induced fatigue. Although increased fatigability inevitably occurs in patients with muscle weakness (Schillings et al. 2007), the mouse data imply that the exercise-induced inactivity is distinct from muscle weakness and that loss of sarcolemma-localized nNOS leads to an exaggerated fatigue response to mild exercise.

In conclusion, the mouse data show that reduced or mislocalized skeletal muscle nNOS exacerbates the fatigue experienced after mild exercise because the normal contraction-induced cGMP-dependent attenuation of local vasoconstriction fails to occur, and that this failure causes vascular narrowing in muscles after exercise. In addition, the mdx mouse data suggest that due to nNOS mislocalization and increased PDE activity (Imamura et al. 2005; Asai et al. 2007; and Bloom et al. 2005), signaling for increased vasodilation to active muscle is deficient, causing muscle edema. This, in turn, contributes to increased muscle damage as well as profound post-exercise debility. Although the exact mechanism that leads to the inactivity after mild exercise has not been reduced to one single beginning and end pathway, the data suggest that contraction-induced cGMP-dependent attenuation of local vasoconstriction is pivotal in this mechanism. These findings could lead to a better understanding of muscle fatigue under other physiological conditions in which muscle nNOS expression, localization, or activity is affected.

Additional Methods

Mouse models. Mouse strains obtained from Jackson Laboratories: C57BL/6, C57BL/10, mdx/C57BL/1 OScSn, nNOS-null, and eNOS-null. Microdystrophin/mdx mice were described previously (Harpert et al. 2002; and Scime et al. 2008). Mice were maintained at the University of Iowa Animal Care Unit in accordance with the institute's animal usage guidelines. It was found that sarcolemmal nNOS in female C57BL/6 mice was less than or equal to that in their male counterparts, depending on the stage of the estrous cycle; since even ovariectomized rats (Fadel et al. 2003) and ovariectomized mice lose sarcolemmal nNOS, only males were tested. All mice were 10 wks of age, unless otherwise stated. Genetically defined mice were randomized between cages to avoid bias and tested blindly. Sgca-null mice (Duclos et al. 1998) were backcrossed to a C57BL/6 background (BC5). MCKεSG/Sgca-null mice were bred with the Sgca-null (BC5) line for 8 generations. EC-SOD mice were from J.D. Crapo's laboratory and expression was driven by the R-actin promoter; these mice were mated with mdx mice for two generations and tested. Dtna-null mice (Duclos et al. 1998) were on a pure C57BL/6 background and were from Drs. R. Mark Grady and J. R. Sanes.

Exercise-activity assay. Mouse housing and exercise-activity rooms were under specific pathogen-free conditions. Since anesthesia causes alterations in blood glucose (Pomplun et al. 2004) as well as in the blood flow to skeletal muscle, the exercise-activity assay was designed without anesthesia. Also, to reduce anxiety, which could potentially lead to increases in blood glucose, and to keep behavioral variables at a minimum, the tested mice were not individually housed. The same handler performed each assay. Mice were activity-monitored using the VersaMax Animal Activity Monitoring System from AccuScan Instruments, Inc. This system uses a grid of invisible infrared light beams that traverse the animal chamber front to back and left to right to monitor the position and movement of the mouse within an X-Y-Z plane. Activity was monitored over a 24 hour cycle to determine their most active time. All mice tested were synchronized to a shifted 12:12-hour light:dark cycle so that at the time of testing, the mice were behaviorally most active. Mice were acclimatized to the activity test room, which was on the same light:dark cycle, for at least an hour. Mice were tested in individual chambers in sets of 4, for 30×1 minute intervals pre- and immediately post-exercise, at the same time every day in the dark, in an isolated room, and with the same handler. Testing equipment was cleaned between each use to reduce mouse reactionary behavioral variables that could alter the results. Data collected was converted to a Microsoft Excel worksheet and all calculations were done within the Excel program. Zone map tracings were created by the AccuScan VersaMap-Zone mapping software where the X and Y plane represent the 2 dimensions of the activity chamber and the dots represent every time the mouse breaks the Z plane, registering vertical activity within the 30 minute time interval.

Animals were mildly exercised using an adjustable variable speed belt treadmill from AccuPacer (AP4M-MGAG, AccuScan Instruments, Inc.), down a 15° grade at 15 mpm for 10 minutes with acclimatization at 3 mpm for 5 minutes.

Antibodies. The nNOS antibody used for immunoblots and immunofluorescence was an affinity purified polyclonal antibody (Crosbie et al. 1998). Antibodies for inflammation included: I-A$^b$ MHC class 11-conjugated to FITC and F4/80conjugated to Alex Fluor® 647, both from Invitrogen. For an atrophy marker, SC-71antibody (ATCC) against myosin heavy chain 2A was used. For hypoxia and oxidative stress, polyclonal antibodies against HIF-1α (R&D Systems) and nitrotyrosine (Upstate), and Hypoxyprobe-1™ Mab1 conjugated to FITC (Chemicon® International) were used.

Immunoblotting analysis. Tissue for immunoblotting came from whole muscle and crude skeletal muscle membranes were prepared as follows: 1-3 g fresh hind leg skeletal muscle was homogenized in 7.5× volumes homogenization buffer (20 mM $Na_4P_2O_7$, 20 mM $NaH_2PO_4$, 1 MM $MgCl_2$, 0.303 M sucrose, 0.5 mM EDTA, pH 7.1 with 5 ug/ml Aprotinin and Leupeptin, 0.5 ug/ml Pepstatin A, 0.23 mM PMSF, 0.64 mM Benzamidine, and 2 uM Calpain inhibitor I and Calpeptin), then centrifuged 14 k×$g_{max}$; supernatants were centrifuged 30 k×$g_{max}$, after which pellets were resuspended in homogenization buffer. Homogenates and crude skeletal muscle membranes were prepared from different mouse models, run on SDS-PAGE and transferred to PVDF (Immobilon-P) transfer membranes for immunoblotting (Durbeej et al. 2000). All immunoblotting was done by chemiluminescent detection using the Alpha Innotech imaging system.

Immunofluorescence analysis. Immunofluorescence staining for nNOS was performed on 7 μm transverse cryo muscle sections as described previously (Crosbie et al. 1998). For patient biopsies, immunofluorescence staining was performed on serial cryosections; both anti-spectrin and anti-nNOS antibodies were purchased from Novocastra. For hypoxia analysis+/−exercise, Hypoxyprobe™ was injected 45 min before exercise.

Microfil® analysis of skeletal muscle vessels. Microfil® MV-130 Red (Flow Tech, Inc) was mixed according to manufacturer's instructions and perfused into the mouse aorta pre-or post-exercise at 100 mm Hg. After polymerization and clearing of skeletal muscles, vessels were imaged.

Tissue blood-flow mapping. The MoorLDI™ system using near infra-red wavelength laser (1.0 mm beam, 2.5 mW) doppler imaging without contrast was used to generate a color coded map of blood flow on a CCD camera at 72×582 pixel resolution. Range was at 20 cm distance in an area 5.1 cm×4.2 cm at 182×152 resolution and scan speed of 4 ms/pixel.

Serum Creatine Kinase Assays. Blood for quantitative, kinetic determination of serum creatine kinase activity was collected either after the pre-exercise activity analysis or 2 hours post-exercise by mouse tail vein bleeds, using a Sarstedt microvette CB 300, from non-anesthetized restrained mice. Red cells were pelleted by centrifugation at 10,000 rpm for 4 minutes and serum was separated, collected and analyzed immediately without freezing. Serum creatine kinase assays were done with an enzyme-coupled assay reagent kit (Stanbio Laboratory) according to manufacturer's instructions. Absorbance at 340 nm was measure every 30 sec for 2 min at 37° C. so that changes in enzyme activity could be calculated. Data were transferred to and calculated in a Microsoft Excel spreadsheet.

Contractile properties. Contractile properties were measured in vitro on extensor digitorum longus (EDL), soleus, or diaphragm muscles strips from C57BL/6, mdx, MCKϵSG/Sgca-null, MCKϵSG, Sgca-null, or nNOS-null mice. Mice were anesthetized by an intraperitoneal injection (I.P.) of 2% avertin (0.0015 ml/g body weight). Supplemental injections were administered to maintain an anesthesia level that prevented responses to tactile stimuli. Intact muscles or DPM strips were removed from each mouse after the mice were euthanized by an overdose of avertin, and the thoracic cavity was opened. Muscles were immersed in an oxygenated bath (95% $O_2$, 5% $CO_2$) that contained Ringer's solution (pH 7.4) at 25° C. For each muscle, one tendon was tied securely with a 4-0 or 6-0 suture to a force transducer (one end), and a servo motor (other end). Using twitches with pulse duration of 0.2 ms, the voltage or current of stimulation was increased to achieve a maximum twitch and then increased slightly. Twitches were then used to adjust the muscle length to the optimum length for force development ($L_0$). The muscle length was set at $L_0$, and EDL muscles were stimulated for 300 ms, and soleus and DPM muscles for 900 ms. Stimulation frequency was increased until the force reached a plateau at maximum isometric tetanic force ($P_0$).

For C57BL/6, mdx, MCKϵSG/Sgca-null, MCKϵSG, Sgca-null mice, the susceptibility to contraction-induced injury was measured during two lengthening contractions, with the contractions separated by a rest interval of 10 s. Each contraction was initiated with the quiescent muscle set at $L_0$, and then a plateau at maximum force was produced by stimulating EDL muscles at a frequency of −150 Hz for 150 ms and soleus and DPM muscles at −120 Hz for 200 ms. While generating maximum force, the muscles were stretched through a 30% strain at a velocity of 1 Lf/s, and then returned to $L_0$. A measurement of $P_0$ was made one minute later. Based on measurements of muscle mass, muscle length, fiber length, and $P_0$, the total fiber cross-sectional area and specific $P_0$(kN/m2) were calculated (Harper et al. 2002; and Lynch et al. 1997). The data were analyzed by an analysis of variance (ANOVA). When the overall F-ratio for the ANOVA was significant, the differences between individual group means were determined by a single t-test. Significance was set a priori at $P<0.05$. Data are expressed as mean±SEM.

Drug treatments. Timing and dosing of deflazacort was based on previous literature on mdx mice treated with deflazacort showing beneficial effects on mdx muscle pathology (Anderson et al. 2003; Anderson et al. 2000; Archer et al. 2006; and St-Pierre et al. 2004). The steroidal anti-inflammatory Deflazacort (Axxora (& Platform) was resuspended in DMSO at 36 mg/ml and then diluted 1:100 in 0.9% saline immediately prior to I.P. injection at 1.5 mg/kg/day for acute and 1.2 mg/kg/day for the 3-week chronic treatment. Timing and dosing of ibuprofen (Alpharma, Inc) was based on veterinary formularies for anti-inflammatory and analgesic doses and previous literature (Houghee et al. 2006; and Glowka et al. 2000). Ibuprofen was in suspension and delivered orally at 50 mg/kg/day.

The nNOS inhibitor 3-bromo-7-nitroindazole (3-B-7-Ni) (Cayman Chemical) or the endothelin receptor type 1b agonist, sarafotoxin 6c (a vasoconstrictor peptide, Alexis Biochemicals), was resuspended in DMSO at 100 mg/ml and 1 mg/ml, respectively. 3-B-7-Ni was diluted 1:10 in sunflower oil and immediately injected at 20 mg/kg I.P. Sarafotoxin 6c was diluted 1:1000 in 0.9% saline and immediately injected at 5 ug/kg I.P.

Dosage of PDE5A inhibitor was designed to give a good exposure to PDE5A, taking into account the following points: a dose of 100 mg/kg/day will give a mean free plasma concentration of 10.4 nM (Gupta et al. 2005; Takimoto et al. 2005; and Walker et al. 1999) (the $IC_{50}$ of sildenafil at PDE5A is 5-10 nM (Takimoto et al. 2005) thus 100 mg/kg/day is at the $IC_{50}$ for sildenafil at PDE5A), PDE5 activity is elevated 2-6x in mouse leg muscle extracts from mdx mice (Asai et al. 2007), and food-drug interactions reducing the rate of absorption and extent of systemic exposure for PDE5A inhibitors (Gupta et al. 2005). Doses of 100, 300, and 500 mg/kg/day were tested on mdx mice and 300 mg/kg/day gave the best response (see FIG. 11d). Assuming linear pharmacokinetics from 100-300 mg/kg/day, 300 mg/kg/day will produce approximately a plasma concentration of 30 nM, exceeding the IC50 by 3-6 fold, inhibiting more than 50% of the enzyme activity. Therefore, for acute tadalafil (Kemprotec) treatment, tadalafil was given orally by gavage at 300 mg/kg the day before and the day of the exercise-activity protocol to ensure that the mice received one full day of inhibitor dosage before the exercise-activity protocol. For acute sildenafil citrate (Pfizer) treatment, sildenafil was given orally by mixing the drug into water softened rodent gruel (2019 Teklad global 19% protein rodent chow; 4-6 g/day). Mice were supplemented with normal chow (7013 NIH-31 modified diet) to ensure ad libitum feeding. For $K_{ATP}$ channel agonists, stocks at 100 mg/ml of Minoxidil (Sigma) and pinacidil (Alexis Biochemicals) were resuspended in DMSO, and nicorandil (SynFine Research) was resuspended in water. Each drug was diluted in 0.9% saline immediately before i.p. injection, at 0.8 mg/kg in the case of minoxidil and pinacidil or 0.1 mg/kg in the case of nicorandil. L-NAME was given orally by gavage at 100 mg/kg in 0.9% saline the day before and the day of the exercise-activity protocol. Superoxide dismutase (Sigma) was given by i.v. at 1000 U/mouse. Tempol (Alexis Biochemicals) was delivered by i.p. at 260 mg/kg. All agents were administered 30 minutes prior to exercise-activity analysis unless otherwise stated.

Magnetic resonance imaging (MRI). MRI was performed using a Varian Unity/Inova 4.7 T small-bore MRI system (Varian Inc., Palo Alto, Calif.). The acquisition consisted of a $T_2$-weighted fast spin-echo sequence (TR/TE=5000/48 ms) with in-plane resolution of 0.11 mm×0.22 mm and slice thickness of 0.6 mm acquired in the axial plane. Imaging of mice was+/−exercise. For imaging, mice were anesthetized with an i.p. injection of ketamine/xylazine (87.5 mg/kg and 12.5 mg/kg, respectively). If with exercise, imaging started 30 minutes post-exercise. 4 mdx mice were imaged for pre-exercise and 7 mdx mice were imaged for post-exercise and 5 mdx were treated with PDE5A inhibitor. Three mice were examined for other sets. Measurements to determine percent muscle edema were done with Image-ProPlus6.0 Software. Axial or coronal muscle areas were measured and fat and cartilage were subtracted. Total areas of edema were measured within the same slice and divided by the resultant axial muscle area and multiplied by 100 to get percent muscle edema area for each mouse tested (FIG. 3g). The middle axial and coronal slices were used for this quantitation as these slices gave the greatest viewable muscle area per scan. Axial and coronal calculations gave similar and consistent percent muscle edema areas.

Statistical analysis. Unless otherwise stated, the data were calculated according to an analysis of variance. P-value calculations were made between genetically defined mouse models and their wild-type counterparts or between treated and untreated mice using the Kruskal-Wallis One Way Analysis on Ranks. Data are expressed as mean±SEM.

The exaggerated fatigue response to mild exercise is not muscle weakness. Evidence from mouse models demonstrates that reduced sarcolemmal nNOS does not affect muscle contractility: microdystrophin/nidx (Harper et al. 2005), MCKεSG/Sgca-null, and α1-syntrophin-null (Kameya et al. 1999) mice have mislocalized nNOS but this does not influence contractile properties. In addition, nNOS-null muscles produce force comparable to, or even greater than, the force generated by wild-type muscle at different oxygen tensions (Eu et al. 2003). To further test if loss of nNOS affects contractility, a set of nNOS-null mice were exercised and allowed to rest 10 minutes, which was within the 30 minute time interval used to assess the fatigue response after mild exercise (FIG. 7). The mice then were put on the treadmill again. The mice were able to run the full running protocol again indicating that they were still capable of performing physical activity and that the activity was not exhaustive. The nNOS-null mouse data show that loss of nNOS-derived NO signaling leads to prolonged exercise-induced inactivity similar to that identified in the dystrophic and rescue mouse models. In the mouse models with the fatigue response to mild exercise, full activity returned, and vascular narrowing were not present 4 hours after exercise indicating that the vascular narrowing as well as loss of activity post-exercise is not sustained. Vascular narrowings and the fatigue response occur again upon re-exercising of mice. Non-selective NOS inhibitor data are consistent with the results from the treatment of wild-type mice with the relatively specific nNOS inhibitor 3-bromo-7-nitroindazole: treatment of wild-type mice with L-NNA prevents adequate exercise-induced hyperemia and limits exercise capacity during exhaustive treadmill running (Kinugawa et al. 2005); treatment of wild-type and mdx mice with L-NAME increases mean arterial pressure and decreases femoral blood flow velocity and vascular conductance (Thomas et al. 1998); L-NAME treatment severely reduces walking speed in rats (Wang et al. 2001), and local intra-arterial infusion of L-NMMA into human forearm reduces resting blood flow and a transient systemic increase in blood pressure (Seddon et al. 2008). It was found that treatment of wild-type mice with L-NAME reduced post-exercise activity to levels similar to those in nNOS-null mice post-exercise, and that treatment of dystrophic or nNOS-null mice with L-NAME reduced the activity post-exercise even more, in fact preventing Microfil® from circulating sufficiently for images to be taken (data not shown). The L-NAME results are also consistent with the sarafotoxin 6c treatment of wild-type mouse data. In addition, the NOS inhibitor and sarafotoxin data are consistent with the fact that deflazacort treatment of mdx mice did not ameliorate inactivity post-exercise as glucocorticoids reduce inflammation by causing vasoconstriction to reduce blood flow and thus reducing permeability between the endothelial cells (Perretti et al. 2000).

The exaggerated fatigue response to mild exercise is not due to oxidative stress, inflammation, or atrophy. To test the possibility that an inhibition of mitochondrial respiration inhibition causes the observed post-exercise inactivity, mdx mice treated with superoxide dismutase (SOD) or mdx mice overexpressing the extracellular superoxide dismutase (under the R-actin promoter) were tested in the exercise activity assay. It was found that neither method of SOD exposure had an effect on the exaggerated fatigue response to mild exercise. In addition, since reactive oxygen species (ROS) increases the protein nitrosylation, mdx mice were treated with Tempol, a water-soluble, membrane permeable scavenger of superoxide anions that also reduces hydroxyl radical formation, and found that the drug had no effect on the exaggerated fatigue response in mdx mice. Furthermore, immunohistochemistry for nitrotyrosine in muscle sections of wild-type, rescue, or nNOS-null mice showed no changes+/−exercise.

Expression of HIF-1α, an oxygen-dependent transcription activator that accumulates during oxidative stress, was assessed on skeletal muscle sections and on immunoblots of skeletal muscle homogenates, in wild-type, mdx, rescue, and nNOS-null mice before and after mild exercise, and did not detect any changes compared to levels in wild-type muscle. Tissue also was examined, hypoxia+/−exercise in wild-type, rescue, and nNOS-null mouse models, by injecting Hypoxyprobe™-1 and probed for hypoxyprobe adducts. No signs of skeletal muscle hypoxia after the mild exercise was observed.

On muscle sections of the non-dystrophic mouse models that displayed the exaggerated fatigue response, inflammation was assessed using I-A$^b$ MHC class II and F4/80, and did not detect inflammation. To test for atrophy, myosin heavy chain 2A was assessed. No signs of atrophy were observed.

Loss of nNOS in mdx mice does not exacerbate muscle damage but will increase the exaggerated fatigue response to mild exercise. Comparative analyses of muscle pathology in mdx/nNOS-null mice versus mdx mice have led to the conclusion that mdx dystrophic pathology is independent of nNOS perturbation (Crosbie et al. 1998; and Chao et al. 1998). However, fatigue was not analyzed in the mdx/nNOS-null mouse studies, and these mice were not challenged with exercise to test the repercussions of complete loss of nNOS in mdx muscle. On the other hand, NOS-Tg1mdx mice, which overexpress nNOS in mdx muscle, showed an amelioration of common indices of muscle pathology, due to reduced inflammation and membrane injury (Wehling et al. 2001). These mice, however, in spite of a 50-fold increase in nNOS protein in transgenic muscle, have only ~0.2 fold increase in NO production. This finding is reminiscent of the up-regulation of nNOS in DMD myofibers, which is accompanied by low NO levels (Punkt et al. 2006). The low NO production in NOS-Tg/mdx mice was attributed to possible increased expression of NOS inhibitors. However, this study did not confirm the localization of the overproduced nNOS protein, analyze fatigue, or challenge the NOS-Tg/mdx mice to analyze the effects of the 50-fold increase in nNOS expression in mdx mice.

The muscle nNOS data are consistent with recent evidence showing that a structurally intact DGC in smooth muscle only partially restores a-adrenergic vasoregulation in mdx hindimbs (Asai et al. 2007), suggesting an extrinsic vascular contribution to vasomodulation. Importantly, vascular constrictions are only observed in thskeletal muscle vasculature post-exercise in the mdx, Sgca-null, nNOS-null, and rescue mice. Vascular narrowing was not detected in other organs.

The vasodilators bypass the nNOS-NO-cGMP mechanism and stimulate general vasodilation. While this would prevent vasoconstrictions like those seen with verapamil in sarcoglycanopathy mouse models (Cohn et al. 2001), the bypass also eliminates the mechanism of nNOS stimulation by muscle contraction. Thus, the animals become hypotensive upon exercise and more inactive. For example: mice treated with minoxidil have catecholamines released into their bloodstream—a baroreflex-mediated response to low blood pressure (Tsunoda et al. 2001); nicorandil dilates peripheral and coronary resistance arterioles, systemic veins, and eeicardial coronary arteries, thus significantly reducing blood pressure in mammals (Barbato et al. 2005), and pinacidil decreases mean arterial pressure in wild-type mice (Miki et al. 2002).

The data show that the exercise-induced prolonged fatigue response is alleviated by PDE5A inhibitor treatment, indicating that the observed effect is due to cGMP, which acts downstream of NO production. Downstream effects of low, physiological levels of NO (e.g. mitochondrial biogenesis and vasodilation) are cGMP-dependent, whereas downstream effects of high (pathological) NO levels (e.g. generation of reactive oxygen species and nitrosylation of proteins, lipids, and DNA) are cGMP-independent (Stamler et al. 2001).

Construction of transgene, transgenic mice, and MCKεSG/Sgca-null rescue mice. To direct skeletal and cardiac muscle-specific expression of ε-sarcoglycan in mice, an MCKεSGpA transgene was constructed: a 5' blunt-ended ClaI-3' XhoI fragment of the murine muscle-specific creatine kinase (MCK) 6.5-kb promoter/enhancer (Johnson et al. 1989), was ligated into pGem7Zf(+) (Promega) 5' blunt-ended AatII NhoI sites. The full-length human ε-sarcoglycan cDNA (human and mouse ε-sarcoglycan are 96% identical) was PCR synthesized from a human skeletal muscle cDNA library (Clontech) and engineered with 5' XhoI-3' KpnI sites then ligated downstream of the MCK promoter. An SV40 polyadenylation signal was PCR engineered with 5' KpnI-3' HindIII/NruI/SacI linker and the KpnI-SacI fragment was ligated downstream of the ε-sarcoglycan coding region. All constructs were confirmed by DNA sequencing by the University of Iowa DNA Facility. The MCKεSGpA EcoRV NruI 7,986-bp transgene was microinjected by the University of Iowa Transgenic Animal Facility. Founder mice were identified, genotyped, and confirmed by PCR reactions of mouse genomic DNA isolated from tail or ear-snips (Sigmund et al. 1992). Injection of the transgene yielded 3 independent germ line-transmitting founders, which were backcrossed to the C57BL/6 background to generate stable MCKεSG transgenic lines, and offspring were subsequently genotyped by PCR. Skeletal muscles from subsequent generations of transgenic mice were analyzed by SDS-PAGE to check for consistent expression of the transgene. MCKεSG/Sgca-null mice were generated by two rounds of breeding with Sgca-null mice (Duclos et al. 1998) on a congenic C57BL/6 background. Offspring were PCR-genotyped for transmission of the transgene and loss of the corresponding allele.

Immunoblotting, immunofluorescence and histological analysis. Antibodies for immunoblots were MANDRA1 (dystrophin, Sigma-Aldrich), IIH6 (α-dystroglycan) (Ervasti et al. 1991). Rabbit 83 ((β-dystroglycan) (Williamson et al. 1997), Rabbit 229 (δ-sarcoglycan) (Roberds et al. 1993), and Rabbit 256 (sarcospan)4a Monoclonal antibodies Ad1/20A6 ((α-sarcoglycan), βSarc1/5B1 (β-sarcoglycan), and 35DAG/21B5 (γ-sarcoglycan) were generated in collaboration with L.V.B. Anderson (Newcastle General Hospital, Newcastle upon Tyne, UK). For the ϵ-sarcoglycan antibody (Rabbit 284), rabbit polyclonal antibodies were generated in New Zealand white rabbits intramuscularly and subcutaneously injected with a C-terminal mouse ϵ-sarcoglycan peptide (CQTQIPQPQTTGKWYP (SEQ ID NO:1)) covalently linked to BSA. Antibody specificity was verified by competition experiments with the corresponding peptide on immunoblots. KC1-washed skeletal muscle membranes were prepared and immunoblot analysis was performed as described previously (Durbeej et al. 2000). Immunofluorescence was performed on 7-µm transverse cryo sections as previously described (Duclos et al. 1998). Evans blue dye injections and exercise experiments were performed as described previously (Duclos et al. 1998; and Straub et al. 1999).

Example 4

Figure 14:
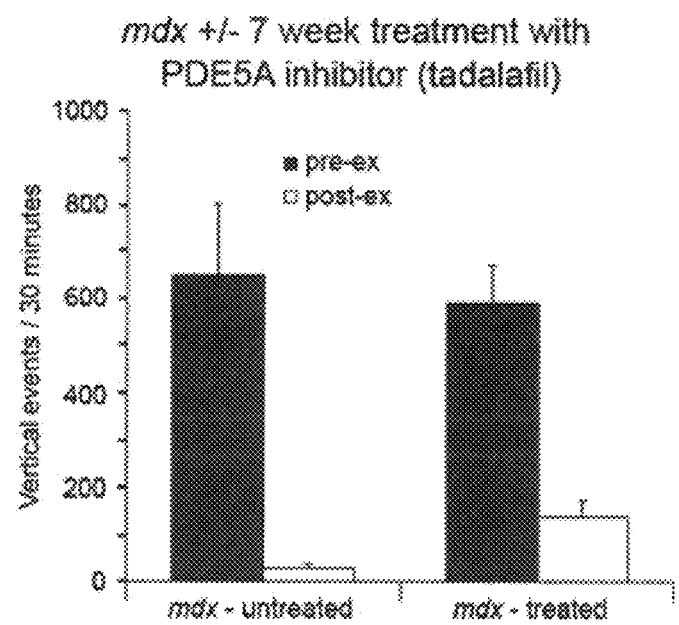
FIG. 14. illustrates the results of seven wk treatment of mdx mice+/−PDE5A inhibitor tadalafil. Long-term (7 wk) daily treatment of mdx from weaning to 10 wks of age with tadalafil.
Figure 15:
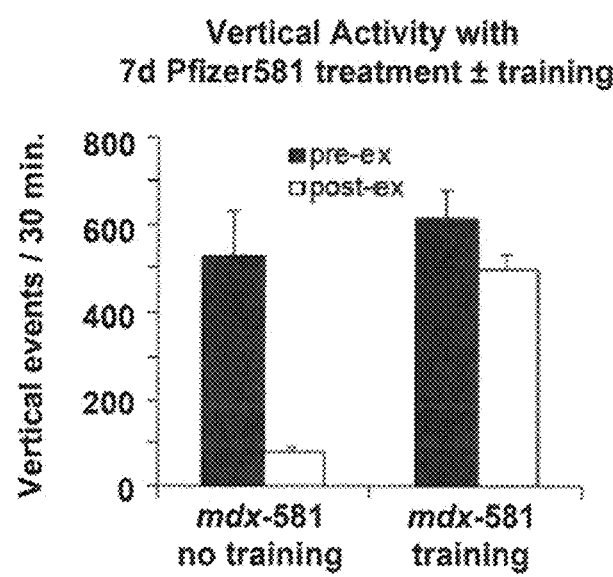
FIG. 15. illustrates the results of seven day treatment of mdx mice with long-term PDE5A inhibitor+/−exercise. Suggesting there is a synergistic mechanism involved with long-term PDE5A inhibition and training.

Molecular Mechanisms Involved in Exaggerated Fatigue Response and Exercise-induced Muscle Edema Effects of long-term PDE5A inhibitor treatment on mouse models of muscular dystrophy. mdx mice were treated soon after weaning with daily sildenafil and tadalafil up until 10 weeks of age and analyzed in out exercise-activity assay. Sildenafil was dissolved in food and tadalafil was delivered by oral gavage. FIG. 14 shows results from long-term (7 week) tadalafil treatment. Although long-term PDE5A inhibitor treatment in mdx mice appeared to increase in post-exercise activity in these set of mice, post-exercise activity was not much higher than normally observed. There are several factors that could be the reason—mdx already was shown to have elevated PDE activity in muscle, thus PDE activity may have gradually increased with age along with treatment, or the pharmacokinetics of the inhibitors are just not meant for long-term treatments. In collaboration with Pfizer, derivative of sildenafil called PF-581253 was tested (mdx-581 in FIG. 15). PF-581253 is a long-term inhibitor of PDE5A activity. A 52-day treatment regimen gave the same results as the long-term treatment with tadalafil or sildenafil. However, a recent paper by Narkar et al. 2008 suggest that some drugs only increase oxidative myofibers and running endurance when combined with exercise training. A 7-day treatment regiment of PF-581253 was performed with and without training. A profound effect with long-term PDE5A inhibitor treatment was observed (FIG. 15). Even though the pathways involved in cGMP signaling are divergent, this preliminary result suggests important clues as to the mechanism involved with the exaggerated-fatigue response to mild exercise.

Figure 16:
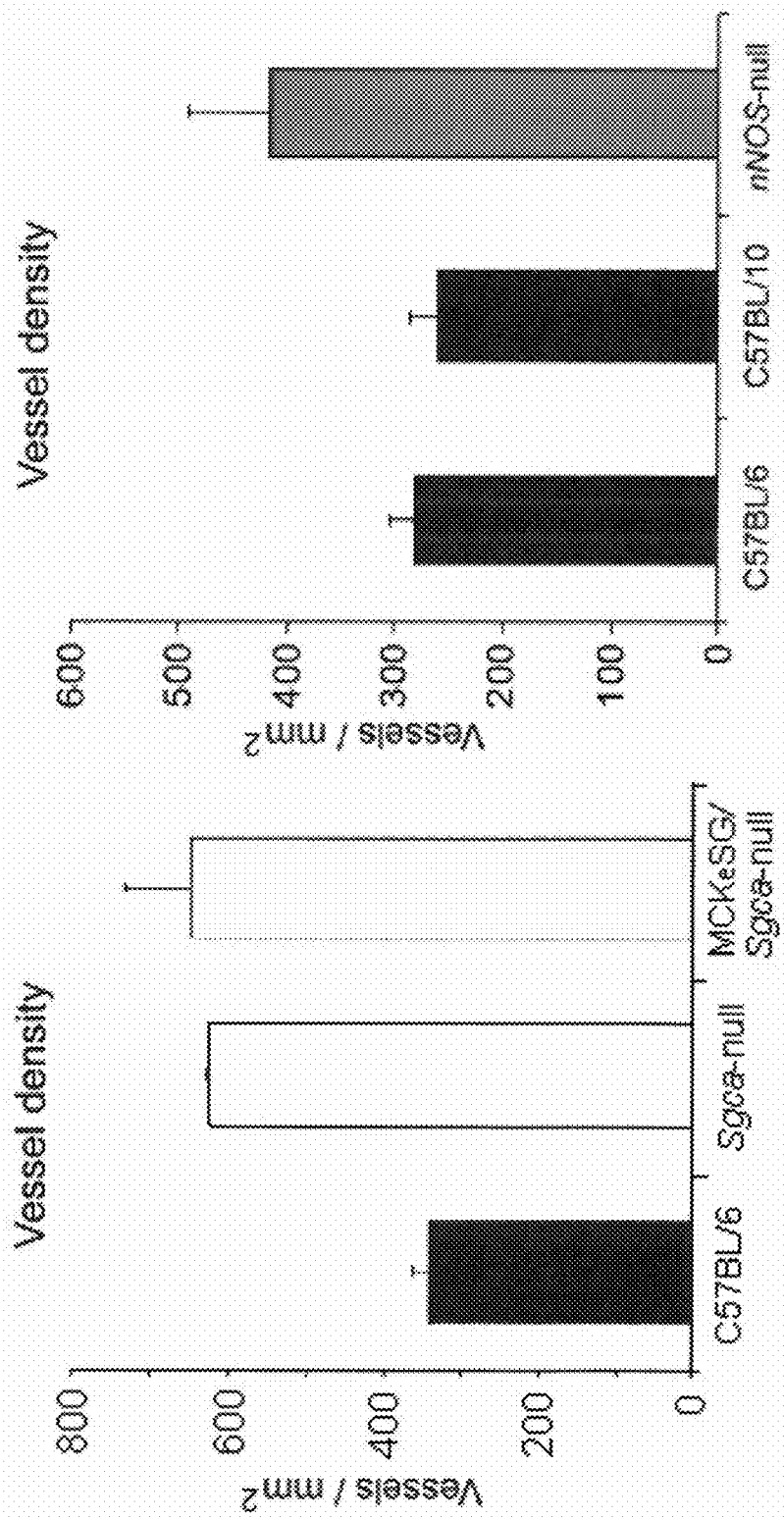
FIG. 16. illustrates vessel densities in quadriceps of wild-type, Sgca-null, and nNOS-null mice. Mouse models that displayed post-exercise vascular narrowings also showed increased vessel densities.

Correlation between perfusion and vessel density in dystrophic muscle or in muscle with mislocalized nNOS. The paper revealed that mdx muscle can perfuse quite well from exercise but only when treated with PDE5A inhibitors (Kobayashi et al. 2008). Muscle vessel densities were counted in MCKϵSG/Sgca-null rescue mouse and were compared to the density of wild-type (C57BL/6) and Sgca-null mice (FIG. 16, left panel). The rescue mouse as well as the dystrophic counterpart were observed to have about the same vessel density, which was well above that of wild-type. The Sgca-null density could be explained by variation in fiber size or an increase in regenerating fibers, but the rescue mouse did not have variation in fiber size or increased regeneration as it did not have muscle pathology. Submaximal strength performance depends on muscle capillary density and is linked to endurance capacity of the muscle tissue in humans (Terzis et al. 2008), so the exaggerated fatigue response in the MCKϵSG/Sgca-null mouse just after mild exercise suggests that the muscles are not getting perfused enough despite the increased vessel density. The muscle vessel density of another non-dystrophic mouse with nNOS deficiency, the nNOS-null mouse, then was counted and compared to the density of two wild-type strains (C57BL/6 and C57BL/10) (FIG. 16, right panel). The nNOS-null skeletal muscle also had an increase in vessel density. Increases in vessel density without muscle pathology suggest a compensatory mechanism for inefficient nNOS signaling from the muscle. This compensation, however, is not sufficient as each mouse model with the mislocalized or deficient nNOS still had the exaggerated fatigue response to mild exercise.

Figure 17:
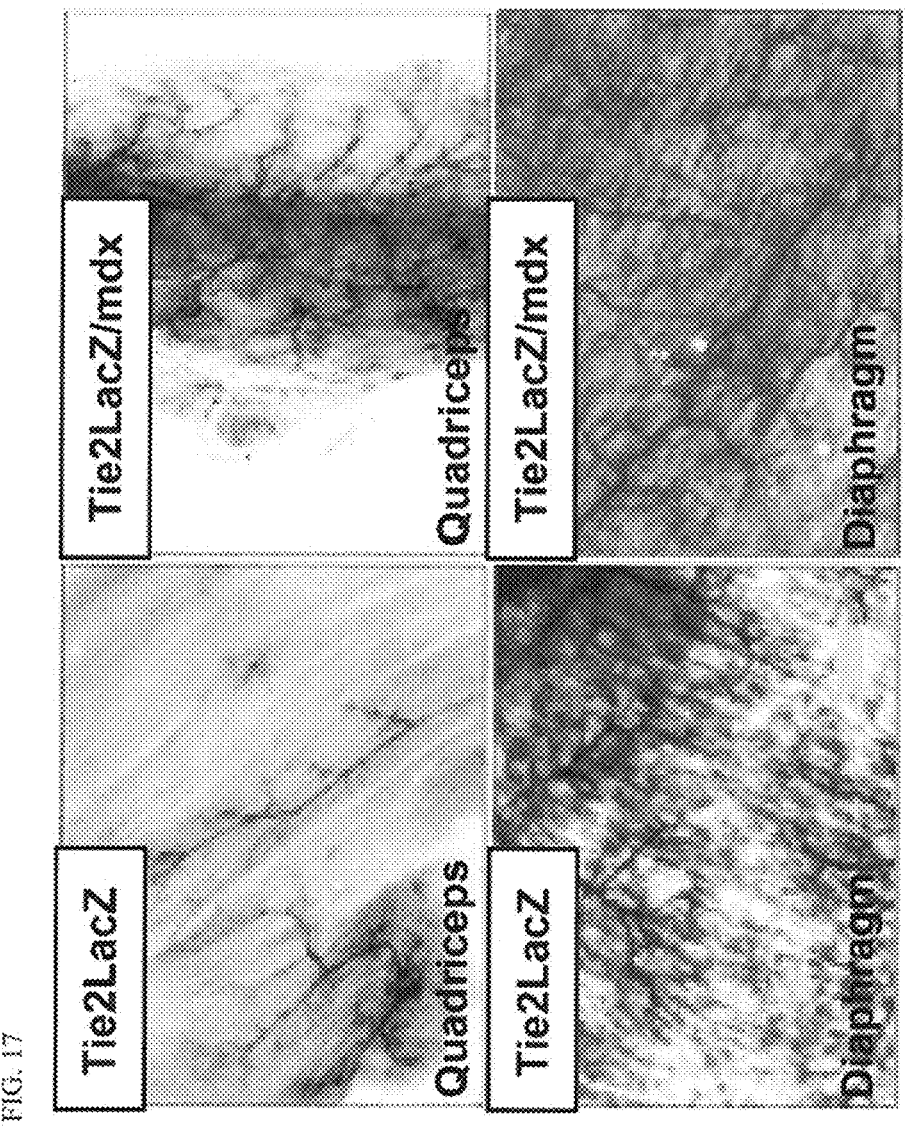
FIG. 17. illustrates whole mounts staining for β-galactosidase activity in quadriceps and diaphragm muscles from Tie2LacZ (wild-type) and Tie2LacZ/mdx mice. Mdx mice have increased areas of vessel branching.

Next, mdx mice were crossed with the Tie2LacZ mice, which have the Tie2 promoter driving the expression of the LacZ reporter gene exclusively in endothelial cells. Therefore any endothelial lined vessel can be visualized by staining for β-galactosidase activity. Even though the Tie2LacZ/mdx mice will not show perfusion since all endothelial lines vessels will be labeled, the Tie2LacZ/mdx mice provide a qualitative gauge as to the density of the vessels. Upon whole mount staining for β-galactosidase activity in the muscles of these mice, it was found that mdx muscle had a substantial increase in vessel branching compared to wild-type mice that were crossed with the Tie2LacZ mice (FIG. 17). Decreased muscle capillarization is associated with glucose intolerance (Prior et al. 2009) so it is possible that glucose uptake may be involved in the fatigue response, even though and increase in capillarization is observed in mdx muscle.

The vessel density and Tie2LacZ preliminary results strongly suggest that the increased density is to compensate for deficient muscle nNOS signaling and suggests a basis as to why long-term PDE5A inhibitor treatment possibly did not work in mdx muscle. It is possible that the long-term PDE5A inhibitor treatment lead to a decrease in vessel density or vessel branching. This result could also explain why the training plus long-term PDE5A inhibitor treatment worked so well in the preliminary trial.

Example 5

Preclinical Endpoint Measurement for Muscular Dystrophy Clinical Trial

The following Example describes a preclinical, mouse model, functional assay using ambulation as a direct measure of mobility, disease severity, and response to treatment.

Abstract

Loss of mobility strongly influences the quality of life for patients with neuromuscular diseases. This study investigated preclinical endpoint measures, which test mobility and muscle pathology, to improve their translation to the clinic. Using mouse models, a preclinical, in vivo functional assay was developed using ambulation as a direct measure of mobility, disease severity, and response to treatment. In addition, preclinical endpoint measures that evaluate muscle pathology and biomarkers of muscle damage were refined. This study demonstrated that a six-minute ambulation assay is a responsive, functional preclinical test for therapeutic strategies in muscular dystrophy. Similar to the six-minute walk test for ambulatory Duchenne muscular dystrophy boys, mdx mice ambulated shorter distances than normal controls, a disparity that was accentuated after mild exercise. The six-minute ambulation assay reflected degrees of muscle pathology of different mdx mouse models. Bilateral examination of mdx hind limb muscles also revealed asymmetric skeletal muscle pathology. Furthermore, the peak analysis time for the biomarkers serum creatine kinase and urine myoglobin reflecting muscle damage was identified. These findings demonstrating the use of the six-minute ambulation assay and refined biomarker measurements of muscle damage will enhance the translatability of positive preclinical findings to the clinic for muscular dystrophy and other conditions in which declining musculoskeletal function leads to loss of mobility. Furthermore, these data highlights the necessity for preclinical and clinical studies to consider asymmetric muscle pathology and timing of biomarker assays of muscle disease when designing protocols that investigate potential therapies for muscular dystrophy.

Introduction

Duchenne muscular dystrophy (DMD) is caused by mutations in the X-linked dystrophin gene that lead to a complete loss of dystrophin expression in muscle. The mdx mouse lacks dystrophin due to a point mutation in the dystrophin gene (Blake et al. 2002). The mdx muscle pathology is similar to young DMD boys, but the clinical course is less severe than older patients. Investigations using the mdx mouse have provided insights into the complex mechanisms leading to muscle degeneration, progression of muscle weakness, and clinical presentation of the disease. Importantly, preclinical studies using the mdx mouse have suggested numerous potential targets for DMD therapeutic testing in clinical trials.

Timed submaximal exercise performance assays are used to test the efficacy of potential therapies for DMD and to unmask phenotypes in both patients and animal models of dystrophin deficiency (Kobayashi et al. 2008; Weiss et al. 2010). The step-activity monitor and six-minute walk test are two forms of this kind of testing used to compare physical performance in normal and ambulatory DMD boys (Mcdonald et al. 2005; McDonald et al. 2009). Here, two tests were combined to take advantage of the normal ambulation of the mouse within a fixed time, while considering the sedentary nature of laboratory mice. The difference in ambulation performance between mdx and wild-type mice, particularly after mild exercise, parallels that of DMD and control boys in the six-minute walk test (McDonald et al. 2009). The data presented here demonstrate that ambulation distance within six minutes is an accurate preclinical performance outcome measure for mdx mice, and when used in conjunction with other refined endpoint measures, will enhance the translatability of preclinical data for DMD, and other loss of mobility conditions, to the clinic.

Methods

Mice. The Jackson Laboratory mouse strains used in this study: C57BL/6J, B6.129P2-Nos3$_{tm1Unc}$/J, B6.129S4-Nos1$_{tm1Plh}$/J, B6.129P2-Nos2$_{tm1Lau}$/J, and C57BL/10ScSn-Dmd$_{mdx}$/J (abbreviated as C57BL/6, eNOS-null, nNOS-null, iNOS-null, and mdx, respectively). Other mice used were: B6.129Sv-Mb$_{tm1Djg}$ and B6.129Sv-Utrn$_{tm1Jrs}$ (abbreviated as Mb-null (Garry et al. 1998)) and Utrn-null (Grady et al. 1997), respectively). Mb-null; mdx, mdx; iNOS-null, mdx; nNOS-null, and mdx; Utrn-null mice were generated by intercrossing mice to produce mice on a mixed C57BL/6J; C57BL/10ScSnJ background. Phosphodiesterase 5A inhibitor treatment for mdx mice was previously described (Kobayashi et al. 2008). Mice were bred at the University of Iowa to produce a large enough number of mice from the same breeding pair for each cohort of experiments. Mice were males at 10 weeks old unless otherwise stated, and had food and water ad libitum with exposure to the same care handler. Mice were synchronized, grouped housed, and tested in rooms on the same shifted 12:12-hour light:dark cycle. Testing time of all mice was at Zeitgeber time 14-17, when the mice were physiologically awake and active (Thompson et al. 2008). Mouse housing and activity rooms were under specific pathogen-free conditions. All mouse experiments were performed in accordance with animal usage guidelines and regulations set forth by NIH and the University of Iowa Institutional Animal Care and Use Committee. Mice were maintained within a centralized barrier animal facility at the University of Iowa directed by the Office of Animal Resources.

Six-minute ambulation distance test. Mouse activity was monitored using the VersaMax Animal Activity Monitoring System as previously described (Kobayashi et al. 2008). Mice were tested in individual chambers, for 6×1 minute intervals before and immediately after exercise. Data were transferred to a Microsoft Excel worksheet and calculations were done within the Excel program.

Magnetic resonance imaging (MRI). Mice were anesthetized using a mixture of ketamine and xylazine (87.5 and 12.5 mg/kg, I.P.), and the plane of anesthesia was confirmed by absence of the pedal reflex. For scans done after exercise, imaging started less than 10 minutes after exercise to allow for mice to be anesthetized. Images were captured in the axial and coronal planes with a Varian Unity/Inova 4.7 T small-bore MRI system (Varian, Palo Alto, Calif.), using an acquisition consisting of $T_2$-weighted fast spinecho sequence (TR/TE=5000/48 ms) with in-plane resolution of 0.11 mm×0.22 mm and slice thickness of 0.6 mm Treadmill exercise. Mice were mildly exercised with an adjustable variable-speed belt treadmill from AccuPacer as previously described (Kobayashi et al. 2008).

Contractile properties of isolated muscle. Contractile properties were measured for isolated male mdx extensor digitorum longus muscles from 5 unexercised or 5 post-exercised mice ages 16-19 weeks. Measurements post-exercise were done within 15-30 minutes after exercise. Mice were anesthetized with an intraperitoneal injection of 1.3% avertin (0.015 ml/g body weight) and muscles removed. The distal tendon was clamped to a post and the proximal tendon was tied to a dual mode servomotor (Aurora Scientific) with 6-0 suture. Contractile properties, optimal fiber length and maximal isometric tetanic force, were determined as previously described (Brooks et al. 1988). The lengthening contraction protocol (LCP) was previously described (Wang et al. 2010). The force deficit was defined as the difference between pre and post-LCP force expressed as a percentage of pre-LCP force (Wang et al. 2010). P-value calculations were made using a Student t test.

Serum creatine kinase assay. Pre- and post-exercise serum creatine kinase (sCK) levels were measured as previously described (Kobayashi et al. 2008). For this study, blood collection and assays were done at designated time points. To reduce variability in data sets (Spurney et al. 2009), all mice used were male, from the same breeding colony, and of the same age. Mice used for FIGS. 22A, 22F, and 22G were each from a different breeding colony. Normal sCK levels=100-500 U/L. Elevated sCK levels>500 U/L and hyper-CKemia values were considered approximately ≥20,000 U/L. For blood collection, mice were placed in a restrainer, which they freely walked out of after blood collection. The initial drop of blood after the tail vein nick was wiped away and the subsequent 25 μl of blood was collected without tail manipulation. Serum was diluted 1:9 and 1:49 (v:v), to ensure activity levels within the limits of the assay, and assayed in triplicate. There was a minimum of 24 hours between blood collections from the same mouse. For sCK at different intervals, sCK from eight sets of mdx mice were measured 24 hours prior to exercise. On test day (0 d), all eight sets of mice were exercised and sCK was assayed 2 hours post-exercise; 24 h following the initial exercise, the 1 d set of mdx mice were run again and sCK was assayed; the same procedure was followed for all other groups for subsequent interval days after the initial run. For sCK at different intervals within a 120-minute time-frame after exercise, nine sets of mice were used with each set of mice representing a time point.

Urine collection and dip stick assay. Urine was collected from each mouse by allowing mice to urinate over a fresh piece of aluminum foil. Voided urine was transferred to a fresh microcentrifuge tube, the color noted, and tested immediately. Urine was applied to the reagent strip (Siemens Multistix® 10SG) in which the development of a blue color indicated high levels of a heme protein. None of the mice had hematuria.

Evans Blue Dye uptake imaging and quantification. Evans Blue Dye (EBD) injection was described previously (Straub et al. 1997). After 3 h, mice were run on a treadmill. Mice were sacrificed and quadriceps and gastrocnemius muscles were collected. Axial 7 μm cryo-sections of skeletal muscle were visualized (Straub et al. 1997). For quantification, each muscle was placed in 1 ml of N,N-dimethyl formamide for 48 h to extract the EBD. Absorbance of EBD in each solution was measured at 630 nm. Values were normalized by dividing by the weight of the tissue.

Results

Figure 18:
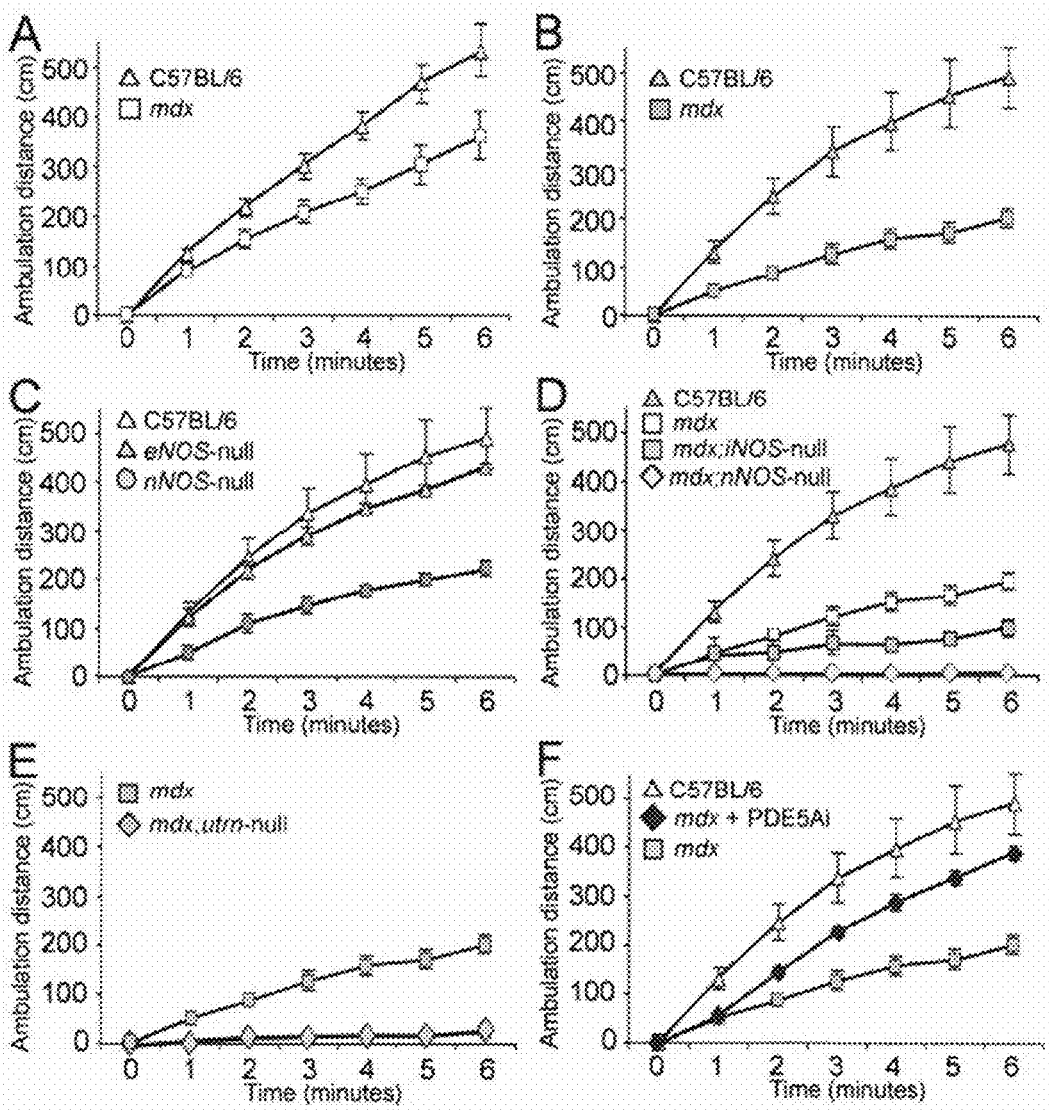
FIG. 18. illustrates six-minute ambulation distance as an endpoint measure in preclinincal investigations for DMD using an ambulation distance assay that was developed by adapting the step-activity and six minute walk tests for mice using an open field activity chamber. (A) Basal ambulation distances versus time of C57BL/6 and mdx mice were charted. Ambulation distances were charted after mice were challenged with mild exercise (B, C, D, E, and F). (B) C57BL/6 versus mdx mice. (C) C57BL/6 versus eNOS- and nNOS-null mice. (D) C57BL/6 versus mdx, mdx; iNOS-null and mdx; nNOS-null mice (E) mdx versus mdx; Utrn-null mice. (F) C57BL/6 versus mdx treated with phosphodiesterase5A inhibitor and untreated mdx mice (n=6 for mdx, C57BL/6, nNOS-null, eNOS-null mice, and mdx+PDE5Ai; n=4 for mdx; nNOS-null, mdx; Utrn-null, and mdx; iNOS-null mice. Error bars indicate SEM).

Ambulation distance within six minutes to measure mdx mouse performance. The step-activity monitor and six-minute walk test in the form of a six minute ambulation distance assay were combined to assess mouse performance (FIG. 18). Comparing basal ambulatory performance over six minutes, the results illustrate that mdx mice show less ambulatory distance over six minutes than normal wild-type mice (FIG. 18A). This difference in ambulation performance between mdx and wild-type mice parallels that of DMD and control boys in the six minute walk test (McDonald et al. 2009). Because ambulatory DMD boys are not sedentary like normally housed mdx mice, the clinical relevance of the ambulatory assay was ensured by physically challenging the mice before measuring their ambulatory performance. As ambulatory DMD boys do not perform hard activities to exhaustion, the mdx mice were challenged with mild treadmill exercise, as previously described (Kobayashi et al. 2008), before ambulation was assessed. C57BL/6 mice showed no significant difference in ambulation before and after exercise. However, with exercise, ambulation of mdx mice was affected and the difference between wild-type and mdx mouse ambulation distance was accentuated (FIG. 18B). These ambulation data clearly demonstrate a distinction between control and mdx mouse performance, particularly after mild exercise.

Figure 19:
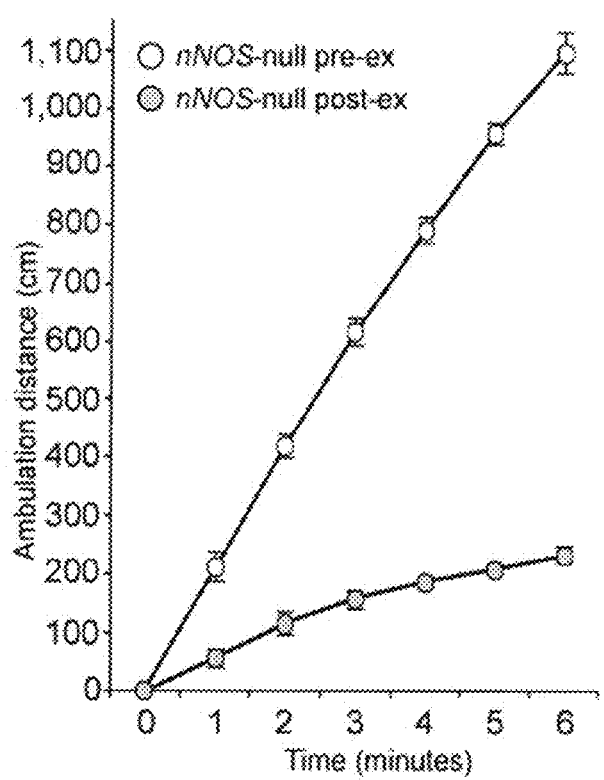
FIG. 19. illustrates six-minute ambulation distance for nNOS-null mice. Using an open field activity chamber, basal ambulation performance was measured from nNOS-null mice with no previous exercise challenge (pre-ex). The next day, the same mice were exposed to a mild exercise challenge and their ambulation performance was measured. Total distances traveled during the first six minutes for each set were averaged and charted.

To validate the ambulation assay, the post-exercise performance of other mouse models used to examine pathogenic mechanisms of dystrophin deficiency also were tested. Constitutively active endothelial and neuronal nitric oxide synthase (eNOS and nNOS, respectively) enzymes play important roles in vasomodulation, but only genetic deletion of nNOS in mice leads to mdx-like debility after mild exercise (Kobayashi et al. 2008). Similarly, only nNOS-null mice displayed reduced ambulation postexercise (FIGS. 18C and 19). Referring to FIG. 19, the six-minute ambulation assay showed that without a mild exercise challenge, nNOS-null mice display hyper-ambulation. This data is consistent with the hyperactive locomotor activity of nNOS-null mice recently reported (Blake et al. 2002). After a bout of mild exercise, however, this hyperambulation drops significantly. The drop in ambulation distance is consistent with the drop in nNOS-null mouse vertical activity after mild exercise (Kobayashi et al. 2008).

Figure 20:
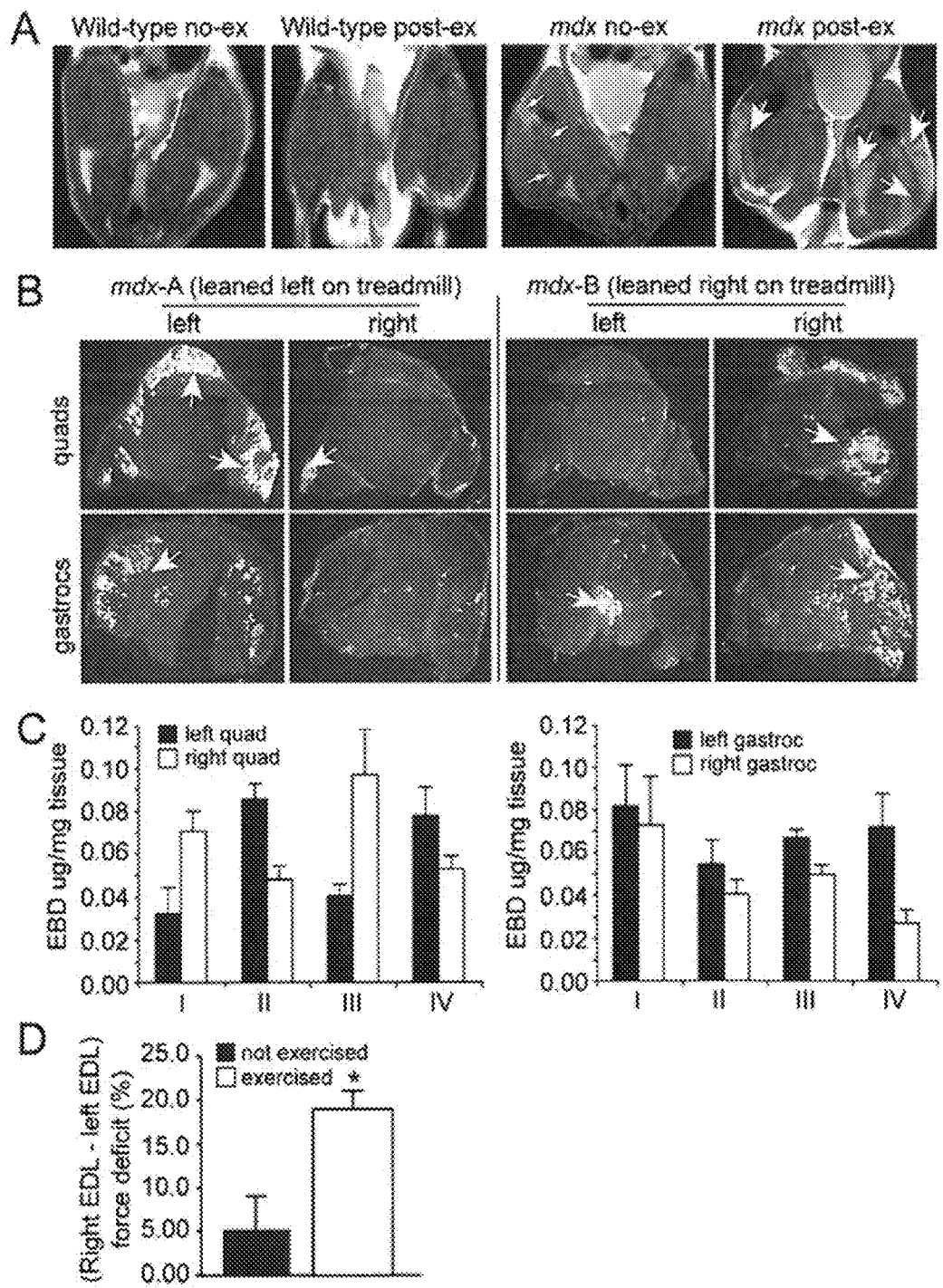
FIG. 20. illustrates muscle pathology of mdx; iNOS-null mice. (A) Vertical activity pre- and post-exercise was monitored in an open activity chamber for 30 minutes, and data was quantitated and charted on an Excel spreadsheet (n=4). (B) Indices of muscle damage from serum (n=8) and urine (n=4) were assayed for creatine kinase and myoglobin, respectively. (C) Magnetic resonance imaging of hind leg quarters of mdx; iNOS-null mice without exercise and post-exercise at 6- and 10-weeks of age (n=3 for each set, areas of fibrosis (arrows for noexercise), areas of muscle edema (arrow heads for post-exercise)). (D) Bilateral albumin staining in quadriceps and gastrocnemii from mdx; iNOS-null mice at 6- and 10-weeks of age.

Previous reports show that genetic ablation of nNOS in mdx mice does not alter mdx muscle pathology (Chao et al. 1998; Crosbie et al. 1998) and that the induction of iNOS expression in mdx mice contributes to muscle fiber damage (Bellinger et al. 2009; Villalta et al. 2009). Comparative ambulation distances from wild-type, mdx, mdx; iNOS-null, and mdx; nNOS-null mice demonstrated that genetic ablation of iNOS or nNOS decreased mdx performance after exercise (FIG. 18D). Despite data that mdx; iNOS-null muscle have less muscle damage (Villalta et al. 2009), their reduced ambulation compared to mdx mice was consistent with increased muscle pathology in 6- and 10-week old mdx; iNOSnull mice (FIG. 20). The mdx; Utrn-null mice showed significant loss of ambulation after mild exercise (FIG. 18E), consistent with their more severe muscle pathology (Grady et al. 1997). Lastly, post-exercise ambulation distance of control and mdx mice were compared to that of mdx mice pretreated with phosphodiesterase 5A inhibitor (FIG. 18F). Phosphodiesterase 5A inhibitor treatment improved mdx mouse ambulation. These data demonstrate that the six-minute ambulation assay is a highly responsive test of disease severity and functional response with mdx mice.

The iNOS gene is upregulated and shown to contribute to the pathology in mdx muscle (Weiss et al. 2010; McDonald et al. 2005). Referring now to FIG. 20, mice deficient in dystrophin and iNOS were generated by breeding mdx and iNOS-null mice for two generations. Muscle pathology from mdx; iNOS-null mice at 6- and 10-weeks of age were analyzed. Compared to mdx mice before and after mild exercise (Kobayashi et al. 2008), quantitative vertical activity and serum creatine kinase of mdx; iNOS-null mice was similar. There was also no difference in the appearance of myoglobinuria from mdx; iNOS-null mice compared to mdx mice. Normally, mdx mice only show substantial $T_2$-weighted changes in magnetic resonance imaging after exercise. With mdx; iNOS-null mice, several areas of $T_2$-weighted changes were evident without exercise, suggestive of areas of fibrosis. After exercise, asymmetrical $T_2$-weighted changes appeared suggestive of muscle edema or inflammation. Bilateral analysis of muscle pathology by albumin staining also indicated asymmetrical pathology.

Figure 21:
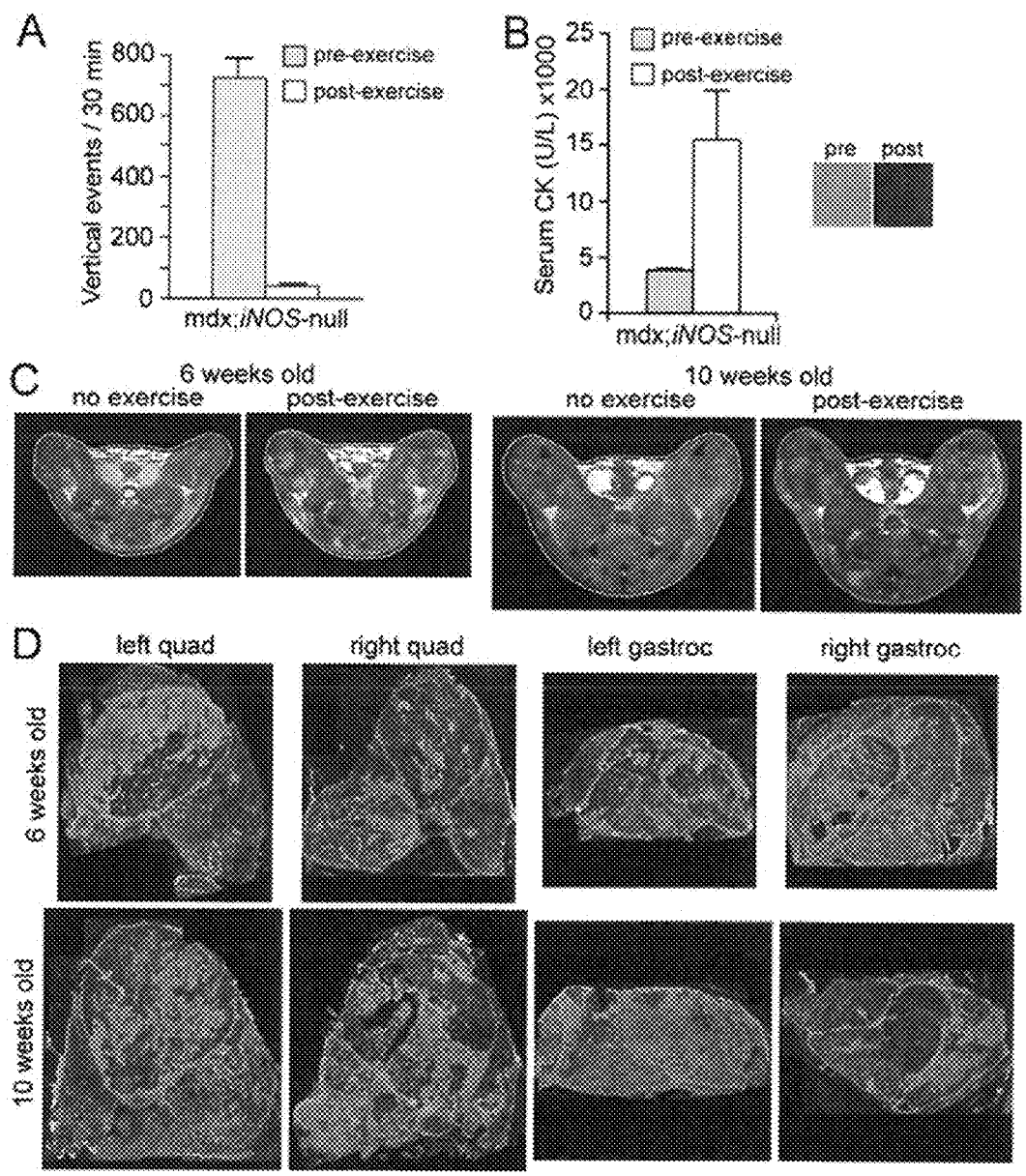
FIG. 21. illustrates asymmetric pathology of mdx mice. (A) Representative coronal magnetic resonance imaging scans of wild-type and mdx mouse hind quarters. Scans shown for no-ex and post-ex are from the same mouse. Localized areas of fibrosis (small white arrows) are detectable in mdx mice. $T_2$-weighted changes (large white arrows) from mdx mice are indicative of muscle edema or inflammation (n=5 for each). (B) Representative microscope images from bilateral analysis of quadriceps muscles (quads) and gastrocnemius muscles (gastrocs) from mdx mice post-exercise. Areas of Evans Blue Dye uptake into damaged muscle fibers (white arrows) and side the mouse leaned on are noted (n=6). (C) Four mdx mice were I.V. injected with Evans Blue Dye then subjected to mild exercise. Quadriceps (quad) and gastrocnemius (gastroc) muscles were isolated separately. Total Evans Blue Dye was quantified for each muscle isolated. Measurements were done in triplicate, error bars are SEM. (D) Absolute differences in percent force deficits between left and right mdx extensor digitorum longus muscles. Error bars are SEM. (*) Significant difference (P=0.012) was observed between values for exercised mice compared with those of non-exercised mice.

Bilateral analysis of mdx hind leg skeletal muscles and asymmetric pathology. When mdx mice were treadmill exercised, each mdx mouse, unlike wild-type controls, consistently leaned to one side of the treadmill. Notably, mdx mice subjected to multiple rounds of treadmill exercise leaned to the same side for each run suggesting that dystrophin deficiency causes asymmetric skeletal muscle pathology or weakness. To test this, $T_2$-weighted MRI of wild-type and mdx mouse hind-quarters were performed, without exercise and after mild exercise (FIG. 21A). Post-exercise changes in $T_2$-weighted MRI show up as lighter areas on scans and indicate changes in water content, which represent muscle edema or inflammation. Coronal MRI scans of wild-type hind leg muscles showed no $T_2$-weighted changes (FIG. 21A, Wild-type panels). Coronal MRI scans of mdx mice without exercise showed no $T_2$-weighted changes, except some mice showed small areas of fibrosis (FIG. 21A, mdx no-ex, small arrowheads). Coronal images of the same mdx mice all showed a large increase in $T_2$-weighted changes after exercise (FIG. 21A, mdx post-ex, large arrowheads) that were always more in one leg than the contralateral leg, even in older mdx mice (FIG. 22).

Figure 22:
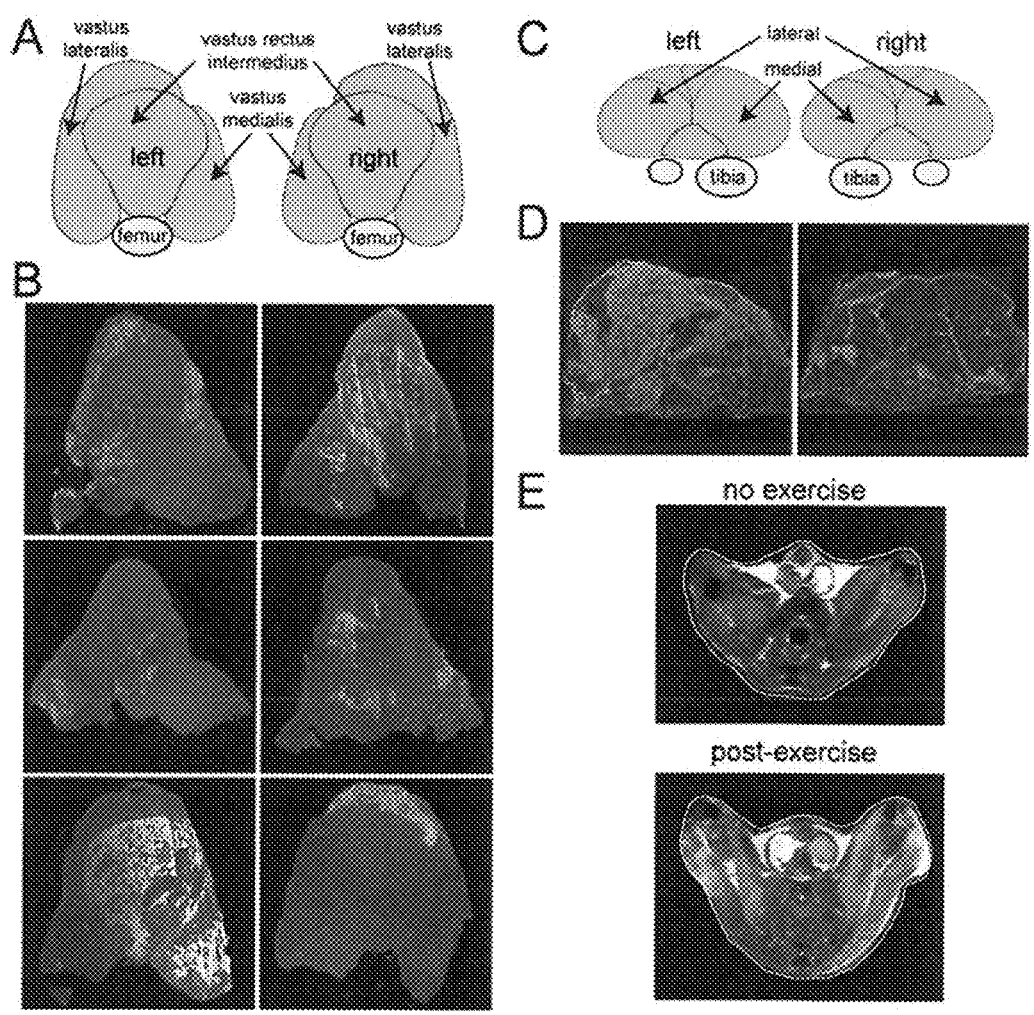
FIG. 22. illustrates asymmetric muscle pathology (A) Illustration of left and right quadriceps muscles from mice, noting the vastus lateralis, vastus intermedius and the vastus medialis. (B) Images of quadriceps from three different mdx mice showing that the Evans Blue Dye uptake for each muscle is vastly different within the same mouse. (C) Illustration of left and right gastrocnemius muscles from the mouse, noting the lateral and medial heads of the muscle. (D) Images of gastrocnemius muscles from an mdx mouse showing asymmetric detection of albumin. (E) Representative magnetic resonance images of 54 week old mdx mice with no exercise or post-exercise.

Referring to FIG. 22, which side and which quadriceps muscle one samples to look at muscle pathology will alter conclusions drawn for efficacy of a therapy. Sometimes only the vastus lateralis or the vastus medialis shows Evans Blue Dye uptake, whereas the vastus rectus intermedius can show no uptake, suggesting no damage. Or uptake can be unilateral in that one leg will show uptake but the contralateral leg will not. Analysis by detection of albumin demonstrates similar asymmetric muscle pathology. Older mdx mice have a more even distribution of muscle pathology based on Evans Blue Dye quantitation (McDonald et al. 2009). However, more muscles are affected as the mice get older too. $T_2$-weighted changes are more in older mdx mice, appear without exercise, yet still appear asymmetrical.

The leaning and sometimes unilateral appearance of $T_2$-weighted changes in mdx hind leg muscles suggested asymmetric pathology and weakness. Using EBD, mdx muscle damage was assessed. Damaged or necrotic muscle fibers stain positive for endogenous extracellular proteins like albumin or IgG/M (Blake et al. 2002). EBD binds albumin In unexercised mdx mice, muscle fibers that stain positive for EBD are also the ones that are positive for albumin or mouse IgG/M (Straub et al. 1997; Wooddell et al. 2010). Thus, detection of EBD uptake into skeletal muscle is an accurate index of muscle pathology. To test asymmetric muscle pathology with mdx mice, bilateral examination of EBD staining in mdx quadriceps and gastrocnemius muscles after exercise was performed (FIG. 21B). EBD detection in the quadriceps and gastrocnemii muscles was asymmetric in every mouse tested; in some cases, only one side featured detectable EBD/albumin uptake into muscle (FIG. 22). Quantitatively, total EBD measurements confirmed variable EBD uptake from each mdx mouse and asymmetrical EBD uptake in mdx quadriceps and gastrocnemius muscles after exercise (FIG. 21C). To test if this asymmetrical pathology translated to asymmetrical muscle contractile properties, the susceptibility to contraction induced injury between the right and left muscles of mdx mice was compared (FIG. 21D). For mice without exercise and mice after exercise, isolated extensor digitorum longus muscles were exposed to a lengthening contraction protocol and force deficit was determined. Exercise heightened the disparity between right and left muscles for susceptibility to injury. With exercise, the more injury-prone muscles of each mouse incurred force deficits of 50±4% which were typically two-fold greater than the force deficits of the contralateral muscles, which averaged 31±3%. Thus, post-stretch force deficits were also asymmetric in mdx mice.

Figure 23:
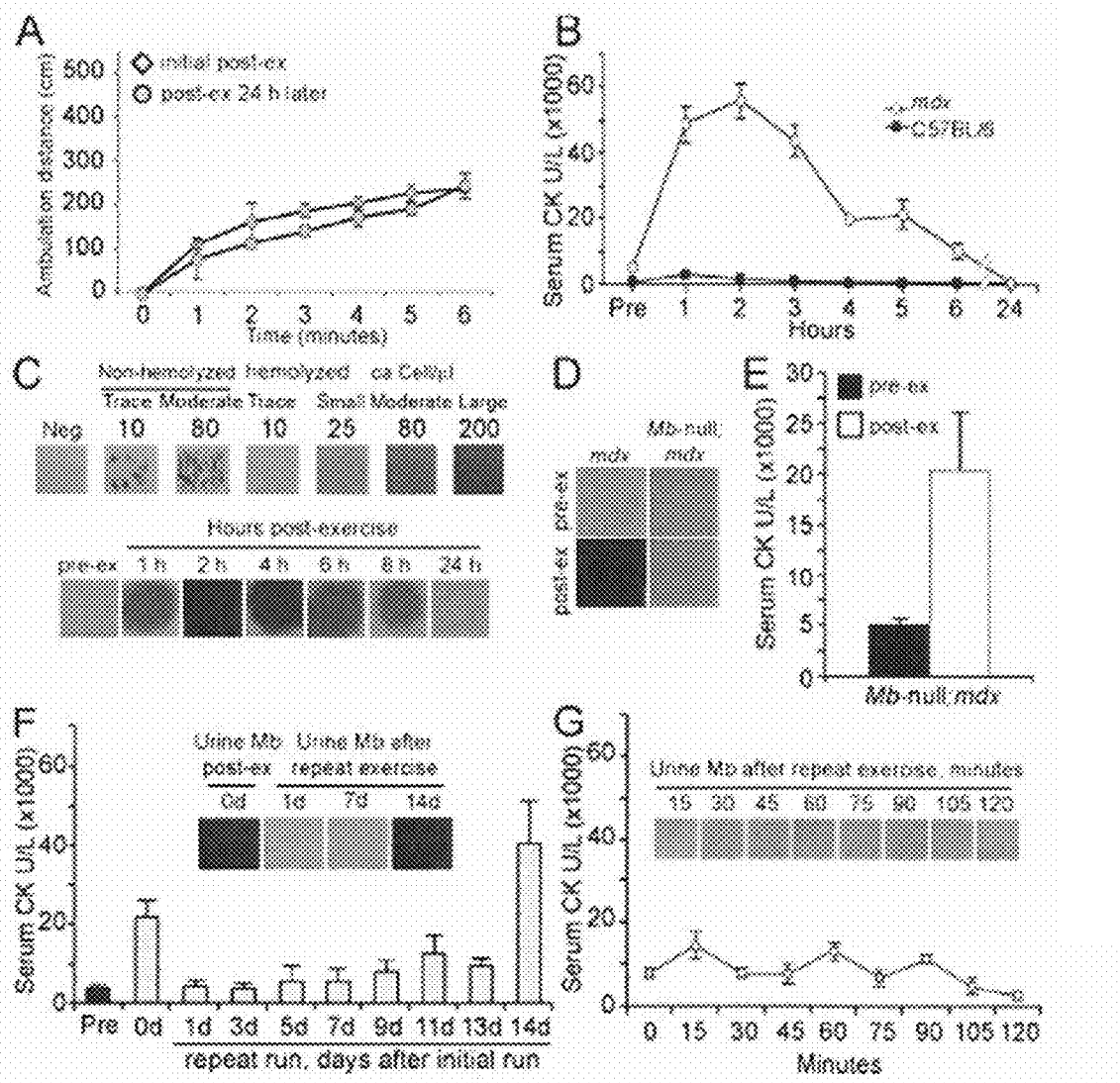
FIG. 23. illustrates post-exercise ambulation, serum creatine kinase (sCK), and myoglobinuria. (A) Six-minute ambulation distance post-exercise and after a repeated exercise 24 h later (n=4). (B) Serum CK from C57BL/6 and mdx mice before (pre) and at different time points after exercise (n=4 for each). (C) The presence of heme in the urine was assessed using urine dipsticks. Key for heme amounts is displayed (n=3 for each). (D) Urine collected pre- and post-exercise from littermate mdx and Mb-null; mdx mice were tested on dipstick strips (n=3 per analysis). (E) Serum CK before and 2 hours after exercise from Mb-null; mdx mice (n=4). (F) After an initial bout of exercise, eight sets of mdx mice, at different intervals (1 d, 3 d, 5 d, 7 d, 9 d, 11 d, 13 d, and 14 d), were re-exercised and sCK was measured (0 d n=40, 1 d n=5, 3 d n=5, 5 d n=6, 7 d n=4, 9 d n=4, 11 d n=3, 13 d n=6, and 14 d n=7), and myoglobinuria was tested (inset). (G) Nine sets of mdx mice were exercise and then 24 h later were exercised again. Each set of mice represented a time point. Serum CK was assayed at T=0, 15, 30, 45, 60, 75, 90, 105, and 120 min after the repeated exercise. (T=0 n=11, T=15 n=6, T=30, 45, and 60 n=6, T=75, 90, 105, and 120n=4), and myoglobinuria was tested with representative results in the inset. Error bars are SEM.

Timing of indices of muscle pathology in mdx mice. Each time mdx exercised, they leaned to the same side. However, repeating the exercise did not significantly affect the post-exercise ambulation performance (FIG. 23A). This lack of alteration in ambulation after a repeated exercise suggested that there was no further muscle damage occurring. To test this, indices of muscle damage and necrosis were tested by determining the peak analysis time for sCK in wild-type and mdx mice after exercise (FIG. 23B). Generally, sCK levels from mdx mice were elevated above control mouse levels without exercise (FIG. 23B, 4903.09+/−443.76 U/L). After exercise, sCK consistently peaked to hyperCKemia levels 2 hours after exercise (FIG. 23B, 55,850.77+/−5523.04 U/L) and gradually dissipated to below pre-exercise sCK levels (FIG. 23B, 565.45+/−200.66 U/L) by 24 hours. With wild-type mice, sCK readings were consistently below 500 U/L with a slight peak 1 hour postexercise. Wild-type sCK activity readings went below pre-exercise levels by 6 hours.

Urine of mdx mice pre- and post-exercise was assayed using urine dipsticks (FIG. 23C). Similar to the pattern of sCK post-exercise, heme detection in mdx urine peaked 2 hours postexercise and dissipated by 6 hours, with no evidence of heme in the urine by 24 hours postexercise. To determine which heme protein the dipstick test was detecting, myoglobin-null (Mb-null)(Garry et al. 1998) and mdx mice were crossed and sCK and urine of Mb-null; mdx mouse were tested (FIG. 23D, E). Mb-null; mdx were negative for the presence of heme in their urine postexercise, but had elevated sCK before exercise and hyperCKemia post-exercise. Thus, a positive result on urine dipsticks from mdx mice indicates that mdx mice have exercise-induced myoglobinuria, which corresponded with hyperCKemia levels.

Consistent with no significant change in mdx ambulation performance, mdx sCK levels did not increase as it did during the initial exercise. Mile exercise was repeated with different sets of mdx mice at 1, 3, 5, 7, 9, 11, 13 and 14 days after the initial exercise, and sCK was measured at the 2 hour time point (FIG. 23F). After the rise in sCK to hyperCK levels following the first bout of exercise on day 0 (0 d), sCK from the mdx mice rose to that same level only when the interval between exercise was 14 days. Myoglobinuria followed the same pattern (FIG. 23F, inset). To test for early peaking of sCK, mdx mice were exercised twice in a 24 hour interval, and sCK was collected at several time points up to 2 hours following the second bout of exercise (FIG. 23G). Twenty-four hours since an initial mild exercise, different sets of mdx mice were mildly exercised again and sCK was measured at time intervals post-exercise (0, 15, 30, 45, 60, 75, 90, 105, and 120-minutes). Different sets of mice were used for each time point. Readings for sCK remained relatively close to elevated pre-exercise levels within each time point, consistent with ongoing regeneration. At the 2 hour mark, sCK readings were the lowest. Myoglobinuria was undetectable during this 2 hour analysis (FIG. 23G, inset).

Discussion

Despite advances in the identification of potential therapeutic targets using the mdx mouse in preclinical studies, a therapy for DMD remains elusive. This discrepancy has caused researchers to question the mdx mouse as a model for DMD as well as the validity of translating promising results from mdx preclinical studies into clinical trials. The data presented here demonstrate that when properly assayed, the mdx mouse is an ideal model for preclinical studies for Duchenne muscular dystrophy.

A six-minute ambulation test was designed for mice as an endpoint measure for DMD preclinical studies. Timed submaximal exercise performance is used as a standard outcome measure in clinical trials to test the efficacy of a treatment on improving mobility. This mild exercise is used for a variety of diseases in which patients experience physical limitations. The step-activity monitor and six-minute walk test are two forms of this kind of testing that are used with normal and ambulatory DMD boys (McDonald et al. 2005; McDonald et al. 2009). These two assays were combined into the six-minute ambulation distance test for mice. After subjecting the mice to mild exercise, this assay is responsive to varying degrees of muscle pathology in that ambulation increased or decreased with known changes in muscle function among the different mouse models and with a pharmacological treatment.

Importantly, from the observation that the mdx mice leaned to one side of the treadmill during exercise, mdx mice have asymmetric muscle pathology in their quadriceps and gastrocnemius skeletal muscles. This finding is significant, as several therapeutic studies for DMD use muscle pathology as an endpoint measure, and many therapeutic preclinical studies test one leg of an mdx mouse and use the contralateral leg as a control.

The asymmetric mdx muscle pathology may be related to variability in dystrophinopathy patients, with some muscles being affected while neighboring, or other muscles being spared from pathology. Like with humans, mice have a lateral preference (Collins R. L. 1968), i.e. display handedness. Whether this laterality influences mdx physiopathology and susceptibility to contraction-induced injury or muscle pathology influences the laterality of mdx mice, remains unknown. Innate laterality could influence mdx pathology, whereby the dominant side gets more use than the other and eventually becomes more severely affected. Conversely, asymmetric mdx muscle pathology could influence laterality. Clinically, muscle weakness in DMD patients is often described as being symmetric. However, DMD patients do have asymmetry in muscle weakness that could be due to handedness or to a learned adaptive response. Recently, manifesting female carriers of DMD mutations were reported to present with notable asymmetrical clinical weakness (Soltanzadeh et al. 2010). Whether there is asymmetric muscle pathology with DMD patients is unknown as systematic bilateral analysis of skeletal muscle would require multiple muscle biopsies that would be difficult to ethically justify. Nevertheless, the findings presented here demonstrate that asymmetric muscle pathology as well as asymmetric weakness should be considered when taking biopsies for testing therapies in animal models as well as in patients.

The leaning of mdx mice during exercise is similar to what ambulatory DMD boys do to maintain balance and gait while walking (Gaudreault et al. 2010). Thus, improved mobility is a key endpoint measure. The increased performance in the six-minute ambulation assay of phosphodiesterase 5A inhibitor treated mdx mice was consistent with previous data that this treatment increases mdx postexercise vertical activity and reduces exercise-induced muscle edema (Kobayashi et al. 2008). Therefore, this pharmacological treatment validated the six-minute ambulation assay as a performance outcome measure for DMD preclinical mouse studies.

The ongoing necrosis of skeletal muscle and the asymmetric pathology and weakness could contribute to the reduced ambulation and leaning during exercise of mdx mice. Each time mdx mice were exercised, they leaned to the same side, and repeating the exercise did not significantly affect the post-exercise ambulation performance. Consistent with no change in ambulation performance, mdx sCK levels did not increase as it did during the initial exercise. Despite each skeletal muscle fiber being susceptible to contraction-induced injury due to the lack of dystrophin, and chronic inflammation in the mdx mouse (Acharyya et al. 2007), this lack of increase in sCK after subsequent exercise suggested that repeat exercise does not result in further muscle damage. The release of CK and myoglobin from normal muscle, however, is thought to activate an inflammatory response that enhances clearance of these proteins, such that subsequent muscle damage fails to give rise to elevated muscle-cell proteins in the blood (Black et al. 2008; Hyatt et al. 1998; Marqueste et al. 2008). No evidence of sCK or myoglobinuria peaking sooner was observed. It is not clear why biomarkers of muscle damage follow this pattern. Nevertheless, the data presented here demonstrate the importance of mouse activity and analysis time for these muscle damage biomarkers. If the normally sedentary mdx mouse is active one to fourteen days before a sCK analysis, sCK levels will likely be lower than expected when analyzed. Thus, a low sCK reading in an mdx mouse preclinical study may not be a response to the therapeutic agent, but simply a reflection of mouse activity during the trial period.

In summary, presented here is the use of a six-minute ambulation test, in conjunction with refined analyses of muscle pathology and biomarkers of muscle damage, as preclinical endpoint measures relevant for muscular dystrophy clinical trials. Future preclinical and clinical trial study designs for muscular dystrophy should take into account possible baseline asymmetry of muscle pathology. Furthermore, preclinical study designs should consider the circadian rhythm in mouse physiological performance analyses and mouse activity before muscle damage biomarkers are assayed. Positive findings using these endpoint measures will enhance the translatability of future preclinical studies for Duchenne and other muscular dystrophies.

REFERENCES

Acharyya S, Villalta S A, Bakkar N, et al. Interplay of IKK/NF-kappaB signaling in macrophages and myofibers promotes muscle degeneration in Duchenne muscular dystrophy. J Clin Invest. 2007 April;117(4):889-901.

Anderson, J. E. & Vargas, C. Correlated NOS-Imu and myf5 expression by satellite cells in mdx mouse muscle regeneration during NOS manipulation and deflazacort treatment. Neuromuscul Disord 13, 388-96 (2003).

Anderson, J. E., Weber, M. & Vargas, C. Deflazacort increases laminin expression and myogenic repair, and induces early persistent functional gain in mdx mouse muscular dystrophy. Cell Transplant 9, 551-64 (2000).

Archer, J. D., Vargas, C. C. & Anderson, J. E. Persistent and improved functional gain in mdx dystrophic mice after treatment with L-arginine and deflazacort. Faseb J 20, 738-40 (2006).

Asai, A. et al. Primary role of functional ischemia, quantitative evidence for the two-hit mechanism, and phosphodiesterase-5 inhibitor therapy in mouse muscular dystrophy. PLoS ONE 2, e806 (2007).

Barbato, J. C. Nicorandil: the drug that keeps on giving. Hypertension 46, 647-8 (2005).

Bellinger A M, Reiken S, Carlson C, et al. Hypernitrosylated ryanodine receptor calcium release channels are leaky in dystrophic muscle. Nat Med. 2009 March;15(3):325-30.

Black C D, McCully K K. Muscle injury after repeated bouts of voluntary and electrically stimulated exercise. Med Sci Sports Exerc. 2008 September;40(9):1605-15.

Blake D J, Weir A, Newey S E, Davies K E. Function and genetics of dystrophin and dystrophin-related proteins in muscle. Physiol Rev. 2002 April;82(2):291-329.

Bloom T J. Age-related alterations in cyclic nucleotide phosphodiesterase activity in dystrophic mouse leg muscle. *Can J Physiol Pharmacol.* 2005; 83:1055-60.

Bloom T J. Cyclic nucleotide phosphodiesterase isozymes expressed in mouse skeletal muscle. *Can J Physiol Pharmacol.* 2002; 80:1132-5.

Brooks S V, Faulkner J A. Contractile properties of skeletal muscles from young, adult and aged mice. J Physiol. 1988 October;404:71-82.

Chao, D. S., Silvagno, F. & Bredt, D. S. Muscular dystrophy in mdx mice despite lack of neuronal nitric oxide synthase. J Neurochem 71, 784-9 (1998).

Cohn, R. D. et al. Prevention of cardiomyopathy in mouse models lacking the smooth muscle sarcoglycan-sarcospan complex. J Clin Invest 107, R1-7 (2001).

Collins R L. On the inheritance of handedness. I. Laterality in inbred mice. J Hered. 1968 January-February; 59(1): 9-12.

Consolino C M, et al. Muscles of mice deficient in alpha-sarcoglycan maintain large masses and near control force values throughout the life span. *Physiol Genomics.* 2005; 22:244-56.

Crosbie, R. H. et al. Membrane targeting and stabilization of sarcospan is mediated by the sarcoglycan subcomplex. J Cell Biol 145, 153-65 (1999).

Crosbie, R. H. et al. mdx muscle pathology is independent of nNOS perturbation. Hum Mol Genet 7, 823-9 (1998).

Duclos, F. et al. Progressive muscular dystrophy in alpha-sarcoglycan-deficient mice. J Cell Biol 142, 1461-71 (1998).

Durbeej, M. et al. Disruption of the beta-sarcoglycan gene reveals pathogenetic complexity of limb-girdle muscular dystrophy type 2E. Mol Cell 5, 141-51(2000).

Ervasti, J. M. & Campbell, K. P. Membrane organization of the dystrophin-glycoprotein complex. Cell 66, 1121-31 (1991).

Eu, J. P. et al. Concerted regulation of skeletal muscle contractility by oxygen tension and endogenous nitric oxide. Proc Natl Acad Sci USA 100, 15229-34(2003).

Fadel, P. J., Zhao, W. & Thomas, G. D. Impaired vasomodulation is associated with reduced neuronal nitric oxide synthase in skeletal muscle of ovariectomized rats. J Physiol 549, 243-53 (2003).

Garry D J, Ordway G A, Lorenz J N, et al. Mice without myoglobin. Nature. 1998 October29; 395(6705):905-8.

Gaudreault N, Gravel D, Nadeau S, Houde S, Gagnon D. Gait patterns comparison of children with Duchenne muscular dystrophy to those of control subjects considering the effect of gait velocity. Gait Posture. 2010 Jul. 2.

Glowka, F. K. Stereoselective pharmacokinetics of ibuprofen and its lysinate from suppositories in rabbits. Int J Pharm 199, 159-66 (2000).

Grady R M, Teng H, Nichol M C, Cunningham J C, Wilkinson R S, Sanes J R. Skeletal and cardiac myopathies in mice lacking utrophin and dystrophin: a model for Duchenne muscular dystrophy. Cell. 1997; 90(4):729-38.

Grady R M, Merlie J P, Sanes J R. Subtle neuromuscular defects in utrophin-deficient mice. J Cell Biol. 1997 Feb. 24; 136(4):871-82.

Grady, R. M. et al. Role for alpha-dystrobrevin in the pathogenesis of dystrophin-dependent muscular dystrophies. Nat Cell Biol 1, 215-20 (1999).

Gupta, M., Kovar, A. & Meibohm, B. The clinical pharmacokinetics of phosphodiesterase-5 inhibitors for erectile dysfunction. J Clin Pharmacol 45, 987-1003(2005).

Harper, S. Q. et al. Modular flexibility of dystrophin: implications for gene therapy of Duchenne muscular dystrophy. Nat Med 8, 253-61 (2002).

Hougee, S. et al. Oral administration of the NADPH-oxidase inhibitor apocynin partially restores diminished cartilage proteoglycan synthesis and reduces inflammation in mice. Eur J Pharmacol 531, 264-9 (2006).

Huang P L, et al. Hypertension in mice lacking the gene for endothelial nitric oxide synthase. *Nature.* 1995; 377:239-42.

Hyatt J P, Clarkson P M. Creatine kinase release and clearance using MM variants following repeated bouts of eccentric exercise. Med Sci Sports Exerc. 1998 July;30(7): 1059-65.

Imamura M, Mochizuki Y, Engvall E, Takeda S. i. {varepsilon}-Sarcoglycan compensates for lack of {alpha}-sarcoglycan in a mouse model of limb-girdle muscular dystrophy. *Hum. Mol. Genet.* 2005; 14:775-783.

Johnson, J. E., Wold, B. J. & Hauschka, S. D. Muscle creatine kinase sequence elements regulating skeletal and cardiac muscle expression in transgenic mice. Mol Cell Biol 9, 3393-9 (1989).

Judge L M, Haraguchiln M, Chamberlain J S. Dissecting the signaling and mechanical functions of the dystrophin-glycoprotein complex. *J Cell Sci.* 2006; 119:1537-46.

Kalkman J S, Schillings M L, Zwarts M J, van Engelen B G, Bleijenberg G. The development of a model of fatigue in neuromuscular disorders: A longitudinal study. *J Psychosom Res.* 2007; 62:571-9.

Kameya, S. et al. alpha 1-syntrophin gene disruption results in the absence of neuronal-type nitric-oxide synthase at the sarcolemma but does not induce muscle degeneration. J Biol Chem 274, 2193-200 (1999).

Kass D A, Champion H C, Beavo J A. Phosphodiesterase type 5: expanding roles in cardiovascular regulation. *Circ Res.* 2007; 101:1084-95.

Kinugawa, S. et al. Limited exercise capacity in heterozygous manganese superoxide dismutase gene-knockout mice: roles of superoxide anion and nitric oxide. Circulation 111, 1480-6 (2005).

Kobayashi et al. Sarcolemma-localized n NOS is required to maintain activity after mild exercise. Nature 456, 511-5 (2008).

Lebakken, C. S. et al. Sarcospan-deficient mice maintain normal muscle function. Mol Cell Biol 20, 1669-77. (2000).

Lynch, G. S. et al. Contractile properties of diaphragm muscle segments from old mdx and old transgenic mdx mice. Am J Physiol 272, C2063-8 (1997).

Marden F A, Connolly A M, Siegel M J, Rubin D A. Compositional analysis of muscle in boys with Duchenne muscular dystrophy using MR imaging. *Skeletal Radiol.* 2005; 34:140-8.

Marqueste T, Giannesini B, Fur Y L, Cozzone P J, Bendahan D. Comparative MRI analysis of T2 changes associated with single and repeated bouts of downhill running leading to eccentric-induced muscle damage. J Appl Physiol. 2008 July;105(1):299-307.

McDonald C M, Widman L M, Walsh D D, Walsh S A, Abresch R T. Use of step activity monitoring for continuous physical activity assessment in boys with Duchenne muscular dystrophy. Arch Phys Med Rehabil. 2005 April;86(4): 802-8.

McDonald C M, Henricson E K, Han J J, et al. The 6-minute walk test as a new outcome measure in Duchenne muscular dystrophy. Muscle Nerve. 2009 Nov. 25.

Miki, T. et al. Mouse model of Prinzmetal angina by disruption of the inward rectifier Kir6. 1. Nat Med 8, 466-72 (2002).

Narkar, V. A. et al. AMPK and PPARdelta agonists are exercise mimetics. Cell 134, 405-15 (2008).

Ozawa E, Mizuno Y, Hagiwara Y, Sasaoka T, Yoshida M. Molecular and cell biology of the sarcoglycan complex. *Muscle Nerve.* 2005; 32:563-76.

Perretti, M. & Ahluwalia, A. The microcirculation and inflammation: site of action for glucocorticoids. Microcirculation 7, 147-61 (2000).

Persson J, Ekelund U, Grande P O. Endogenous nitric oxide reduces microvascular permeability and tissue oedema during exercise in cat skeletal muscle. *J Vasc Res.* 2003; 40:538-46.

Phillips B A, Mastaglia F L. Exercise therapy in patients with myopathy. *Curr Opin Neurol.* 2000; 13:547-52.

Pomplun, D., Mohlig, M., Spranger, J., Pfeiffer, A. F. & Ristow, M. Elevation of blood glucose following anaesthetic treatment in C57BL/6 mice. Horm Metab Res 36, 67-9 (2004).

Prior, S. J. et al. Reduced skeletal muscle capillarization and glucose intolerance. Microcirculation 16, 203-12 (2009).

Punkt, K. et al. Nitric oxide synthase is up-regulated in muscle fibers in muscular dystrophy. Biochem Biophys Res Commun 348, 259-64 (2006).

Radley H G, De Luca A, Lynch G S, Grounds M D. Duchenne muscular dystrophy: focus on pharmaceutical and nutritional interventions. *Int J Biochem Cell Biol.* 2007; 39:469-77.

Raisis, A. L. Skeletal muscle blood flow in anaesthetized horses. Part II: effects of anaesthetics and vasoactive agents. Vet Anaesth Analg 32, 331-7 (2005).

Roberds, S. L., Anderson, R. D., Ibraghimov-Beskrovnaya, O. & Campbell, K. P. Primary structure and muscle-specific expression of the 50-kDa dystrophin-associated glycoprotein (adhalin). J Biol Chem 268, 23739-42. (1993).

Schillings M L, et al. Experienced and physiological fatigue in neuromuscular disorders. *Clin Neurophysiol.* 2007; 118:292-300.

Scime, A. & Rudnicki, M. A. Molecular-targeted therapy for duchenne muscular dystrophy: progress and potential. Mol Diagn Ther 12, 99-108 (2008).

Seddon, M. D., Chowienczyk, P. J., Brett, S. E., Casadei, B. & Shah, A. M. Neuronal Nitric Oxide Synthase Regulates Basal Microvascular Tone in Humans In Vivo. Circulation, CIRCULATIONAHA.107.744540 (2008).

Sigmund, C. D. et al. Regulated tissue- and cell-specific expression of the human renin gene in transgenic mice. Circ Res 70, 1070-9 (1992).

Soltanzadeh P, Friez M J, Dunn D, et al. Clinical and genetic characterization of manifesting carriers of DMD mutations. Neuromuscul Disord. 2010 August; 20(8):499-504.

Spurney C F, Gordish-Dressman H, Guerron A D, et al. Preclinical drug trials in the mdx mouse: assessment of reliable and sensitive outcome measures. Muscle Nerve. 2009 May; 39(5):591-602.

St-Pierre, S. J. et al. Glucocorticoid treatment alleviates dystrophic myofiber pathology by activation of the calcineurin/NF-AT pathway. Faseb J 18, 1937-9 (2004).

Stamler, J. S. & Meissner, G. Physiology of nitric oxide in skeletal muscle. Physiol Rev 81, 209-237 (2001).

Straub V, Rafael J A, Chamberlain J S, Campbell K P Animal models for muscular dystrophy show different patterns of sarcolemmal disruption. J Cell Biol. 1997 Oct. 20;139(2):375-85.

Straub, V. et al. epsilon-sarcoglycan replaces alpha-sarcoglycan in smooth muscle to form a unique dystrophin-glycoprotein complex. J Biol Chem 274, 27989-96. (1999).

Suzuki N, et al. NO production results in suspension-induced muscle atrophy through dislocation of neuronal NOS. *J Clin Invest.* 2007; 117:2468-2476.

Takimoto, E. et al. Chronic inhibition of cyclic GMP phosphodiesterase 5A prevents and reverses cardiac hypertrophy. Nat Med 11, 214-22 (2005).

Tanda, K. et al. Abnormal social behavior, hyperactivity, impaired remote spatial memory, and increased D1-mediated dopaminergic signaling in neuronal nitric oxide synthase knockout mice. Mol Brain 2, 19 (2009).

Terzis, G., Spengos, K., Manta, P., Sarris, N. & Georgiadis, G. Fiber type composition and capillary density in relation to submaximal number of repetitions in resistance exercise. J Strength Cond Res 22, 845-50 (2008).

Thomas G D, Shaul P W, Yuhanna I S, Froehner S C, Adams M E. Vasomodulation by skeletal muscle-derived nitric oxide requires alpha-syntrophin-mediated sarcolemmal localization of neuronal Nitric oxide synthase. *Circ Res.* 2003; 92:554-60.

Thomas, G. D. et al. Impaired metabolic modulation of alpha-adrenergic vasoconstriction in dystrophin-deficient skeletal muscle. Proc Natl Acad Sci USA 95, 15090-5 (1998).

Thompson S, Lupi D, Hankins M W, Peirson S N, Foster R G. The effects of rod and cone loss on the photic regulation of locomotor activity and heart rate. Eur J Neurosci. 2008 August; 28(4):724-9.

Torelli S, et al. Absence of neuronal nitric oxide synthase (nNOS) as a pathological marker for the diagnosis of Becker muscular dystrophy with rod domain deletions. *Neuropathol Appl Neurobiol.* 2004; 30:540-5.

Tsunoda, M., Takezawa, K., Yanagisawa, T., Kato, M. & Imai, K. Determination of catecholamines and their 3-O-methyl metabolites in mouse plasma. Biomed Chromatogr 15, 41-4 (2001).

Villalta S A, Nguyen H X, Deng B, Gotoh T, Tidball J G. Shifts in macrophage phenotypes and macrophage competition for arginine metabolism affect the severity of muscle pathology in muscular dystrophy. Hum Mol Genet. 2009 Feb. 1; 18(3):482-96.

Voikar, V., Polus, A., Vasar, E. & Rauvala, H. Long-term individual housing in C57BL/6J and DBA/2 mice: assessment of behavioral consequences. Genes Brain Behav 4, 240-52 (2005).

Walker, D. K. et al. Pharmacokinetics and metabolism of sildenafil in mouse, rat, rabbit, dog and man. Xenobiotica 29, 297-310 (1999).

Wang, M. X. et al. Nitric oxide in skeletal muscle: inhibition of nitric oxide synthase inhibits walking speed in rats. Nitric Oxide 5, 219-32 (2001).

Wang R, Urso M L, Zambraski E J, Rader E P, Campbell K P, Liang B T. Adenosine A(3) receptor stimulation induces protection of skeletal muscle from eccentric exercise-mediated injury. Am J Physiol Regul Integr Comp Physiol. 2010 July;299(1):R259-67.

Wehling, M., Spencer, M. J. & Tidball, J. G. A nitric oxide synthase transgene ameliorates muscular dystrophy in mdx mice. J Cell Biol 155, 123-31 (2001).

Weiss R M, Kerber R E, Jones J K, et al. Exercise-Induced Left Ventricular Systolic Dysfunction in Women Heterozygous for Dystrophinopathy. J Am Soc Echocardiogr. 2010 August;23(8):848-53.

Williamson, R. A. et al. Dystroglycan is essential for early embryonic development: disruption of Reichert's membrane in Dagl-null mice. Hum Mol Genet 6, 831-41 (1997).

Wooddell C I, Zhang G, Griffin J B, Hegge J O, Huss T, Wolff J A. Use of Evans blue dye to compare limb muscles in exercised young and old mdx mice. Muscle Nerve. 2010 April;41(4):487-99.

Yokoyama T, Lisi T L, Moore S A, Sluka K A. Muscle fatigue increases the probability of developing hyperalgesia in mice. *J Pain.* 2007; 8:692-9.

Zwarts M J, Bleijenberg G, van Engelen B G. Clinical neurophysiology of fatigue. *Clin Neurophysiol.* 2007 doi: 10.1016/j.clinph.2007.09.126.

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and method steps described herein may be used alone or in combination with other compositions and method steps. It is to be expected that various equivalents, alternatives and modifications are possible. Citations to a number of non-patent references are made herein. The cited references are incorporated by reference herein in their entireties. In the event that there is an inconsistency between a definition of a term in the specification as compared to a definition of the term in a cited reference, the term should be interpreted based on the definition in the specification.

Table

TABLE 1

Summary of the 425 human muscular biopsies stained for nNOS.

| Disease | nNOS-negative | nNOS-reduced | nNOS-normal | Total cases stained |
|---|---|---|---|---|
| DMD | 27 | 0 | 0 | 27 |
| BMD | 20 | 10 | 0 | 30 |

TABLE 1-continued

Summary of the 425 human muscular biopsies stained for nNOS.

| Disease | nNOS-negative | nNOS-reduced | nNOS-normal | Total cases stained |
|---|---|---|---|---|
| DMD carriers | Mosaic of negative and positive fibers | | | 4 |
| CMD/LGMD (POMT1, POMT2, POMGnT1, FKTN) | 2 | 8 | 0 | 10 |
| Other dystroglycanopathies not genetically defined | 7 | 76 | 8 | 91 |
| LGMD-2A | 0 | 0 | 1 | 1 |
| LGMD-2B | 0 | 10 | 2 | 12 |
| LGMD-2D | 0 | 3 | 0 | 3 |
| LGMD-2E | 0 | 2 | 0 | 2 |
| LGMD-2I | 0 | 9 | 1 | 10 |
| Other SG (includes three 2C cases) | 0 | 6 | 0 | 6 |
| UCMD | 3 | 21 | 1 | 25 |
| MDC1A | 1 | 3 | 1 | 5 |
| Myositis | 2 | 6 | 0 | 8 |
| Autophagic vacuolar myopathy | 0 | 5 | 0 | 5 |
| Myopathies w/o specific protein deficiencies | 0 | 100 | 86 | 186 |

We claim:

1. A method for reducing skeletal muscle fatigue in a patient having muscle fatigue due to increased age, the method consisting of administering to the patient an effective amount of sildenafil or a pharmaceutical salt thereof.

2. The method of claim 1, wherein the muscle fatigue due to increased age is characterized by increased PDE5A activity in skeletal muscle of the patient having muscle fatigue due to increased age in comparison to a patient not having the muscle fatigue.

3. A method for reducing skeletal muscle edema after exercise in a patient having muscle fatigue due to increased age, the method consisting of administering to the patient an effective amount of sildenafil or a pharmaceutical salt thereof.

4. The method of claim 3, wherein the muscle fatigue is characterized by increased PDE5A activity in skeletal muscle of the patient having the muscle fatigue due to increased age in comparison to a patient not having the muscle fatigue.

5. A method for reducing skeletal muscle damage after exercise in a patient having muscle fatigue due to increased age, the method consisting of administering to the patient an effective amount of sildenafil or a pharmaceutical salt thereof.

6. The method of claim 5, wherein the muscle fatigue is characterized by increased PDE5A activity in skeletal muscle of the patient having the muscle fatigue due to increased age in comparison to a patient not having the muscle fatigue.

* * * * *